United States Patent
Yu et al.

(10) Patent No.: US 10,716,271 B2
(45) Date of Patent: *Jul. 21, 2020

(54) SOY GENE CLUSTER REGIONS AND METHODS OF USE

(71) Applicant: Syngenta Participations AG, Basel (CH)

(72) Inventors: Ju-Kyung Yu, Research Triangle Park, NC (US); Becky Welsh Breitinger, Research Triangle Park, NC (US); David Plunkett, Minnetonka, MN (US); Ainong Shi, Fayetteville, AR (US); Daniel Dyer, Minnetonka, MN (US)

(73) Assignee: Syngenta Participations AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/034,570

(22) Filed: Jul. 13, 2018

(65) Prior Publication Data

US 2018/0310501 A1  Nov. 1, 2018

Related U.S. Application Data

(60) Continuation of application No. 14/967,716, filed on Dec. 14, 2015, now Pat. No. 10,045,494, which is a division of application No. 13/687,593, filed on Nov. 28, 2012, now Pat. No. 9,307,707.

(60) Provisional application No. 61/611,954, filed on Mar. 16, 2012.

(51) Int. Cl.
| | |
|---|---|
| *A01H 5/10* | (2018.01) |
| *A01H 1/04* | (2006.01) |
| *C12Q 1/6895* | (2018.01) |
| *C12N 15/82* | (2006.01) |

(52) U.S. Cl.
CPC .............. *A01H 1/04* (2013.01); *A01H 5/10* (2013.01); *C12N 15/8279* (2013.01); *C12N 15/8282* (2013.01); *C12N 15/8286* (2013.01); *C12Q 1/6895* (2013.01); *C12Q 2600/13* (2013.01); *C12Q 2600/156* (2013.01); *C12Q 2600/172* (2013.01)

(58) Field of Classification Search
None
See application file for complete search history.

(56) References Cited

U.S. PATENT DOCUMENTS

| 4,458,066 A | 7/1984 | Caruthers et al. |
| 2006/0137039 A1 | 6/2006 | Sebastian et al. |
| 2006/0288444 A1 | 12/2006 | McCarroll et al. |
| 2010/0192247 A1 | 7/2010 | Yu et al. |
| 2011/0185448 A1 | 7/2011 | Yu et al. |

FOREIGN PATENT DOCUMENTS

| WO | 2008054546 | 5/2008 |
| WO | 2009079729 | 7/2009 |
| WO | 2010009404 | 1/2010 |
| WO | 2010096227 | 8/2010 |

OTHER PUBLICATIONS

Soybean (*Glycine max*) Williams 82 clone gmw1-42i18, GenBank sequence AC144537, published Jul. 15, 2014, selected pages.*
Anderson et al., "Development of simple sequence repeat markers for the soybean rust fungus, Phakopsora pachyrhizi," Molecular Ecology Resources. vol. 8 pp. 1310-1312 (2008).
Bonde et al., "Evaluation of virulence of Phakopsora pachyrhizi and P. meibomiae isolates," Plant Dis. vol. 90 pp. 708-716 (2006).
Bromfield, K.R., and Hartwig, E.E., "Resistance to soybean rust and mode of inheritance," Crop Science. vol. 20 No. 2 pp. 254-255 (1980).
Calvo et al., "Two Major Recessive Soybean Genes Conferring Soybean Rust Resistance," Crop Science. vol. 28 No. 4 pp. 1350-1354 (2008).
Choi et al., "A Soybean Transcript Map: Gene Distribution, Haplotype and Single-Nucleotide Polymorphism Analysis," Genetics. vol. 176 pp. 685-696 (2007).
Choi et al., Supplemental Data "Consensus Soybean Genetic Map—Feb. 2007," 58 pages (2007).
Garcia et al., "Molecular mapping of soybean rust (*Phakopsora pachyrhizi*) resistance genes: discovery of a novel locus and alleles," Theoretical and Applied Genetics. vol. 117 pp. 545-553 (2008).
Hartman et al., "Breeding for Resistance to Soybean Rust," Plant Disease. vol. 89, No. 6 pp. 664-666 (2005).
Hartwig, and Bromfield, "Relationships among three genes conferring specific resistance to rust in soybeans," Crop Science. vol. 23 pp. 237-239 (1983).
Hyten, D.L., "Mapping soybean rust single gene resistance," Proc. 2007 Natl. Soybean Rust Symp., Louisville, Kentucky (Dec. 12-14, 2007).
Hyten et al., "High-throughput genotyping with the GoldenGate assay in the complex genome of soybean," Theoretical and Applied Genetics. vol. 116 pp. 945-952 (2008).
Hyten et al., "Map Location of the Rpp1 Locus that Confers Resistance to Soybean Rust in Soybean," Crop Science. vol. 47, No. 2 pp. 837-840 (2007).

(Continued)

*Primary Examiner* — Bratislav Stankovic
(74) *Attorney, Agent, or Firm* — R. Kody Jones

(57) ABSTRACT

Methods for conveying pathogen resistance into non-resistant soybean germplasm are provided. In some embodiments, the methods include introgressing pathogen resistance into a non-resistant soybean using one or more nucleic acid markers for marker-assisted breeding among soybean lines to be used in a soybean breeding program, wherein the markers are linked to and/or associated with pathogen resistance. Also provided are single nucleotide polymorphisms (SNPs) associated with resistance to pathogens; soybean plants, seeds, and tissue cultures produced by any of the disclosed methods; seed produced by the disclosed soybean plants; and compositions including amplification primer pairs capable of initiating DNA polymerization by a DNA polymerase on soybean nucleic acid templates to generate soybean marker amplicons.

6 Claims, No Drawings
Specification includes a Sequence Listing.

(56) References Cited

OTHER PUBLICATIONS

International Search Report corresponding to International Patent Application No. PCT/US2009/051003 dated Feb. 5, 2010.
McLean, R.J. and Bythe, D., "Inheritance of resistance to rust (*Phakopsora pachrhizi*) in soybean," Aust. J. Ahric. Res. vol. 31 pp. 951-956 (1980).
Miles et al., "Evaluation of Soybean Germplasm for Resistance to Phakospora pachyrhizi ," Plant Health Progress. (25 pages) (Accessed on Feb. 15, 2013) <http://www.plantmanagementnetwork.org/pub/php/research/2006/germplasm/>.
Monteros et al., "Mapping and Confirmation of the 'Hyuuga' Red-Brown Lesion Resistance Gene for Asian Soybean Rust," Crop Science, vol. 47 pp. 829-836 (2007).
International Preliminary Report on Patentability (Chapter II of the Patent Cooperation Treaty) corresponding to International Patent Application No. PCT/US2009/051003 dated Mar. 8, 2011.
Written Opinion of the International Searching Authority, corresponding to International Patent Application No. PCT/US2009/051003 dated Jan. 18, 2011.
International Preliminary Report on Patentability (Chapter 1 of the Patent Cooperation Treaty) corresponding to International Patent Application No. PCT/US2010/021523 dated Aug. 23, 2011.
International Search Report and the Written Opinion of the International Searching Authority, or the Declaration corresponding to International Patent Application No. PCT/US2010/021523 dated Mar. 30, 2010.
Official Action corresponding to U.S. Appl. No. 12/690,782 dated Aug. 21, 2012.
Official Action corresponding to U.S. Appl. No. 12/690,782 dated Apr. 11, 2013.
Official Action corresponding to U.S. Appl. No. 13/054,760 dated Oct. 24, 2012.
Official Action corresponding to U.S. Appl. No. 13/054,760 dated Apr. 23, 2013.
Official Action corresponding to U.S. Appl. No. 12/690,782 dated Oct. 24, 2013.
Ray et al., "Genetics and mapping of adult plant rust resistance in soybean PI 587886 and PI 587880A," Theoretical and Applied Genetics. vol. 119 pp. 271-280 (2009).
Ribeiro et al., "Genetic control of Asian rust in soybean," Euphytica. vol. 157 pp. 15-25 (2007).
Silva et al., "Molecular mapping of two loci that confer resistance to Asian rust in soybean," Theoretical and Applied Genetics. vol. 117 pp. 57-63 (2008).
Twizeyimana et al., "Comparison of field, greenhouse, and detached-leaf evaluations of soybean germplasm for resistance to Phakopsora pachyrhizi," Plant Dis. vol. 91 pp. 1161-1169 (2007).
Zhu et al., "Single-Nucleotide Polymorphisms in Soybean," Genetics. vol. 163 pp. 1123-1134 (2003).
Horsch et al., A simple and general method for transferring genes into plants; Science, (1985) vol. 227:1229-1231.
Brasier, "Phytophthora biodiversity; How many Phytophthora species are there?", Goheen EM, Frankel SJ, eds. Phytophthoras in Forests and Natural Ecosystems.
Glycine max uncharacterized protein At4g04980-like (LOC100799762), mRNA, GenBank Seq XM_006595314.2, Published Nov. 25, 2015.

* cited by examiner

SOY GENE CLUSTER REGIONS AND METHODS OF USE

RELATED APPLICATION INFORMATION

This application is a continuation of U.S. patent application Ser. No. 14/967,716 filed 14 Dec. 2015, which claims the benefit of U.S. Provisional Application No. 61/611,954, filed 16 Mar. 2012, the contents of which are incorporated herein by reference herein.

STATEMENT REGARDING ELECTRONIC SUBMISSION OF A SEQUENCE LISTING

A Sequence Listing in ASCII text format, submitted under 37 C.F.R. § 1.821, entitled 73546-US-REG-D-NAT-1_Sequence_Listing_ST25, 68.9 kb in size, generated on 14 Mar. 2012 and filed via EFS-Web is provided in lieu of a paper copy. This Sequence Listing is hereby incorporated by reference into the specification for its disclosures.

TECHNICAL FIELD

The presently disclosed subject matter relates to markers associated with pathogen resistance and methods of use therefor. More particularly, the presently disclosed subject matter relates to markers that are associated with a particular region of *Glycine* sp. chromosome 13 that is associated with resistance to several different classes of pathogens, and for producing soybean lines with improved resistance to pathogens, the methods involving the use of markers developed from this region in a precision plant breeding program.

BACKGROUND

Plant pathogens are known to cause considerable damage to important crops, resulting in significant agricultural losses with widespread consequences for both the food supply and other industries that rely on plant materials. As such, there is a long felt need to reduce the incidence and/or impact of agricultural pests on crop production.

Several pathogens have been associated with damage to soybeans, which individually and collectively have the potential to cause significant yield losses in the United States and throughout the world. Exemplary such pathogens include, but are not limited to fungi (e.g., genus *Phytophthora*), nematodes (e.g., genus *Meloidogyne*, particularly, *Meloidogyne javanica*), and insects (e.g., aphids). Given the significant threat to food supplies that these pathogens present and the time and expense associated with treating soybean crops to prevent loss, new methods for producing pathogen resistant soybean cultivars are needed.

SUMMARY

This summary lists several embodiments of the presently disclosed subject matter, and in many cases lists variations and permutations of these embodiments.

Thus, it is an object of the presently disclosed subject matter to provide methods for conveying pathogen resistance into non-resistant soybean germplasm, which object is achieved in whole or in part by the presently disclosed subject matter.

BRIEF DESCRIPTION OF THE SEQUENCE LISTING

SEQ ID NOs: 1-35 are nucleotide sequences of the soybean genome comprising single nucleotide polymorphisms (SNPs) identified as being associated with pathogen resistance as set forth in Table 1.

TABLE 1

| SEQ ID NO: | GENBANK® Ref. No. | Nucleotide Positions In Reference to GENBANK® Ref No. |
|---|---|---|
| 1 | NC_016100.1 | 27043783-27044630 |
| 2 | NC_016100.1 | 27043783-27044630 |
| 3 | NC_016100.1 | 27043783-27044630 |
| 4 | NC_016100.1 | 27043783-27044630 |
| 5 | NC_016100.1 | 28451686-28452186 |
| 6 | NC_016100.1 | 28452978-28453478 |
| 7 | NC_016100.1 | 28454463-28454963 |
| 8 | NC_016100.1 | 28544003-28544503 |
| 9 | NC_016100.1 | 28550398-28550898 |
| 10 | NC_016100.1 | 28554784-28555281 |
| 11 | NC_016100.1 | 28673284-28673784 |
| 12 | NC_016100.1 | 28673787-28674287 |
| 13 | NC_016100.1 | 28727753-28728253 |
| 14 | NC_016100.1 | 28795746-28796246 |
| 15 | NC_016100.1 | 28822421-28822921 |
| 16 | NC_016100.1 | 28842751-28843251 |
| 17 | NC_016100.1 | 28869448-28869948 |
| 18 | NC_016100.1 | 28977905-28978405 |
| 19 | NC_016100.1 | 28977987-28978487 |
| 20 | NC_016100.1 | 29065592-29066092 |
| 21 | NC_016100.1 | 29098149-29098649 |
| 22 | NC_016100.1 | 29100447-29100947 |
| 23 | NC_016100.1 | 29156962-29156777 |
| 24 | NC_016100.1 | 29156546-29157046 |
| 25 | NC_016100.1 | 29191313-29191513 |
| 26 | NC_016100.1 | 29191307-29191807 |
| 27 | NC_016100.1 | 29529477-29529674 |
| 28 | NC_016100.1 | 29208269-29208769 |
| 29 | NC_016100.1 | 29224127-29223975 |
| 30 | NC_016100.1 | 29224141-29223980 |
| 31 | NC_016100.1 | 29224141-29223976 |
| 32 | NC_016100.1 | 29273135-29272831 |
| 33 | NC_016100.1 | 31395098-31395273 |
| 34 | NC_016100.1 | 19330494-19330596 |
| 35 | NC_016100.1 | 19943947-19944447 |

SEQ ID NOs 1-35 can be referenced to Soy Chromosome 13 and share high similarity to genome shotgun clone as represented in GENBANK® reference number NC_016100.1.

Nucleotide sequences of oligonucleotide primers that can be employed to amplify and/or otherwise assay (e.g., by one-step and/or two-step PCR-based allelic discrimination assays) subsequences of soybean chromosome 13 that are associated with pathogen resistance loci as set forth in Table 2. TAQMAN®

Assay Primers

TABLE 2

Exemplary Assay Primers and Probes for Genotyping and/or Amplifying Subsequences of SEQ ID NOs: 1-35

| SEQ ID NOs: | KASPar® Assay Primers | | | TAQMAN® Assay Primers | | TAQMAN® Probe Sequences |
|---|---|---|---|---|---|---|
| | Forward Primer 1 | Forward Primer 2 | Reverse Primer | Forward Primers[1] | Reverse Primer[1] | (FAM)/ (VIC/TET) |
| 1 | 36 | 37 | 38 | 129 | 130 | 225/226 |
| 2 | 39 | 40 | 41 | 131 | 132 | 227/228 |
| 3 | 42 | 43 | 44 | 133 | 134 | 229/230 |
| 4 | 45 | 46 | 47 | 135 | 136 | 231/232 |
| 5 | 48 | 49 | 50 | 137 | 138 | 233/234 |
| 6 | 51 | 52 | 53 | | | |
| 7 | 54 | 55 | 56 | | | |
| 8 | 57 | 58 | 59 | 139 | 140 | 235/236 |

TABLE 2-continued

Exemplary Assay Primers and Probes for Genotyping and/or Amplifying Subsequences of SEQ ID NOs: 1-35

| SEQ ID NOs: | KASPar ® Assay Primers | | | TAQMAN ® Assay Primers | | TAQMAN ® Probe Sequences |
| --- | --- | --- | --- | --- | --- | --- |
| | Forward Primer 1 | Forward Primer 2 | Reverse Primer | Forward Primers[1] | Reverse Primer[1] | (FAM)/ (VIC/TET) |
| 9 | 60 | 61 | 62 | | | |
| 10 | 63 | 64 | 65 | | | |
| 11 | 66 | 67 | 68 | | | |
| 12 | 69 | 70 | 71 | | | |
| 13 | 72 | 73 | 74 | | | |
| 14 | 75 | 76 | 77 | 141 | 142 | 237/238 |
| 15 | 78 | 79 | 80 | | | |
| 16 | 81 | 82 | 83 | | | |
| 17 | 84 | 85 | 86 | | | |
| 18 | 87 | 88 | 89 | | | |
| 19 | 90 | 91 | 92 | | | |
| 20 | 93 | 94 | 95 | | | |
| 21 | 96 | 97 | 98 | | | |
| 22 | 99 | 100 | 101 | | | |
| 23 | 102 | 103 | 104 | 143 | 144 | 239/240 |
| 24 | 105 | 106 | 107 | | | |
| 25 | 108 | 109 | 110 | 145 | 146 | 241/242 |
| 26 | 111 | 112 | 113 | | | |
| 27 | 114 | 115 | 116 | | | |
| 28 | 117 | 118 | 119 | | | |
| 29 | 120 | 121 | 122 | | | |
| 30 | 123 | 124 | 125 | | | |
| 31 | 126 | 127 | 128 | | | |
| 32 | | | | 147 | 148 | 243/244 |
| 33 | | | | 149 | 150 | 245/246 |
| 34 | | | | 151 | 152 | 247/248 |
| 35 | | | | 153 | 154 | 249/250 |

[1]The numbers in these columns correspond to the SEQ ID NOs. of the representative oligonucleotide primers. It is understood that the oligonucleotide primers disclosed in Table 2 are exemplary only, and additional oligonucleotide primers can be designed to assay the SNPs at these loci.

With respect to Table 2, for each *Glycine* sp. genomic sequence to be assayed, a TAQMAN® assay (e.g. generally a two-step allelic discrimination assay or similar), a KASP™ assay (generally a one-step allelic discrimination assay defined below or similar), or both can be employed to assay the SNPs as disclosed herein. In an exemplary two-step assay, a forward primer, a reverse primer, and two assay probes (or hybridization oligos) are employed. The forward and reverse primers are employed to amplify subsequences of soybean chromosome 13 that comprise SNPs that are associated with pathogen resistance loci. The particular nucleotides that are present at the SNP positions are then assayed using the assay primers (which in some embodiments are differentially labeled with, for example, fluorophores to permit distinguishing between the two assay probes in a single reaction), which in each pair differ from each other with respect to the nucleotides that are present at the SNP position (although it is noted that in any given pair, the probes can differ in their 5' or 3' ends without impacting their abilities to differentiate between nucleotides present at the corresponding SNP positions). In some embodiments, the assay primers and the reaction conditions are designed such that an assay primer will only hybridize to the reverse complement of a 100% perfectly matched sequence, thereby permitting identification of which allele(s) is/are present based upon detection of hybridizations.

It is noted that the phrase "two-step" does not imply that two separate reaction steps would necessarily have to be performed sequentially in the assay. In some embodiments, the amplification and hybridization steps are performed as a part of the same reaction.

Alternatively or in addition, which nucleotide is present at an SNP position associated with a pathogen resistance locus can be determined using a one-step allelic discrimination assay such as, but not limited to the KASP™ SNP Genotyping System (KBioscience, Beverly, Mass., United States of America). In an exemplary embodiment of this system, allele-specific primers are employed with non-specific upstream or downstream oligonucleotide primers to amplify subsequences of soybean chromosome 13. For any particular SNP, the allele-specific primers differ in their 3'-terminal nucleotides such that each different allele-specific primer can only amplify a subsequence of soybean chromosome 13 if a particular nucleotide is present at the SNP position. For example, the SNP that is present at nucleotide 249 of SEQ ID NO: 1 can be determined using oligonucleotide primers that comprise the sequences set forth as SEQ ID NOs as depicted in Table 2. More particularly, SEQ ID NO: 1 has an SNP at nucleotide position 249. The nucleotide present at this position in the genome of *Glycine* sp. is in some embodiments a C or a T. Oligonucleotide primers that comprise the nucleotide sequences of SEQ ID NOs depicted in Table 2 relative to SEQ ID NO: 1.

In one embodiment of the invention, a minimum identifier can be used in the identification, selection, and confirmation of a plant that will confer a favorable phenotype (e.g. resistance to aphids, RKN and/or phytophthora). "Minimum identifiers" comprise a sequence of 15-20 nucleotide base pairs that enable one to select and/or identify a plant through use of the markers as disclosed herein. It is contemplated that the amplicon could be the minimum identifier (e.g. the 6 nucleotide sequence) or that a minimum identifier for a phenotype of interest could be comprised in a larger sequence (e.g. for instance a amplicon of 25 nucleotide base pairs may in some instaces comprise a 6 base pair minimum identifier). In one embodiment of the invention, these minimum identifiers are useful in selection and/or identification of markers disclosed herein located on soy chromosome 13. One aspect of the invention are minimum identifiers that may be used to identify and/or select plants conferring a favorable phenotype. Table 3 is a listing of minimum identifiers that may be diagnostic for a soy plant in allowing one to identify and/or select for a plant having a favorable phenotype (e.g. resistance to aphids, RKN and/or phytophthora). It is further contemplated and a further embodiment of the invention that reverse compliments of the minimum identifiers in Table 3 may be used as a diagnostic tool in selecting and identifying plants having a favorable phenotype.

TABLE 3

Exemplary Minimum Identifiers for Identyfing and/or Selecting for Plants Conferring a Favorable Phenotype

| Minimum identifier SEQ ID NO: | Diagnostic for SNP Marker comprised in SEQ ID NO: | Phenotype Diagnostic for (+/−) |
| --- | --- | --- |
| 155 | 1 | Aphid (+) |
| 156 | 1 | Aphid (−) |
| 157 | 2 | Aphid (+) |
| 158 | 2 | Aphid (−) |
| 159 | 3 | Aphid (+) |
| 160 | 3 | Aphid (−) |
| 161 | 4 | Aphid (+) |
| 162 | 4 | Aphid (−) |
| 163 | 5 | Aphid (+) |
| 164 | 5 | Aphid (−) |
| 165 | 6 | *Phytophthora*(+) |

TABLE 3-continued

Exemplary Minimum Identifiers for Identyfing and/or Selecting for Plants Conferring a Favorable Phenotype

| Minimum identifier SEQ ID NO: | Diagnostic for SNP Marker comprised in SEQ ID NO: | Phenotype Diagnostic for (+/−) |
|---|---|---|
| 166 | 6 | Phytophthora(−) |
| 167 | 7 | Phytophthora(+) |
| 168 | 7 | Phytophthora(−) |
| 169 | 8 | Aphid (+) |
| 170 | 8 | Aphid (−) |
| 171 | 9 | Phytophthora(+) |
| 172 | 9 | Phytophthora(−) |
| 173 | 10 | Phytophthora(+) |
| 174 | 10 | Phytophthora(−) |
| 175 | 11 | Phytophthora(+) |
| 176 | 11 | Phytophthora(−) |
| 177 | 12 | Aphid (+) |
| 178 | 12 | Aphid (−) |
| 179 | 13 | Phytophthora(+) |
| 180 | 13 | Phytophthora(−) |
| 181 | 14 | Aphid (+) |
| 182 | 14 | Aphid (−) |
| 183 | 15 | Phytophthora(+) |
| 184 | 15 | Phytophthora(−) |
| 185 | 16 | Phytophthora(+) |
| 186 | 16 | Phytophthora(−) |
| 187 | 17 | Phytophthora(+) |
| 188 | 17 | Phytophthora(−) |
| 189 | 18 | Phytophthora(+) |
| 190 | 18 | Phytophthora(−) |
| 191 | 19 | Aphid (+) |
| 192 | 19 | Aphid (−) |
| 193 | 20 | Phytophthora(+) |
| 194 | 20 | Phytophthora(−) |
| 195 | 21 | Phytophthora(+) |
| 196 | 21 | Phytophthora(−) |
| 197 | 22 | Phytophthora(+) |
| 198 | 22 | Phytophthora(−) |
| 199 | 23 | Aphid (+) |
| 200 | 23 | Aphid (−) |
| 201 | 24 | Aphid (+) |
| 202 | 24 | Aphid (−) |
| 203 | 25 | Aphid (+) |
| 204 | 25 | Aphid (−) |
| 205 | 26 | Aphid (+) |
| 206 | 26 | Aphid (−) |
| 207 | 27 | Phytophthora(+) |
| 208 | 27 | Phytophthora(−) |
| 209 | 28 | Aphid (+) |
| 210 | 28 | Aphid (−) |
| 211 | 29 | Aphid (+) |
| 212 | 29 | Aphid (−) |
| 213 | 30 | Aphid (+) |
| 214 | 30 | Aphid (−) |
| 215 | 31 | Aphid (+) |
| 216 | 31 | Aphid (−) |
| 217 | 32 | Aphid (+) |
| 218 | 32 | Aphid (−) |
| 219 | 33 | Aphid (+) |
| 220 | 33 | Aphid (−) |
| 221 | 34 | RKN (+) |
| 222 | 34 | RKN (−) |
| 223 | 35 | RKN (+) |
| 224 | 35 | RKN (−) |

DETAILED DESCRIPTION

The presently disclosed subject matter relates at least in part to the identification of several SNPs associated with pathogen resistance in *Glycine* sp. These SNPs are located within an approximately 4.4 megabase (MB) region of *Glycine* sp. chromosome 13 (Linkage Group F). Provided herein in some embodiments are methods of conveying pathogen resistance into non-resistant soybean germplasm, which employ one or more of the identified SNPs in various approaches.

All references listed below, as well as all references cited in the instant disclosure, including but not limited to all patents, patent applications and publications thereof, scientific journal articles, and database entries (e.g., GEN-BANK® database entries and all annotations available therein) are incorporated herein by reference in their entireties to the extent that they supplement, explain, provide a background for, or teach methodology, techniques, and/or compositions employed herein.

I. General Considerations

A 6 Mb region on chromosome 13 in the soybean genome has been investigated with respect to multiple pathogen resistance genes. Five soybean defense related genes (P21, MMP2, PR1a, RPG1-b, LTCOR11; see Li et al. (2008) *New Phytologist* 179:185-195), two soybean homologous melon defense related genes (*Cucumis melo* NBS-2 (GENBANK® Accession No. AF354505) and *Cucumis melo* NBS-46-7 (GENBANK® Accession No. AF354516) genes), and three soy disease resistance genes (soybean mosaic virus (SMV) resistance genes 3gG2, 5gG3, and 6gG9, corresponding to GENBANK® Accession Nos. AY518517, AY518518, and AY518519, respectively) were selected for Sanger sequencing to identify polymorphisms that are associated with resistance genes and/or resistance gene clusters to aphids, Root Knot Nematode (RKN), *Phytophthora*. Solexa sequence data was also analyzed for similarly associated polymorphisms. 539 polymorphsms were initially identified. 447 polymorphisms identified from the Solexa sequencing data showed an association with aphid resistance. 92 polymorphisms identified from the Sanger sequencing data showed association with aphid, RKN, and *Phytophthora* resistance. A selected set of 127 polymorphisms are being further evaluated for their efficacy.

In another aspect of the invention, a gene cluster region has been identified comprising a large number of markers that may be associated with disease and insect resistance (e.g. Aphid resistance, RKN and or phytoptera resistance in soy) located at physical base positions 19,000,000-32,000,000 bp of the soy chromosome 13 map or equivantly map positions 36-64 cM. Or between SSR markers Satt325-Satt362 as can be deferred from publically available databases as is well known in the art. It is contemplated that genes associated with disease and/or aphid resistance may be present within this gene cluster region. Herein "gene cluster region" refers to a region on soy chromosome 13 having a physical base positions 19,000,000-32,000,000 bp or within the mathematical range of SEQ ID NOs 1-35 as in respect to reference sequence GENBANK® accession number NC_016100.1.

Disclosed herein is the identification and design of markers for SNPs that can be used to identify alleles associated with resistance to several pests and diseases in soybean. Linkage disequilibrium can result in a single SNP or set of SNPs associating with several resistance traits. Marker assisted breeding exploiting these SNPs can enhance conventional breeding in various ways: (i) early selection of traits in the lab before phenotypic expression of traits are observed in the field, subsequently saving time, space and cost, (ii) independence from environmental conditions allows for screening of pest resistant traits any time anywhere, and (iii) stacking genes by incorporating additional pest resistances within a plant. Because of rapid co-evolution of plant pests and plant resistance, tracking these genes with molecular markers can aid in breeding efforts to incorporate these genes.

II. Definitions

Unless defined otherwise, all technical and scientific terms used herein have the same meaning as commonly understood to one of ordinary skill in the art to which the presently disclosed subject matter belongs.

Following long-standing patent law convention, the articles "a", "an", and "the" refer to "one or more" when used in this application, including in the claims. For example, the phrase "a marker" refers to one or more markers. Similarly, the phrase "at least one", when employed herein to refer to an entity, refers to, for example, 1, 2, 3, 4, 5, 6, 7, 8, 9, 10, 15, 20, 25, 30, 35, 40, 45, 50, 75, 100, or more of that entity, including but not limited to whole number values between 1 and 100 and greater than 100.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of mass, weight, time, volume, concentration or percentage is meant to encompass variations of in some embodiments±20%, in some embodiments±10%, in some embodiments±5%, in some embodiments±1%, in some embodiments±0.5%, and in some embodiments±0.1% from the specified amount, as such variations are appropriate to perform the disclosed method.

As used herein, the term "allele" refers to any of one or more alternative forms of a gene, all of which relate to at least one trait or characteristic. In a diploid cell, two alleles of a given gene occupy corresponding loci on a pair of homologous chromosomes, although one of ordinary skill in the art understands that the alleles in any particular individual do not necessarily represent all of the alleles that are present in the species. Since the presently disclosed subject matter relates in some embodiments to SNPs, it is in some instances more accurate to refer to a "haplotype" (i.e., an allele of a chromosomal segment) instead of "allele". However, in such instances, the term "allele" should be understood to comprise the term "haplotype".

As used herein, the term "and/or" when used in the context of a list of entities, refers to the entities being present singly or in combination. Thus, for example, the phrase "A, B, C, and/or D" includes A, B, C, and D individually, but also includes any and all combinations and subcombinations of A, B, C, and D.

As used herein, the phrase "associated with" refers to a recognizable and/or assayable relationship between two entities. For example, a trait, locus, QTL, SNP, gene, marker, phenotype, etc. is "associated with pathogen resistance" if the presence or absence of the trait, locus, QTL, SNP, gene, marker, phenotype, etc., influences an extent or degree of pathogen resistance (e.g., resistance to fungi, nematodes, and/or insects).

In some embodiments, an allele associated with pathogen resistance comprises an allele having a favorable allele associated with a pathogen resistance phenotype as set forth in Table 4.

TABLE 4

Favorable Alleles Associated with Pathogen Resistance Phenotypes

| SEQ ID NO: | SNP Nucleotide Position | Pathogen | Favorable Allele | Unfavorable Allele |
|---|---|---|---|---|
| 1 | 249 | Aphid | A | G |
| 2 | 631 | Aphid | A | T |
| 3 | 710 | Aphid | C | G |
| 4 | 731-732 | Aphid | Del* | Ins* |
| 5 | 251 | Aphid | G | A |
| 6 | 251 | *Phytophthora* | T | C |
| 7 | 251 | *Phytophthora* | C | T |
| 8 | 251 | Aphid | T | C |
| 9 | 251 | *Phytophthora* | G | A |
| 10 | 251 | *Phytophthora* | A | G |
| 11 | 251 | *Phytophthora* | G | T |
| 12 | 251 | Aphid | C | G |
| 13 | 251 | *Phytophthora* | G | A |
| 14 | 251 | Aphid | C | A |
| 15 | 251 | *Phytophthora* | A | G |
| 16 | 251 | *Phytophthora* | A | G |
| 17 | 251 | *Phytophthora* | A | G |
| 18 | 251 | *Phytophthora* | G | A |
| 19 | 251 | Aphid | G | T |
| 20 | 251 | *Phytophthora* | T | C |
| 21 | 251 | *Phytophthora* | T | C |
| 22 | 251 | *Phytophthora* | A | G |
| 23 | 88 | Aphid | G | C |
| 24 | 251 | Aphid | T | A |
| 25 | 101 | Aphid | A | G |
| 26 | 251 | Aphid | C | G |
| 27 | 101 | *Phytophthora* | G | C |
| 28 | 251 | Aphid | A | T |
| 29 | 53 | Aphid | A | T |
| 30 | 62 | Aphid | A | G |
| 31 | 66 | Aphid | A | T |
| 32 | 228 | Aphid | A | T |
| 33 | 51 | Aphid | G | T |
| 34 | 61 | RKN | A | G |
| 35 | 251 | RKN | A | C |

*The polymorphism at nucleotides 731-732 of SEQ ID NO: 4 is an Indel, in which the unfavorable allele has a CA dinucleotide at these positions and the favorable allele has a deletion of the CA dinucleotide. Hence, "Del" indicates that the accession had the deletion at the SNP position and "Ins" indicates that the accession had the CA dinucleotide insertion at the SNP position.
RKN: Root Knot Nematode (i.e., a member of the genus *Meloiddogyne*).

As used herein, the term "backcross", and grammatical variants thereof, refers to a process in which a breeder crosses a progeny individual back to one of its parents, for example, a first generation individual with one of the parental genotypes of the first generation individual. In some embodiments, a backcross is performed repeatedly, with a progeny individual of one backcross being itself backcrossed to the same parental genotype.

The term "chromosome" is used herein in its art-recognized meaning of the self-replicating genetic structure in the cellular nucleus containing the cellular DNA and bearing in its nucleotide sequence the linear array of genes.

The term "comprising", which is synonymous with "including" "containing", or "characterized by", is inclusive or open-ended and does not exclude additional, unrecited elements and/or method steps. "Comprising" is a term of art that means that the named elements and/or steps are present, but that other elements and/or steps can be added and still fall within the scope of the relevant subject matter.

As used herein, the phrase "consisting of" excludes any element, step, or ingredient not specifically recited. For example, when the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of the related disclosure or claim to the specified materials and/or steps, plus those that do not materially affect the basic and novel characteristic(s) of the disclosed and/or claimed subject matter.

With respect to the terms "comprising", "consisting essentially of", and "consisting of", where one of these three terms is used herein, the presently disclosed and claimed subject matter can include the use of either of the other two terms. For example, the presently disclosed subject matter relates in some embodiments to oligonucleotides that comprise specific sequences (e.g., any of SEQ ID NOs: 105-302) that can be employed for assaying the genomes of plants (e.g., soybeans) for the presence of SNPs. It is understood that the presently disclosed subject matter thus also encompasses oligonucleotides that in some embodiments consist essentially of specific sequences that can be employed for assaying the genomes of plants for the presence of SNPs, as well as oligonucleotides that in some embodiments consist of specific sequences (e.g., any of SEQ ID NOs: 36-280) that can be employed for assaying the genomes of plants for the presence of SNPs. Similarly, it is also understood that in some embodiments the methods of the presently disclosed subject matter comprise the steps that are disclosed herein, in some embodiments the methods of the presently disclosed subject matter consist essentially of the steps that are disclosed herein, and in some embodiments the methods of the presently disclosed subject matter consist of the steps that are disclosed herein.

As used herein, the terms "cultivar" and "variety" refer to a group of similar plants that by structural or genetic features and/or performance can be distinguished from other varieties within the same species.

Disclosed herein are exemplary polymorphisms that are associated with increases and decreases in plant resistance to various pathogens (e.g., aphids, RKN, and/or Phytophthora). With respect to the instant disclosure, the phrase "favorable allele" refers in some embodiments to an allele that when present results in a quantitatively higher resistance to one or more pathogens versus the case when the "unfavorable allele" is present. It is noted, however, then in the case where a lower pathogen resistance is desirable, the alleles listed in the instant disclosure (e.g., in Tables 4 and 6-9) as "unfavorable" would in fact be the favorable alleles. As such, the terms "favorable" and "unfavorable" are employed in Tables 4 and 6-9 in the context of increased pathogen resistance, and would be reversed in the context of decreased pathogen resistance.

As used herein, the term "gene" refers to a hereditary unit including a sequence of DNA that occupies a specific location on a chromosome and that contains the genetic instruction for a particular characteristics or trait in an organism.

As used herein, the term "hybrid" in the context of plant breeding refers to a plant that is the offspring of genetically dissimilar parents produced by crossing plants of different lines or breeds or species, including but not limited to the cross between two inbred lines.

As used herein, the term "inbred" refers to a substantially homozygous individual or line.

As used herein, the phrase "informative fragment" refers to a nucleic acid molecule and/or its nucleotide sequence that allows for the proper identification of which allele of an allele set (e.g., an SNP) the nucleic acid molecule and/or the nucleotide sequence corresponds to. For example, whereas the locus that corresponds to SEQ ID NO: 1 comprises a T or a C SNP at position 249 of SEQ ID NO: 1, an "informative fragment" of SEQ ID NO: 1 would be any sequence that comprises position 249 of SEQ ID NO: 1. Similarly, an informative fragment of the same locus that is isolated from a soybean genome that might differ to a degree from SEQ ID NO: 1 could include the nucleotide that corresponds to position 249 of SEQ ID NO: 1, thereby allowing the nucleotide that is present in that position of the differing soybean genome to be determined.

As used herein, the terms "introgression", "introgressed", and "introgressing" refer to both a natural and artificial process whereby genomic regions of one species, variety, or cultivar are moved into the genome of another species, variety, or cultivar, by crossing those species, varieties, or cultivars. The process can optionally be completed by backcrossing to the recurrent parent.

As used herein, the term "linkage" refers to a phenomenon wherein alleles on the same chromosome tend to be transmitted together more often than expected by chance if their transmission was independent. Thus, in some embodiments two alleles on the same chromosome are said to be "linked" when they segregate from each other in the next generation less than 50% of the time, less than 25% of the time, less than 20% of the time, less than 15% of the time, less than 10% of the time, less than 5% of the time, less than 4% of the time, less than 3% of the time, less than 2% of the time, or less than 1% of the time. Thus, two loci are linked if they are within 50, 25, 20, 15, 10, 5, 4, 3, 2, 1, 0.5, or 0.1 centiMorgans (cM) of each other. For example, in some embodiments an SNP is linked to a marker if it is within 50, 25, 20, 15, 10, 9, 8, 7, 6, 5, 4, 3, 2, or 1 cM of the marker.

As used herein, the phrase "linkage group" refers to all of the genes or genetic traits that are located on the same chromosome. Within the linkage group, those loci that are close enough together can exhibit linkage in genetic crosses. Since the probability of crossover increases with the physical distance between loci on a chromosome, loci for which the locations are far removed from each other within a linkage group might not exhibit any detectable linkage in direct genetic tests. The term "linkage group" is mostly used to refer to genetic loci that exhibit linked behavior in genetic systems where chromosomal assignments have not yet been made. Thus, the term "linkage group" is synonymous with the physical entity of a chromosome, although one of ordinary skill in the art will understand that a linkage group can also be defined as corresponding to a region of (i.e., less than the entirety) of a given chromosome.

As used herein, the term "locus" refers to a position that a given gene or a regulatory sequence occupies on a chromosome of a given species.

As used herein, the term "marker" refers to an identifiable position on a chromosome the inheritance of which can be monitored. In some embodiments, a marker comprises a known or detectable nucleic acid sequence.

In some embodiments, a marker corresponds to an amplification product generated by amplifying a *Glycine* sp. nucleic acid with two oligonucleotide primers, for example, by the polymerase chain reaction (PCR). As used herein, the phrase "corresponds to an amplification product" in the context of a marker refers to a marker that has a nucleotide sequence that is the same (allowing for mutations introduced by the amplification reaction itself) as an amplification product that is generated by amplifying *Glycine* sp. genomic DNA with a particular set of primers. In some embodiments, the amplifying is by PCR, and the primers are PCR primers that are designed to hybridize to opposite strands of the *Glycine* sp. genomic DNA in order to amplify a *Glycine* sp. genomic DNA sequence present between the sequences to which the PCR primers hybridize in the *Glycine* sp. genomic DNA. In some embodiments, a marker that "corresponds to"

an amplified fragment is a marker that has the same sequence of one of the strands of the amplified fragment.

As used herein, the term "soybean" refers to a plant, or a part thereof, of the genus Glycine including, but not limited to Glycine max.

As used herein, the phrase "soybean-specific DNA sequence" refers to a polynucleotide sequence having a nucleotide sequence homology of in some embodiments more than 50%, in some embodiments more than 60%, in some embodiments more than 70%, in some embodiments more than 80%, in some embodiments more than 85%, in some embodiments more than 90%, in some embodiments more than 92%, in some embodiments more than 95%, in some embodiments more than 96%, in some embodiments more than 97%, in some embodiments more than 98%, and in some embodiments more than 99% with a sequence of the genome of the species Glycine that shows the greatest similarity to it. In the case of markers for any of the pathogen resistance loci disclosed herein, a "soybean-specific DNA sequence" can comprise a part of the DNA sequence of a soybean genome that flanks and/or is a part of any of the pathogen resistance loci disclosed herein.

As used herein, the phrase "molecular marker" refers to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), insertion and deletion mutations (INDEL), microsatellite markers (SSRs), sequence-characterized amplified regions (SCARs), cleaved amplified polymorphic sequence (CAPS) markers or isozyme markers or combinations of the markers described herein which defines a specific genetic and chromosomal location. A molecular marker "linked to" or "associated with" a pathogen resistance gene or locus as defined herein can thus refer to SNPs, insertion mutations, as well as more usual AFLP markers or any other type of marker used in the field.

As used herein, the phrase "nucleotide sequence homology" refers to the presence of homology between two polynucleotides. Polynucleotides have "homologous" sequences if the sequence of nucleotides in the two sequences is the same when aligned for maximum correspondence. The "percentage of sequence homology" for polynucleotides, such as 50, 60, 70, 80, 90, 95, 98, 99 or 100 percent sequence homology, can be determined by comparing two optimally aligned sequences over a comparison window (e.g., about 20-200 contiguous nucleotides), wherein the portion of the polynucleotide sequence in the comparison window can include additions or deletions (i.e., gaps) as compared to a reference sequence for optimal alignment of the two sequences. Optimal alignment of sequences for comparison can be conducted by computerized implementations of known algorithms, or by visual inspection. Readily available sequence comparison and multiple sequence alignment algorithms are, respectively, the Basic Local Alignment Search Tool (BLAST®; Altschul et al. (1990) *J Mol Biol* 215:403-10; Altschul et al. (1997) *Nucleic Acids Res* 25:3389-3402) and ClustalX (Chenna et al. (2003) *Nucleic Acids Res* 31:3497-3500) programs, both available on the Internet. Other suitable programs include, but are not limited to, GAP, BestFit, PlotSimilarity, and FASTA, which are part of the Accelrys GCG Package available from Accelrys Software, Inc. of San Diego, Calif., United States of America.

As used herein, the term "offspring" plant refers to any plant resulting as progeny from a vegetative or sexual reproduction from one or more parent plants or descendants thereof. For instance, an offspring plant can be obtained by cloning or selfing of a parent plant or by crossing two parent plants and include selfings as well as the F1 or F2 or still further generations. An F1 is a first-generation offspring produced from parents at least one of which is used for the first time as donor of a trait, while offspring of second generation (F2) or subsequent generations (F3, F4, and the like) are specimens produced from selfings or crossings of F1s, F2s and the like. An F1 can thus be (and in some embodiments is) a hybrid resulting from a cross between two true breeding parents (the phrase "true-breeding" refers to an individual that is homozygous for one or more traits), while an F2 can be (and in some embodiments is) an offspring resulting from self-pollination of the F1 hybrids.

As used herein, the phrases "pathogen resistance locus" and "pathogen resistance gene" refer to loci and/or genes that have been associated with pathogen resistance as defined by the markers disclosed herein. For the purposes of the instant disclosure, these loci are said to be present on *Glycine* linkage group F of *Glycine* sp. Chromosome 13, and linked to the markers represented by SEQ ID NOs: 1-35 or within the gene cluster region. Similarly, the phrase "pathogen resistance phenotype" refers to a phenotype the expression of which is influenced by a pathogen resistance locus and/or a pathogen resistance gene.

As used herein, the term "phenotype" refers to a detectable characteristic of a cell or organism, which characteristics are at least partially a manifestation of gene expression. An exemplary phenotype is a pathogen resistance phenotype. Pathogen resistance phenotypes include, but are not limited to aphid resistance, Root Knot Nematode (RKN) resistance, and *Phytophthora* resistance. Phenotyping of soybean accessions with respect to *Phytophthora* resistance and/or aphid resistance was performed as set forth in EXAMPLES 6 and 7 below. Phenotyping of soybean accessions with respect to RKN resistance can be performed using the greenhouse screening procedure described in Tamulonis et al. (1997) *Crop Sci* 37:783-788. For example, seedlings can be inoculated with *Meloidogyne javanica* eggs 7 days after planting. Thirty days later, soil can be gently washed from the roots so that galls can be counted.

As used herein, the phrase "plant part" refers to a part of a plant, including single cells and cell tissues such as plant cells that are intact in plants, cell clumps, and tissue cultures from which plants can be regenerated. Examples of plant parts include, but are not limited to, single cells and tissues from pollen, ovules, leaves, embryos, roots, root tips, anthers, flowers, fruits, stems, shoots, and seeds; as well as scions, rootstocks, protoplasts, calli, and the like.

As used herein, the term "population" refers to a genetically heterogeneous collection of plants that in some embodiments share a common genetic derivation.

As used herein, the term "primer" refers to an oligonucleotide which is capable of annealing to a nucleic acid target and serving as a point of initiation of DNA synthesis when placed under conditions in which synthesis of a primer extension product is induced (e.g., in the presence of nucleotides and an agent for polymerization such as DNA polymerase and at a suitable temperature and pH). A primer (in some embodiments an extension primer and in some embodiments an amplification primer) is in some embodiments single stranded for maximum efficiency in extension and/or amplification. In some embodiments, the primer is an oligodeoxyribonucleotide. A primer is typically sufficiently long to prime the synthesis of extension and/or amplification products in the presence of the agent for polymerization. The minimum lengths of the primers can depend on many factors, including, but not limited to temperature and composition (A/T vs. G/C content) of the primer.

In the context of amplification primers, these are typically provided as a pair of bi-directional primers consisting of one forward and one reverse primer or provided as a pair of forward primers as commonly used in the art of DNA amplification such as in PCR amplification.

As such, it will be understood that the term "primer", as used herein, can refer to more than one primer, particularly in the case where there is some ambiguity in the information regarding the terminal sequence(s) of the target region to be amplified. Hence, a "primer" can include a collection of primer oligonucleotides containing sequences representing the possible variations in the sequence or includes nucleotides which allow a typical base pairing.

Primers can be prepared by any suitable method. Methods for preparing oligonucleotides of specific sequence are known in the art, and include, for example, cloning and restriction of appropriate sequences and direct chemical synthesis. Chemical synthesis methods can include, for example, the phospho di- or tri-ester method, the diethylphosphoramidate method and the solid support method disclosed in U.S. Pat. No. 4,458,066.

Primers can be labeled, if desired, by incorporating detectable moieties by for instance spectroscopic, fluorescence, photochemical, biochemical, immunochemical, or chemical moieties.

The PCR method is well described in handbooks and known to the skilled person. After amplification by PCR, target polynucleotides can be detected by hybridization with a probe polynucleotide which forms a stable hybrid with that of the target sequence under stringent to moderately stringent hybridization and wash conditions. If it is expected that the probes are essentially completely complementary (i.e., about 99% or greater) to the target sequence, stringent conditions can be used. If some mismatching is expected, for example if variant strains are expected with the result that the probe will not be completely complementary, the stringency of hybridization can be reduced. In some embodiments, conditions are chosen to rule out non-specific/adventitious binding. Conditions that affect hybridization, and that select against non-specific binding are known in the art, and are described in, for example, Sambrook & Russell (2001). *Molecular Cloning: A Laboratory Manual, Third Edition*, Cold Spring Harbor Laboratory Press, Cold Spring Harbor, N.Y., United States of America. Generally, lower salt concentration and higher temperature hybridization and/or washes increase the stringency of hybridization conditions.

Continuing, the term "probe" refers to a single-stranded oligonucleotide sequence that will form a hydrogen-bonded duplex with a complementary sequence in a target nucleic acid sequence analyte or its cDNA derivative.

As used herein, the term "quantitative trait locus" (QTL; plural quantitative trait loci; QTLs) refers to a genetic locus (or loci) that controls to some degree a numerically representable trait that, in some embodiments, is continuously distributed. As such, the term QTL is used herein in its art-recognized meaning to refer to a chromosomal region containing alleles (e.g., in the form of genes or regulatory sequences) associated with the expression of a quantitative phenotypic trait. Thus, a QTL "associated with" pathogen resistance refers to one or more regions located in some embodiments on *Glycine* sp. chromosome 13 and/or in linkage group F that includes at least one gene the expression of which influences a level of resistance to one or more pathogens and/or at least one regulatory region that controls the expression of one or more genes involved in pathogen resistance. QTLs can be defined by indicating their genetic location in the genome of a specific *Glycine* sp. accession using one or more molecular genomic markers. One or more markers, in turn, indicate a specific locus. Distances between loci are usually measured by the frequency of crossovers between the loci on the same chromosome (e.g., chromosome 13). The farther apart two loci are, the more likely that a crossover will occur between them. Conversely, if two loci are close together, a crossover is less likely to occur between them. Typically, one centiMorgan (cM) is equal to 1% recombination between loci. When a QTL can be indicated by multiple markers, the genetic distance between the endpoint markers is indicative of the size of the QTL. As used herein, the term "regenerate", and grammatical variants thereof, refers in some embodiments to the production of a plant from tissue culture and use to the production of a plant by growing in soil.

As used herein, the term "resistant" and "resistance" encompass both partial and full resistance to infection with and/or damage by a pathogen (e.g., infection with and/or damage by a pathogenic mold, nematode, or insect). A susceptible plant can either be non-resistant or have lower levels of resistance relative to a resistant plant. The term is used to include such separately identifiable forms of resistance as "full resistance", "immunity", "hypersensitivity", "intermediate resistance", "partial resistance", "tolerance" and "susceptibility".

As used herein, the phrase "stringent hybridization conditions" refers to conditions under which a polynucleotide hybridizes to its target subsequence, typically in a complex mixture of nucleic acids, but to essentially no other sequences. Stringent conditions are sequence-dependent and can be different under different circumstances. Exemplary guidelines for the hybridization of nucleic acids can be found in Tijssen (1993) in *Laboratory Techniques in Biochemistry and Molecular Biology*, Elsevier, New York, N.Y., United States of America; Ausubel et al. (1999) *Short Protocols in Molecular Biology* Wiley, New York, N.Y., United States of America; and Sambrook & Russell, 2001 (supra). Generally, stringent conditions are selected to be about 5-10° C. lower than the thermal melting point (Tm) for the specific sequence at a defined ionic strength pH. The Tm is the temperature (under defined ionic strength, pH, and nucleic acid concentration) at which 50% of the probes complementary to the target hybridize to the target sequence at equilibrium (as the target sequences are present in excess, at Tm, 50% of the probes are occupied at equilibrium). In some embodiments, hybridization conditions are employed (in some embodiments in conjunction with considerations of the nucleotide sequences of the polynucleotides that are intended to hybridize) such that oligonucleotides (such as, but not limited to the forward, reverse, and assay primers listed in Table 2) only hybridize to sequences with which they can form 100% matched duplexes (i.e., the oligonucleotide is 100% identical to the reverse-complement of the sequence to which it hybridizes or includes a 3' sequence that is 100% identical to the reverse-complement of the sequence to which it hybridizes allowing the oligonucleotide to function in an amplification reaction.)

As used herein, the term "susceptible" refers to a plant having no resistance to infection with and/or damage by a pathogen resulting in the plant being affected by the pathogen, in some embodiments resulting in disease symptoms. The term "susceptible" is therefore equivalent to "non-resistant". Alternatively, the term "susceptible" can be employed in a relative context, in which one plant is considered "susceptible" because it is less resistant to infection with and/or damage by a pathogen than is a second plant (which in the context of these terms in a relative usage, would be referred to as the "resistant" plant").

III. Conveying Pathogen Resistance into Non-resistant Germplasm

In some embodiments, the presently disclosed subject matter provides methods for conveying pathogen resistance into non-resistant germplasm (e.g., soybean germplasm). In some embodiments, the presently disclosed methods comprise introgressing pathogen resistance into a non-resistant soybean using one or more nucleic acid markers for marker-assisted breeding among soybean lines to be used in a soybean breeding program, wherein the markers are linked to a pathogen resistance locus present in Linkage Group F of Glycine max associated with any of SEQ ID NOs: 1-35 and/or to minimum identifiers as represented by SEQ ID NOs: 211-280. In some embodiments, the pathogen resistance is resistance to a pathogen selected from among aphids, RKN, and Phytophthora. In some embodiments, the one or more nucleic acid markers are at least 80%, 85%, 90%, 91%, 92%, 93%, 94%, 95%, 96%, 97%, 98%, or 99%, identical to any of SEQ ID NOs: 1-35 and/or to minimum identifiers as represented by SEQ ID NOs: 211-280 over their respective full length.

In some embodiments, the presently disclosed methods further comprise screening an introgressed soybean plant, or a cell or tissue thereof, for pathogen resistance.

The presently disclosed subject matter also provides methods for reliably and predictably introgressing pathogen resistance into non-resistant germplasm (e.g., soybean germplasm) comprising using one or more nucleic acid markers for marker-assisted breeding among soybean lines to be used in a soybean breeding program, wherein the nucleic acid markers are selected from the group consisting of SEQ ID NOs: 1-35 and/or to minimum identifiers as represented by SEQ ID NOs: 211-280, and informative fragments thereof, and introgressing the resistance into the non-resistant soybean germplasm.

The presently disclosed subject matter also provides methods for producing an inbred soybean plant adapted for conferring pathogen resistance in hybrid combination with a suitable second inbred. In some embodiments, the methods comprise (a) selecting a first donor parental line possessing a desired pathogen resistance and having at least one of the resistant locus selected from a locus mapping to Glycine max Linkage Group F between markers mapped by one or more of the markers SEQ ID NOs: 1-35 and/or utilizing minimum identifiers as represented by SEQ ID NOs: 211-280; (b) crossing the first donor parent line with a second parental line in hybrid combination to produce a segregating plant population; (c) screening the segregating plant population for identified chromosomal loci of one or more genes associated with the resistance to one or more pathogens; and (d) selecting plants from the population having the identified chromosomal loci for further screening until a line is obtained which is homozygous for resistance to pathogen at sufficient loci to give resistance to pathogen in hybrid combination. In some embodiments, the pathogen resistance is resistance to a pathogen selected from among aphids, RKN, and Phytophthora.

W. Production of Pathogen-resistant Soybean Plants

As such, in some embodiments the presently disclosed subject matter provides methods for marker-assisted breeding (MAB). The presently disclosed subject matter therefore relates to methods of plant breeding and to methods to select plants, in particular soybean plants, particularly cultivated soybean plants as breeder plants for use in breeding programs or cultivated soybean plants for having desired genotypic or potential phenotypic properties, in particular related to producing valuable soybeans, also referred to herein as commercially valuable plants. Herein, a cultivated plant is defined as a plant being purposely selected or having been derived from a plant having been purposely selected in agricultural or horticultural practice for having desired genotypic or potential phenotypic properties, for example a plant obtained by inbreeding.

The presently disclosed subject matter thus also provides methods for selecting a plant of the genus Glycine exhibiting resistance towards one or more pathogens comprising detecting in the plant the presence of one or more pathogen resistance alleles as defined herein. In an exemplary embodiment of the presently disclosed methods for selecting such a plant, the method comprises providing a sample of genomic DNA from a soybean plant; and (b) detecting in the sample of genomic DNA at least one molecular marker associated with pathogen resistance. In some embodiments, the detecting can comprise detecting one or more SNPs that are associated with pathogen resistance.

The providing of a sample of genomic DNA from a soybean plant can be performed by standard DNA isolation methods well known in the art.

The detecting of a molecular marker can in some embodiments comprise the use of one or more sets of primer pairs that can be used to produce one or more amplification products that are suitable markers for one of the SNPs. Such a set of primers can comprise, in some embodiments, nucleotide sequences as set forth in SEQ ID NOs: 36-280.

In some embodiments, the detecting of a molecular marker can comprise the use of a nucleic acid probe having a base sequence that is substantially complementary to the nucleic acid sequence defining the molecular marker and which nucleic acid probe specifically hybridizes under stringent conditions with a nucleic acid sequence defining the molecular marker. A suitable nucleic acid probe can for instance be a single strand of the amplification product corresponding to the marker. In some embodiments, the detecting of a molecular marker is designed to discriminate whether a particular allele of an SNP is present or absent in a particular plant.

The presently disclosed methods can also include detecting an amplified DNA fragment associated with the presence of a particular allele of an SNP. In some embodiments, the amplified fragment associated with a particular allele of an SNP has a predicted length or nucleic acid sequence, and detecting an amplified DNA fragment having the predicted length or the predicted nucleic acid sequence is performed such that the amplified DNA fragment has a length that corresponds (plus or minus a few bases; e.g., a length of one, two or three bases more or less) to the expected length as based on a similar reaction with the same primers with the DNA from the plant in which the marker was first detected or the nucleic acid sequence that corresponds (i.e., has a homology of in some embodiments more than 80%, in some embodiments more than 90%, in some embodiments more than 95%, in some embodiments more than 97%, and in some embodiments more than 99%) to the expected sequence as based on the sequence of the marker associated with that SNP in the plant in which the marker was first detected. Upon a review of the instant disclosure, one of ordinary skill in the art would appreciate that markers (e.g., SNP alleles) that are absent in resistant plants, while they were present in the susceptible parent(s) (so-called transmarkers), can also be useful in assays for detecting resistance among offspring plants.

The detecting of an amplified DNA fragment having the predicted length or the predicted nucleic acid sequence can be performed by any of a number or techniques, including but not limited to standard gel-electrophoresis techniques or by using automated DNA sequencers. The methods are not described here in detail as they are well known to those of ordinary skill in the art, although exemplary approaches are set forth in the EXAMPLES.

The presently disclosed subject matter thus also relates to methods for producing pathogen-resistant soybean plants comprising detecting the presence of an allele associated with pathogen resistance in a donor soybean plant according to the presently disclosed subject matter as described herein and transferring a nucleic acid sequence comprising at least one allele thus detected, or a pathogen resistance-conferring part thereof, from the donor plant to a pathogen-susceptible recipient soybean plant. The transfer of the nucleic acid sequence can be performed by any of the methods described herein.

An exemplary embodiment of such a method comprises the transfer by introgression of the nucleic acid sequence from a pathogen-resistant donor soybean plant into a pathogen-susceptible recipient soybean plant by crossing the plants. This transfer can thus suitably be accomplished by using traditional breeding techniques. Pathogen-resistance loci are introgressed in some embodiments into commercial soybean varieties using marker-assisted selection (MAS) or marker-assisted breeding (MAB). MAS and MAB involves the use of one or more of the molecular markers for the identification and selection of those offspring plants that contain one or more of the genes that encode for the desired trait. In the context of the presently disclosed subject matter, such identification and selection is based on selection of SNP alleles of the presently disclosed subject matter or markers associated therewith. MAB can also be used to develop near-isogenic lines (NIL) harboring one or more pathogen resistant alleles of interest, allowing a more detailed study of an effect of such allele(s), and is also an effective method for development of backcross inbred line (BIL) populations. Soybean plants developed according to these embodiments can in some embodiments derive a majority of their traits from the recipient plant, and derive pathogen resistance from the donor plant.

As discussed herein, traditional breeding techniques can be used to introgress a nucleic acid sequence associated with pathogen resistance into a pathogen-susceptible recipient soybean plant. For example, inbred pathogen-resistant soybean plant lines can be developed using the techniques of recurrent selection and backcrossing, selfing, and/or dihaploids, or any other technique used to make parental lines. In a method of recurrent selection and backcrossing, pathogen resistance can be introgressed into a target recipient plant (the recurrent parent) by crossing the recurrent parent with a first donor plant, which differs from the recurrent parent and is referred to herein as the "non-recurrent parent". The recurrent parent is a plant that is non-resistant or has a low level of resistance to pathogens and, in some embodiments, possesses commercially desirable characteristics, such as, but not limited to (additional) disease and/or insect resistance, valuable nutritional characteristics, valuable abiotic stress tolerance (including, but not limited to drought tolerance), and the like. In some embodiments, the non-recurrent parent exhibits pathogen resistance and comprises a nucleic acid sequence that is associated with pathogen resistance. The non-recurrent parent can be any plant variety or inbred line that is cross-fertile with the recurrent parent.

In some embodiments, the progeny resulting from a cross between the recurrent parent and non-recurrent parent are backcrossed to the recurrent parent. The resulting plant population is then screened for the desired characteristics, which screening can occur in a number of different ways. For instance, the population can be screened using phenotypic pathology screens or quantitative bioassays as known in the art. Alternatively, instead of using bioassays, MAB can be performed using one or more of the hereinbefore described molecular markers, hybridization probes, or polynucleotides to identify those progeny that comprise a nucleic acid sequence encoding pathogen resistance. Also, MAB can be used to confirm the results obtained from the quantitative bioassays. In some embodiments, the markers defined herein are suitable to select proper offspring plants by genotypic screening.

Following screening, the F1 hybrid plants that exhibit a pathogen-resistant phenotype or, in some embodiments genotype, and thus comprise the requisite nucleic acid sequence associated with pathogen resistance, are then selected and backcrossed to the recurrent parent for a number of generations in order to allow for the soybean plant to become increasingly inbred. This process can be performed for two, three, four, five, six, seven, eight, or more generations. In principle, the progeny resulting from the process of crossing the recurrent parent with the pathogen-resistant non-recurrent parent are heterozygous for one or more genes that encode pathogen resistance.

In general, a method of introducing a desired trait into a hybrid soybean variety can comprise:
  (a) crossing an inbred soybean parent with another soybean plant that comprises one or more desired traits, to produce F1 progeny plants, wherein the desired trait is pathogen resistance;
  (b) selecting the F1 progeny plants that have the desired trait to produce selected F1 progeny plants, in some embodiments using molecular markers as defined herein;
  (c) backcrossing the selected progeny plants with the inbred soybean parent plant to produce backcross progeny plants;
  (d) selecting for backcross progeny plants that have the desired trait and morphological and physiological characteristics of the inbred soybean parent plant, wherein the selection comprises the isolation of genomic DNA and testing the DNA for the presence of at least one molecular marker for pathogen resistance, in some embodiments as described herein;
  (e) repeating steps (c) and (d) two or more times in succession to produce selected third or higher backcross progeny plants;
  (f) optionally selfing selected backcross progeny in order to identify homozygous plants; and
  (g) crossing at least one of the backcross progeny or selfed plants with another soybean parent plant to generate a hybrid soybean variety with the desired trait and all of the morphological and physiological characteristics of hybrid soybean variety when grown in the same environmental conditions.

As indicated, the last backcross generation can be selfed in order to provide for homozygous pure breeding (inbred) progeny for pathogen resistance. Thus, a result of recurrent selection, backcrossing, and/or selfing can be the production of lines that are genetically homogenous for the alleles associated with pathogen resistance, and in some embodiments as well as for other loci associated with traits of commercial interest.

V. Molecular Markers and SNPs

Molecular markers are used for the visualization of differences in nucleic acid sequences. This visualization can be due to DNA-DNA hybridization techniques after digestion with a restriction enzyme (e.g., an RFLP) and/or due to techniques using the polymerase chain reaction (e.g., STS, SSR/microsatellites, AFLP, and the like). In some embodiments, all differences between two parental genotypes segregate in a mapping population based on the cross of these parental genotypes. The segregation of the different markers can be compared and recombination frequencies can be calculated. Methods for mapping markers in plants are disclosed in, for example, Glick & Thompson (1993) *Methods in Plant Molecular Biology and Biotechnology*, CRC Press, Boca Raton, Fla., United States of America; Zietkiewicz et al. (1994) Genomics 20:176-183.

The recombination frequencies of molecular markers on different chromosomes and/or in different linkage groups are generally 50%. Between molecular markers located on the same chromosome or in the same linkage group, the recombination frequency generally depends on the physical distance between the markers on a chromosome. A low recombination frequency typically corresponds to a low genetic distance between markers on a chromosome. Comparing all recombination frequencies among a set of molecular markers results in the most logical order of the molecular markers on the chromosomes or in the linkage groups. This most logical order can be depicted in a linkage map. A group of adjacent or contiguous markers on the linkage map that is associated with an increased level of resistance to a disease; e.g., to a reduced incidence of acquiring the disease upon infectious contact with the disease agent and/or a reduced lesion growth rate upon establishment of infection, can provide the position of a locus associated with resistance to that disease.

The markers disclosed herein can be used in various aspects of the presently disclosed subject matter as set forth herein. Aspects of the presently disclosed subject matter are not to be limited to the use of the markers identified herein, however. It is stressed that the aspects can also make use of markers not explicitly disclosed herein or even yet to be identified.

The markers provided by the presently disclosed subject matter can be used for detecting the presence of one or more pathogen resistance alleles of the presently disclosed subject matter in a suspected pathogen-resistant soybean plant, and can therefore be used in methods involving marker-assisted breeding and selection of pathogen-resistant soybean plants. In some embodiments, detecting the presence of a particular allele of an SNP of the presently disclosed subject matter is performed with at least one of the markers for the resistance loci defined herein. The presently disclosed subject matter therefore relates in another aspect to a method for detecting the presence of a particular allele associated with pathogen resistance, comprising detecting the presence of a nucleic acid sequence of the SNP in a suspected pathogen-resistant soybean plant, which presence can be detected by the use of the disclosed markers and oligonucleotides.

The nucleotide sequence of an SNP of the presently disclosed subject matter can for instance be resolved by determining the nucleotide sequence of one or more markers associated with the SNP and designing internal primers for the marker sequences that can be used to determine which allele of the SNP is present in the plant.

In embodiments of such methods for detecting the presence of an SNP in a suspected pathogen-resistant soybean plant, the method can also comprise providing a oligonucleotide or polynucleotide capable of hybridizing under stringent hybridization conditions to a particular nucleic acid sequence of an SNP, in some embodiments selected from the SNPs disclosed herein, contacting the oligonucleotide or polynucleotide with genomic nucleic acid (or a fragment thereof, including, but not limited to a restriction fragment thereof) of a suspected pathogen-resistant soybean plant, and determining the presence of specific hybridization of the oligonucleotide or polynucleotide to the genomic nucleic acid (or the fragment thereof).

In some embodiments, the method is performed on a nucleic acid sample obtained from the suspected pathogen-resistant soybean plant, although in situ hybridization methods can also be employed. Alternatively, one of ordinary skill in the art can design specific hybridization probes or oligonucleotides capable of hybridizing under stringent hybridization conditions to the nucleic acid sequence of the allele associated with pathogen resistance and can use such hybridization probes in methods for detecting the presence of an SNP allele disclosed herein in a suspected pathogen-resistant soybean plant.

VI. Pathogen-resistant Soybean Plants, and Seeds and Parts therefrom

The development of a hybrid soybean variety in a soybean plant breeding program can, in some embodiments, involve three steps: (1) the selection of plants from various germplasm pools for initial breeding crosses; (2) the selfing of the selected plants from the breeding crosses for several generations to produce a series of inbred lines, which, individually breed true and are highly uniform; and (3) crossing a selected variety with an different variety to produce the hybrid progeny (F1). After a sufficient amount of inbreeding successive filial generations will merely serve to increase seed of the developed inbred. In some embodiments, an inbred line comprises homozygous alleles at about 95% or more of its loci.

As such, pathogen-resistant soybean plants or parts thereof, obtainable by the methods of the presently disclosed subject matter, are aspects of the presently disclosed subject matter.

The pathogen-resistant soybean plants of the presently disclosed subject matter, or part thereof, can be heterozygous or homozygous for the resistance traits (in some embodiments, homozygous). Although the pathogen resistance loci of the presently disclosed subject matter, as well as resistance-conferring subsequences thereof, can be transferred to any plant in order to provide for a pathogen-resistant plant, the methods and plants of the presently disclosed subject matter are in some embodiments related to plants of the genus *Glycine*.

Another aspect of the presently disclosed subject matter relates to a method of producing seeds that can be grown into pathogen-resistant soybean plants. In some embodiments, the method comprises providing a pathogen-resistant soybean plant of the presently disclosed subject matter, crossing the pathogen-resistant plant with another soybean plant, and collecting seeds resulting from the cross, which when planted, produce pathogen-resistant soybean plants.

As such, the methods of the presently disclosed subject matter can in some embodiments comprise providing a pathogen-resistant soybean plant of the presently disclosed subject matter, crossing the pathogen-resistant plant with a soybean plant, collecting seeds resulting from the cross, regenerating the seeds into plants, selecting pathogen-resistant plants by any of the methods described herein, self-pollinating the selected plants for a sufficient number of generations to obtain plants that are fixed for an allele associated with pathogen-resistance in the plants, backcrossing the plants thus produced with soybean plants having desirable phenotypic traits for a sufficient number of generations to obtain soybean plants that are pathogen-resistant and have desirable phenotypic traits, and collecting the seeds produced from the plants resulting from the last backcross, which when planted, produce soybean plants which are pathogen-resistant.

Thus, in some embodiments the presently disclosed subject matter provides methods for selecting pathogen-resistant soybean plants. In some embodiments, the methods comprise (a) genotyping one or more soybean plants with respect to one or more single nucleotide polymorphisms (SNPs), wherein the one or more SNPs are present within one or more molecular markers selected from the group consisting of SEQ ID NOs: 1-35 and/or to minimum identifiers as represented by SEQ ID NOs: 211-280, and informative fragments thereof; and (b) selecting a soybean plant that includes at least one resistance allele associated with the SNPs, thereby selecting a pathogen resistant soybean plant. In some embodiments, the at least one resistance allele is associated with an allele having:
  (i) an A at nucleotide 249 of SEQ ID NO: 1; an A at nucleotide 631 of SEQ ID NO: 2; a C at nucleotide 710 of SEQ ID NO: 3; a deletion of nucleotides 731 and 732 of SEQ ID NO: 4; a C at nucleotide 251 of SEQ ID NO: 12; a C at nucleotide 251 of SEQ ID NO: 14; a G at nucleotide 251 of SEQ ID NO: 19; a G at nucleotide 88 of SEQ ID NO: 23; a T at nucleotide 251 of SEQ ID NO: 24; an A at nucleotide 101 of SEQ ID NO: 25; a C at nucleotide 251 of SEQ ID NO: 26; an A at nucleotide 251 of SEQ ID NO: 28; an A at nucleotide 53 of SEQ ID NO: 29; an A at nucleotide 62 of SEQ ID NO: 30; an A at nucleotide 66 of SEQ ID NO: 31; an A at nucleotide 228 of SEQ ID NO: 32; and/or a G at nucleotide 51 of SEQ ID NO: 33, and that is associated with aphid resistance;
  (ii) a A at nucleotide 61 of SEQ ID NO: 34; and/or a A at nucleotide 251 of SEQ ID NO: 35; a G at nucleotide of 251 SEQ ID NO: 7, and that is associated with RKN resistance; and/or
  (iii) a T at nucleotide 251 of SEQ ID NO: 6; a C at nucleotide 251 of SEQ ID NO: 7; a G at nucleotide 251 of SEQ ID NO: 9; an A at nucleotide 251 of SEQ ID NO: 10; a G at nucleotide 251 of SEQ ID NO: 11; a G at nucleotide 251 of SEQ ID NO: 13; an A at nucleotide 251 of SEQ ID NO: 15; an A at nucleotide 251 of SEQ ID NO: 16; an A at nucleotide 251 of SEQ ID NO: 17; a G at nucleotide 251 of SEQ ID NO: 18; a T at nucleotide 251 of SEQ ID NO: 20; a T at nucleotide 251 of SEQ ID NO: 21; an A at nucleotide 251 of SEQ ID NO: 22; a C at nucleotide 101 of SEQ ID NO: 27, and that is associated with *Phytophthora* resistance.

The presently disclosed subject matter also provides methods for selecting pathogen resistant soybean plants comprising (a) isolating one or more nucleic acids from a plurality of soybean plants; (b) detecting in said isolated nucleic acids the presence of one or more marker molecules associated with pathogen resistance, wherein each of said one or more marker molecules comprises a nucleotide sequence that is at least 85% identical to one of SEQ ID NOs: 1-35 and/or to minimum identifiers as represented by SEQ ID NOs: 211-280, informative fragments thereof, and any marker molecule mapped within 1, 2, 3, 4, 5, 6, 7, 8, 9, or 10 centiMorgans or less from said marker molecules; and (c) selecting a soybean plant comprising said one or more marker molecules, thereby selecting a pathogen resistant soybean plant. In some embodiments, the pathogen resistance is resistance to a pathogen selected from among aphids, RKN, and *Phytophthora*. In some embodiments, each of said one or more marker molecules comprises a nucleotide sequence comprising:
  (i) an A at nucleotide 249 of SEQ ID NO: 1; an A at nucleotide 631 of SEQ ID NO: 2; a C at nucleotide 710 of SEQ ID NO: 3; a deletion of nucleotides 731 and 732 of SEQ ID NO: 4; a C at nucleotide 251 of SEQ ID NO: 12; a C at nucleotide 251 of SEQ ID NO: 14; a G at nucleotide 251 of SEQ ID NO: 19; a G at nucleotide 88 of SEQ ID NO: 23; a T at nucleotide 251 of SEQ ID NO: 24; an A at nucleotide 101 of SEQ ID NO: 25; a C at nucleotide 251 of SEQ ID NO: 26; an A at nucleotide 251 of SEQ ID NO: 28; an A at nucleotide 53 of SEQ ID NO: 29; an A at nucleotide 62 of SEQ ID NO: 30; an A at nucleotide 66 of SEQ ID NO: 31; an A at nucleotide 228 of SEQ ID NO: 32; and/or a G at nucleotide 51 of SEQ ID NO: 33, and that is associated with aphid resistance;
  (ii) a A at nucleotide 61 of SEQ ID NO: 34; and/or a A at nucleotide 251 of SEQ ID NO: 35; a G at nucleotide of 251 SEQ ID NO: 7, and that is associated with RKN resistance; and/or
  (iii) a T at nucleotide 251 of SEQ ID NO: 6; a C at nucleotide 251 of SEQ ID NO: 7; a G at nucleotide 251 of SEQ ID NO: 9; an A at nucleotide 251 of SEQ ID NO: 10; a G at nucleotide 251 of SEQ ID NO: 11; a G at nucleotide 251 of SEQ ID NO: 13; an A at nucleotide 251 of SEQ ID NO: 15; an A at nucleotide 251 of SEQ ID NO: 16; an A at nucleotide 251 of SEQ ID NO: 17; a G at nucleotide 251 of SEQ ID NO: 18; a T at nucleotide 251 of SEQ ID NO: 20; a T at nucleotide 251 of SEQ ID NO: 21; an A at nucleotide 251 of SEQ ID NO: 22; a C at nucleotide 101 of SEQ ID NO: 27, and that is associated with *Phytophthora* resistance.

The presently disclosed subject matter also provides pathogen resistant soybean plants selected using the presently disclosed methods, or a cell, tissue culture, seed thereof. In some embodiments, the presently disclosed subject matter provides methods for producing seeds that generate soybean plants resistant to a pathogen. In some embodiments, the methods comprise (a) providing a Glycine max plant which contains one or more alleles that confer resistance to one or more pathogens, which alleles are associated with a pathogen resistance locus present in Linkage Group F of *Glycine* max associated with any of SEQ ID NOs: SEQ ID NOs: 1-35 and/or to minimum identifiers as represented by SEQ ID NOs: 211-280, wherein: (i) the pathogen resistance locus is an aphid resistance locus that is defined by one or more of the following aphid resistance markers: an aphid resistance marker of about 504 bp as set forth in SEQ ID NO: 1; an aphid resistance marker of about 848 bp as set forth in SEQ ID NO: 2; an aphid resistance marker of about 848 bp as set forth in SEQ ID NO: 3; an aphid resistance marker of about 848 bp as set forth in SEQ ID NO: 4; an aphid resistance marker of about 501 bp as set forth in SEQ ID NO: 12; an aphid resistance marker of about 501 bp as set forth in SEQ ID NO: 14; an aphid resistance marker of about 501 bp as set forth in SEQ ID NO: 19; an aphid resistance marker of about 187 bp as set forth in SEQ ID NO: 23; an aphid resistance marker of about 501 bp as set forth in SEQ ID NO: 24; an aphid resistance marker of about 201 bp as set forth in SEQ ID NO: 25; an aphid resistance marker of about 501 bp as set forth in SEQ ID NO: 26; an aphid resistance marker of about 501 bp as set forth in SEQ ID NO: 28; an aphid resistance marker of about 153 bp as set forth in SEQ ID NO: 29; an aphid resistance marker of about 161 bp as set forth in SEQ ID NO: 30; an aphid resistance marker of about 165 bp as set forth in SEQ ID NO: 31; an aphid resistance marker of about 251 bp as set forth in SEQ ID NO: 32; and/or an aphid resistance marker of about 179 bp as set forth in SEQ ID NO: 33; or any part of a DNA sequence linked within 1, 2, 5, or 10 cM to at least one of these markers conferring resistance to aphids; (ii) the pathogen resistance locus is an RKN resistance locus that is defined by one or more of the following RKN resistance markers: an RKN resistance marker of about 501 bp as set forth in SEQ ID NO: 5; an RKN resistance marker of about 501 bp as set forth in SEQ ID NO: 34; an RKN resistance marker of about 501 bp as set forth in SEQ ID NO:35, or any part of a DNA sequence linked within 1, 2, 5, or 10 cM to at least one of these markers conferring resistance to RKN; and/or (iii) the pathogen resistance locus is a *Phytophthora* resistance locus that is defined by one or more of the following *Phytophthora* resistance markers: a *Phytophthora* resistance marker of about 501 bp as set forth in SEQ ID NO: 6; a *Phytophthora* resistance marker of about 501 bp as set forth in SEQ ID NO: 7; a *Phytophthora* resistance marker of about 501 bp as set forth in SEQ ID NO: 9; a *Phytophthora* resistance marker of about 501 bp as set forth in SEQ ID NO: 10; a *Phytophthora* resistance marker of about 501 bp as set forth in SEQ ID NO: 11; a *Phytophthora* resistance marker of about 501 bp as set forth in SEQ ID NO: 13; a *Phytophthora* resistance marker of about 501 bp as set forth in SEQ ID NO: 15; a *Phytophthora* resistance marker of about 501 bp as set forth in SEQ ID NO: 16; a *Phytophthora* resistance marker of about 501 bp as set forth in SEQ ID NO: 17; a *Phytophthora* resistance marker of about 501 bp as set forth in SEQ ID NO: 18; a *Phytophthora* resistance marker of about 501 bp as set forth in SEQ ID NO: 20; a *Phytophthora* resistance marker of about 501 bp as set forth in SEQ ID NO: 21; a *Phytophthora* resistance marker of about 501 bp as set forth in SEQ ID NO: 22; a *Phytophthora* resistance marker of about 201 bp as set forth in SEQ ID NO: 27, or any part of a DNA sequence linked within 1, 2, 5, or 10 cM to at least one of these markers conferring resistance to *Phytophthora*; (b) crossing the *Glycine* max plant provided in step (a) with *Glycine* max culture breeding material; and (c) collecting seeds resulting from the cross in step (b) that result in soybean plants which are resistant to pathogen.

In some embodiments, the presently disclosed methods further comprise detecting at least one allelic form of a single nucleotide polymorphism (SNP) associated with at least one of the one or more alleles that confer resistance to pathogen. For example, the detecting can comprise amplifying the marker locus or a portion of the marker locus and detecting the resulting amplified marker amplicon. In some embodiments, the amplifying comprises (a) admixing an amplification primer or amplification primer pair with a nucleic acid isolated from the first *Glycine* max plant or germplasm, wherein the primer or primer pair is complementary or partially complementary to at least a portion of the marker locus, and is capable of initiating DNA polymerization by a DNA polymerase using the soybean nucleic acid as a template; and (b) extending the primer or primer pair in a DNA polymerization reaction comprising a DNA polymerase and a template nucleic acid to generate at least one amplicon. The nucleic acid that is amplified can be selected from DNA and RNA. In some embodiments, the amplifying comprises employing a polymerase chain reaction (PCR) or ligase chain reaction (LCR) using a nucleic acid isolated from the first soybean plant or germplasm as a template in the PCR or LCR.

In one aspect of the invention one may select or identify a soybean plant having increased pathogen resistance utilizing the minimum identifiers depicted in Table 3. In another aspect a soybean plant comprising at least one to two of the minimum identifiers as depicted in Table 3 is contemplated. In another aspect a soybean plant that may be identifie having 2 or more of the minimum identifiers described in Table 3, wherein the plant confers increased resistance to plant pathogens can be useful in various aspects of the invention. In one aspect a plant identified using 2 or more minimum identifiers as depicted in Table 3 may be useful in various aspects of the invention The presently disclosed subject matter also provides improved soybean plants, seeds, and/or tissue cultures produced by the presently disclosed methods.

The presently disclosed subject matter also provides introgressed *Glycine* max plants and/or germplasm produced by the presently disclosed methods.

VI. Compositions

In some embodiments, the presently disclosed subject matter provides methods for analyzing the genomes of plants to identify those that include favorable markers associated with pathogen resistance. In some embodiments, the analysis methods comprise amplifying subsequences of the genomes of the plants and determining the nucleotides present in one, some, or all positions of the amplified subsequences.

Thus, in some embodiments the presently disclosed subject matter provides compositions comprising one or more amplification primer pairs capable of initiating DNA polymerization by a DNA polymerase on a *Glycine* max nucleic acid template to generate a *Glycine* max marker amplicon. In some embodiments, the *Glycine* max marker amplicon corresponds to *Glycine* max marker comprising a nucleotide sequence of any of SEQ ID NOs: 1-35 and/or to minimum identifiers as represented by SEQ ID NOs: 211-280. In view of the disclosure of SEQ ID NOs: 1-35 and/or to minimum identifiers as represented by SEQ ID NOs: 211-280 as being linked to pathogen resistance loci, one of ordinary skill in the art would be aware of various techniques that could be employed to analyze the sequences of the corresponding soybean nucleic acids. Representative amplification primer pairs can comprise the nucleotide sequences of a forward primer and corresponding reverse primer as set forth hereinabove in Table 2.

EXAMPLES

The following Examples provide illustrative embodiments. In light of the present disclosure and the general level of skill in the art, those of skill will appreciate that the following Examples are intended to be exemplary only and that numerous changes, modifications, and alterations can be employed without departing from the scope of the presently claimed subject matter.

Introduction to the Examples

Nucleotide sequences from five (5) soybean defense-related genes (P21, MMP2, PR1a, RPG1-b, and LTCOR11), two (2) melon defense-related genes (GENBANK® Accession Nos. AF354505 and AF354516), and three (3) soybean mosaic virus (SMV) resistance genes (GENBANK® Accession Nos. AY518517, AY518518, and AY518519) were BLAST®ed against the 8× Soybean Genome Database (i.e., the "Phytozome" Database administered by the Joint Genome Institute and the Center for Integrative Genomics available through the World Wide Web; see also Schmutz et al. (2010) *Nature* 463:178-183). Sequence homologies of short spans of sequence (<100 bp) were found throughout the genome. Interestingly, homologies were found to the full length sequences of certain of these genes, and of those, several showed homology to sequences within a span of approx 6 Mb on Linkage Group F (Chromosome 13). The EXAMPLES set forth herein below describe the further analysis of these genes.

Example 1

Sanger Sequencing

A set of 28 soybean lines representing sensitivity and resistance to several soybean biotic stresses were selected as lines to be used in the sequencing panel. These lines were either resistant or sensitive to aphids, RKN, and/or *Phytophthora*. Table 5 summarizes the soybean varieties employed and their respective stress resistances.

TABLE 5

SNP Screening Panel

| Line* | Resistance |
|---|---|
| *Phytophthora* | |
| Soybean 1 with-*Phytophthora* | susceptible |
| Soybean 2 with-*Phytophthora* | susceptible |
| Soybean 3 with *Phytophthora* | susceptible |
| Soybean 4 with-*Phytophthora* | susceptible |
| Soybean 5 with-*Phytophthora* | susceptible |
| Soybean 6-*Phytophthora* | susceptible |
| Soybean 7 *Phytophthora* | susceptible |
| Soybean 8-*Phytophthora* | susceptible |
| Soybean 9 *Phytophthora* | susceptible |
| S32-N9-*Phytophthora* Rps8 | resistant |
| Aphid | |
| Loda | Susceptible |
| WILLIAMS 82 | Susceptible |
| Ina | Susceptible |
| Dwight | susceptible |
| Sugao Zarai | resistant |
| Sennari | resistant |

*Soybean Lines 1-9 lack Rps8 and are designated as susceptible
[1] Germplasm Resources Information Network, Agricultural Research Service, United States Department of Agriculture, Beltsville, Maryland, United States of America.

Example 2

TAQMAN® Validation

To validate TAQMAN® allelic discrimination assays for association with pathogen resistance or tolerance, plants were selected based on their known phenotypic status and compared to the genotype at the specific SNP location. DNA isolated from leaf tissue of seedlings 7-10 days after planting was diluted in TE buffer and stored at 4° C. until used in PCR reactions as described below.

PCR was set up in 800 nl final volumes using the NEXAR® ARRAY TAPE™ Instrumentation (Douglas Scientific, Alexandria, Minn., United States of America). Approximately 5 ng leaf tissue DNA was added to each well and dried. Each well then received 1× Master Mix (JUMP-START™ Taq READYMIX™ Sigma Catalogue No. 2893; Sigma Chemical Co., St. Louis, Mo., United States of America), supplemented with 1.5 mM MgCl2 and 0.3 µM Sulforhodamine 101 (ROX) reference dye solution (Sigma Catalogue No. S-7635; Sigma Chemical Co., St. Louis, Mo., United States of America), and 0.5×TaqMan primers and probes (primers: 11.25 nM, probes: 2.5 nM).

The wells of the array tape were sealed and placed in a Duncan DT-24 water bath thermal cycler (KBioscience, Inc.). The cycling program was as follows: 95° C. for 10 minutes for initial denaturation, followed by 40 cycles of 95° C. for 15 seconds, 60° C. for 1 minute. Fluorescence generated during thermal cycling was measured on an ARAYA® scanning unit (Douglas Scientific). Allele calls were made using software that plots FAM vs. TET fluorescence. Samples that amplified one probe (i.e., generated only FAM fluorescence or TET fluorescence) were adjudged to be homozygous for the corresponding allele. Samples which amplified both FAM and TET probes were scored as heterozygous.

Example 3

Genotyping Soybean Accessions with Respect to Aphid Resistance

Phenotyping of soybean accessions with respect to aphid resistance was performed using the following protocol: ten seeds of each soybean line were planted (two reps of five seeds each in an "X" pattern (one seed at each "end" of the "X" and one in the center)). The pots were arranged to minimize any neighbor-entry effect. One pot of aphid-susceptible/negative and one of aphid-resistant/positive checks was placed after about every 50 entries. These were planted in the same 5-seed "X" arrangement. The seedlings were infested 6-10 days after planting (DAP) at growth stage VC (large, open unifoliates) with about 5-15 aphids each. Greenhouses were maintained at about 80° F. (light hours) or 70° F. (dark hours), with 16 hours of light and 8 hours of dark per 24 hours. Ratings were at 15-30 days after infestation (DAI), depending on the progress of aphid development on the negative/susceptible checks. Entries that rated 1-3.5 were categorized as "resistant" and those that rate 3.6-6 were characterized as susceptible using the ratings scale in Table 5 below.

TABLE 6

Ratings Scale for Scoring Aphid Susceptibility/Resistance

| Rating Scale | Description | Estimated Aphid Populations |
|---|---|---|
| 1 | No aphids or very few wanderers | 0-5 |
| 2 | very few established/wanderers | 6-9 |
| 3 | "moderate" number on stems or leaves; might be colonized | 10-49 |
| 4 | well established on stems or leaves | 50-99 |
| 5 | well established on stems and leaves | 100-249 |
| 6 | very heavy infestation on stems and leaves | >250 |
| ng | no germination | |

The alleles present at SNP positions for various of soybean accessions scored as resistant or susceptible with respect to aphids are presented in Tables 6 and 7.

TABLE 7

Detailed SNP Genotyping Data Related to Aphid Resistance
As Determined by TAQMAN ® Assays

| | | | | | | |
|---|---|---|---|---|---|---|
| Favorable | | A | A | C | Del | G |
| Unfavorable | | G | T | G | Ins | A |
| PI | Accession Name | SEQ ID NO: 1 SNP | SEQ ID NO: 2 SNP | SEQ ID NO: 3 SNP | SEQ ID NO: 4 SNP | SEQ ID NO: 5 SNP |
| Resistant Accessions | | | | | | |
| PI243540 (resistant) | Sennari | A | A | C | Het | A |
| PI200538 (resistant) | Sugao Zarai | A | T | C | Del | G |
| Susceptible Accessions | | | | | | |
| M03256* | | G | T | G | Ins | A |
| CL968413** | | G | T | G | Ins | A |
| Susceptible Soybean1 | N/A | G | T | G | Ins | A |
| PI606749 | Ina | G | T | G | Ins | A |
| Soybean2 | N/A | G | T | G | Ins | A |
| Soybean3 | N/A | G | T | G | Ins | A |
| Soybean4 | N | G | T | G | Ins | A |
| Favorable | | T | G | G | A | G |
| Unfavorable | | C | T | C | T | T |
| PI | Accession Name | SEQ ID NO: 8 SNP | SEQ ID NO: 14 SNP | SEQ ID NO: 23 SNP | SEQ ID NO: 32 SNP | SEQ ID NO: 33 SNP |
| Resistant Accessions | | | | | | |
| PI243540 | Sennari | T | G | G | T | G |
| PI200538 | Sugao Zarai | T | G | C | A | G |
| Susceptible Accessions | | | | | | |
| M03256* | | C | T | C | T | T |
| CL968413** | | C | T | C | T | T |
| Soybean1 | N/A | C | T | C | T | T |
| PI606749 | Ina | C | T | Het | T | T |
| Soybean2 | N/A | C | T | Het | T | T |
| Soybean3 | N/A | C | T | Het | T | T |
| Soybean4 | N/A | C | T | Het | T | T |

Each column shows the nucleotide present at the SNP position for the indicated SEQ ID NO.
*American type Culture Collection (ATCC) Accession No. PTA-873; see also U.S. Pat. No. 7,335,820.
**ATCC Accession No. PTA-8915; see also U.S. Pat. No. 7,371,937.
Het-accession was heterozygous at the SNP position; Del-accession had the deletion at the SNP position; Ins-accession had the CA dinucleotide insertion at the SNP position.

TABLE 8

Detailed SNP Genotyping Data Related to Aphid Resistance
As Determined by KASP ™ Assays

| | | | | | |
|---|---|---|---|---|---|
| Favorable | C | C | G | T | A |
| Unfavorable | G | A | T | A | G |

TABLE 8-continued

Detailed SNP Genotyping Data Related to Aphid Resistance
As Determined by KASP ™ Assays

| PI | Accession Name | SEQ ID NO: 12 SNP | SEQ ID NO: 14 SNP | SEQ ID NO: 19 SNP | SEQ ID NO: 24 SNP | SEQ ID NO: 25 SNP |
|---|---|---|---|---|---|---|
| Resistant Accessions | | | | | | |
| PI200538 | Sugao Zarai | C | C | T | T | A |
| PI243540 | Sennari | G | C | T | A | G |
| Susceptible Accessions | | | | | | |
| PI548657 | Jackson (Rag) | G | A | G | Het | G |
| PI548663 | Dowling (Rag1) | G | A | n.d. | A | G |
| PI597386 | Dwight | G | A | G | A | G |
| PI606749 | Ina | G | A | G | A | G |
| MT9131044** | MT9131044** | G | A | G | A | G |
| PI518671 | Williams 82 | G | A | G | A | G |
| PI614088 | Loda | G | A | n.d. | Het | G |
| BPR99805 | BPR99805 | G | Het | n.d. | A | n.d. |
| MT9206166 | MT9206166 | G | A | n.d. | Het | n.d. |
| Favorable | | C | A | A | A | A |
| Unfavorable | | G | T | T | G | T |

| PI | Accession Name | SEQ ID NO: 26 SNP | SEQ ID NO: 28 SNP | SEQ ID NO: 29 SNP | SEQ ID NO: 30 SNP | SEQ ID NO: 31 SNP |
|---|---|---|---|---|---|---|
| Resistant Accessions | | | | | | |
| PI200538 | Sugao Zarai | C | A | A | A | A |
| PI243540 | Sennari | G | n.d. | A | A | A |
| Susceptible Accessions | | | | | | |
| PI548657 | Jackson (Rag) | G | T | T | G | T |
| PI548663 | Dowling (Rag1) | Het | T | T | G | T |
| PI597386 | Dwight | G | T | T | G | T |
| PI606749 | Ina | G | T | T | G | T |
| MT9131044 | MT9131044 | G | T | T | G | T |
| PI518671 | Williams 82 | G | T | T | G | T |
| PI614088 | Loda | Het | Het | T | G | T |
| BPR99805 | BPR99805 | G | n.d. | T | G | T |
| MT9206166 | MT9206166 | Het | Het | T | G | T |

Each column shows the nucleotide present at the SNP position for the indicated SEQ ID NO.
**ATCC Accession No. PTA-8746; see also U.S. Pat. No. 7,339,094.
n.d. not determined; Het: heterozygous.

Example 4

Genotyping Soybean Accessions with Respect to *Phytophthora* Resistance

Phenotype of soybean accessions with respect *Phytophthora* resistance to was determined by the method described in Sandhu et al. (2005) *J Heredity* 96:536-541 and Burnham et al. (2003) *Crop Sci* 43:101-105. Briefly, a slurry of *P. sojae* race 25 was injected into the stems of 7-day old seedlings. Resistance or susceptibility was evaluated 7 days later. Resistant lines were still alive, while susceptible seedlings were dead with brown hypocotyls.

The alleles present at the specified SNP positions for various soybean accessions scored as resistant or susceptible to *Phytophthora* are presented in Table 8.

Example 5

Genotyping Soybean Accessions with Respect to RKN Resistance

Resistant soybean accessions with respect RKN species Meloidogyne javanica were selected from the literature. Penotyping can be determined by the method described in Tamulonis, et al., Crop Sci. 37:783-788 (1997). Seedlings are inoculated with *Meloidogyne javanica* eggs 7 days after planting. Thirty days later, soil is gently washed from the roots and galls are counted.

The alleles present at the specified SNP positions for various soybean accessions identified as resistant or susceptible to RKN are presented in Table 10.

TABLE 9

Detailed SNP Genotyping Data Related to *Phytophthora* Resistance[2]
As Determined by KASP ™ Assays

| Favorable | T | C | G | A | G | G | A |
|---|---|---|---|---|---|---|---|
| Unfavorable | C | T | A | G | T | A | G |
| SPIRIT ID | SEQ ID NO: 6 SNP | SEQ ID NO: 7 SNP | SEQ ID NO: 9 SNP | SEQ ID NO: 10 SNP | SEQ ID NO: 11 SNP | SEQ ID NO: 13 SNP | SEQ ID NO: 15 SNP |
| Resistant Accessions | | | | | | | |
| 1381 | T | C | G | A | G | G | A |
| 1435 | T | C | G | A | G | G | A |
| Susceptible Accessions | | | | | | | |
| 03JR313108 | C | T | A | G | T | A | G |
| S38-T8 | C | T | A | G | T | A | G |
| XR 3962 | C | T | A | G | T | A | G |
| PI518671 | C | T | A | G | T | A | G |
| Favorable | A | A | G | T | T | A | G |
| Unfavorable | G | G | A | C | C | G | C |
| Accession | SEQ ID NO: 16 SNP | SEQ ID NO: 17 SNP | SEQ ID NO: 18 SNP | SEQ ID NO: 20 SNP | SEQ ID NO: 21 SNP | SEQ ID NO: 22 SNP | SEQ ID NO: 27 SNP |
| Resistant Accessions | | | | | | | |
| 1381 | A | A | G | T | T | A | G |
| 1435 | A | A | G | T | T | A | G |
| Susceptible Accessions | | | | | | | |
| 03JR313108 | G | n.d. | A | C | C | G | Het |
| S38-T8 | G | G | A | C | C | G | C |
| XR 3962 | G | G | A | C | C | G | C |
| PI518671 | G | G | A | C | C | G | Het |

Each column shows the nucleotide present at the SNP position for the indicated SEQ ID NO.
Het: heterozygous.
[2]Rsp8 resistance germplasm available for license from ACCESS Plant Technology, Inc., Plymouth, Indiana, United States of America.

TABLE 10

Detailed SNP Genotyping Data Related to *Meloidogyne javanica* RKN Resistance[2] As Determined by TaqMan ® Assays

|  | Favorable | |
|---|---|---|
|  | A | A |
|  | Unfavorable | |
|  | G | C |
|  | SPIRIT ID | |
|  | SEQ ID NO: 34 SNP | SEQ ID NO: 35 SNP |
| Resistant Accessions | | |
| PI548660 (Bragg) | A | A |
| PI595099 (G93-9223) | A | A |
| Susceptible Accessions | | |
| PI548402 (Peking) | G | C |
| PI88788 | G | C |

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method for producing a soybean plant having improved resistance to *Phytophthora*, the method comprising the steps of:
   (a) isolating at least one nucleic acid from a soybean plant selected from a population of soybean plants;
   (b) detecting in the nucleic acid of (a) at least one allele of one or more marker locus associated with improved resistance to *Phytophthora*, wherein the one or more marker locus is a marker locus localizing within a chromosomal interval on soy chromosome 13 defined by and including physical positions 28,452,978-29,529,674, and wherein said chromosomal interval further comprises one or more of the following alleles selected from the group consisting of a T at nucleotide 251 of SEQ ID NO: 6; a C at nucleotide 251 of SEQ ID NO: 7; a G at nucleotide 251 of SEQ ID NO: 9; an A at nucleotide 251 of SEQ ID NO: 10; a G at nucleotide 251 of SEQ ID NO: 11; a G at nucleotide 251 of SEQ ID NO: 13; an A at nucleotide 251 of SEQ ID NO: 15; an A at nucleotide 251 of SEQ ID NO: 16; an A at nucleotide 251 of SEQ ID NO: 17; a G at nucleotide 251 of SEQ ID NO: 18; a T at nucleotide 251 of SEQ ID NO: 20; a T at nucleotide 251 of SEQ ID NO: 21; an A at nucleotide 251 of SEQ ID NO: 22; a C at nucleotide 101 of SEQ ID NO: 27;
   (c) selecting a first soybean plant from the population of (a) based on the presence of the allele detected in (b);
   (d) crossing the first soybean plant of (c) with a second soybean plant wherein said second soybean plant does not comprise the allele or marker locus of (b) associated with improved *Phytophthora* resistance;
   (e) collecting seed from the cross of (d); and
   (f) growing a soybean progeny plant from the seed of (e), wherein said soybean progeny plant comprises in its genome said allele or marker locus associated with improved resistance to *Phytophthora*, thereby producing a soybean progeny plant with improved resistance to *Phytophthora*.

2. The method of claim 1, wherein the chromosomal interval comprises at least two alleles selected from the group consisting of a T at nucleotide 251 of SEQ ID NO: 6; a C at nucleotide 251 of SEQ ID NO: 7; a G at nucleotide 251 of SEQ ID NO: 9; an A at nucleotide 251 of SEQ ID NO: 10; a G at nucleotide 251 of SEQ ID NO: 11; a G at nucleotide 251 of SEQ ID NO: 13; an A at nucleotide 251 of SEQ ID NO: 15; an A at nucleotide 251 of SEQ ID NO: 16; an A at nucleotide 251 of SEQ ID NO: 17; a G at nucleotide 251 of SEQ ID NO: 18; a T at nucleotide 251 of SEQ ID NO: 20; a T at nucleotide 251 of SEQ ID NO: 21; an A at nucleotide 251 of SEQ ID NO: 22; a C at nucleotide 101 of SEQ ID NO: 27.

3. The method of claim 1, wherein the detecting comprises detecting at least one allelic form of a polymorphic simple sequence repeat (SSR) or a single nucleotide polymorphism (SNP).

4. The method of claim 1, wherein the detecting comprises amplifying the marker locus or a portion of the marker locus and detecting the resulting amplified marker amplicon.

5. The method of claim 1, wherein the at least one allele of one or more marker locus associated with the resistance to a pathogen is associated with an allele having any one or combination of selected from the group consisting of: a T at nucleotide 251 of SEQ ID NO: 6; a C at nucleotide 251 of SEQ ID NO: 7; a G at nucleotide 251 of SEQ ID NO: 9; an A at nucleotide 251 of SEQ ID NO: 10; a G at nucleotide 251 of SEQ ID NO: 11; a G at nucleotide 251 of SEQ ID NO: 13; an A at nucleotide 251 of SEQ ID NO: 15; an A at nucleotide 251 of SEQ ID NO: 16; an A at nucleotide 251 of SEQ ID NO: 17; a G at nucleotide 251 of SEQ ID NO: 18; a T at nucleotide 251 of SEQ ID NO: 20; a T at nucleotide 251 of SEQ ID NO: 21; an A at nucleotide 251 of SEQ ID NO: 22; a C at nucleotide 101 of SEQ ID NO: 27, and that is associated with *Phytophthora* resistance.

6. The method of claim 4, wherein the amplifying comprises: (a) admixing an amplification primer or amplification primer pair with a nucleic acid isolated from the first plant, wherein the primer or primer pair is complementary or partially complementary to at least a portion of the marker locus, and is capable of initiating DNA polymerization by a DNA polymerase using the soybean nucleic acid as a template; and (b) extending the primer or primer pair in a DNA polymerization reaction comprising a DNA polymerase and a template nucleic acid to generate at least one amplicon.

* * * * *

SEQUENCE LISTING

<160> NUMBER OF SEQ ID NOS: 250

<210> SEQ ID NO 1
<211> LENGTH: 848
<212> TYPE: DNA
<213> ORGANISM: Glycine max

<400> SEQUENCE: 1

```
ttaggttttt taaacgccta tacggtaacc aaaacagctc gtccagtcaa agcctctgaa        60
ggagcaattg gcacagctca agaagcccat cataccgatt ttgattttt cagatcaaaa       120
gcttctcaat agcatcctgc aaaccaacca aatgctcaga atacacggtt caataatatg       180
tgaaaataaa taatacagtt ggcatttggt agctccaggc aaatcatgaa agaaaaataa       240
agtgcatgra tacctttagt tgctggattt gagatttcaa ttgactccct tcattagttg       300
tcacagaaca agcaatcact ggcctggtga ccccacatgc acgcccaagt gcttgttttg       360
aagggacaaa cacgtagggc acattctaaa aaattcaaat gaataattca tatgattaat       420
aggccaatac aaaaaagaaa aaaaaaatct gggtaacatc gagttaaaac agatcagcag       480
gaatggttaa gattttcatt acawtagttt ttkgtttgtt tgtgggtaac aaatttacaa       540
tagatatcgt gagaattgag acctagtgag agatcacggg gaaaataagt tatgtgtgag       600
cacgagcact gaatctcact tgagagacca wacgtggcat taggtgtgac tacactagga       660
tataaatatg caagtgggta gaatattata ttatattctg ttattgttas gaagaaactt       720
ggcaaagcta caacacaaat aacataacat tatgtataca aataatggca aatgagagca       780
aataaccaga aatgaaacaa catctcataa gaatgcacgt gatgaggtaa ttcagataaa       840
atatcctc                                                               848
```

<210> SEQ ID NO 2
<211> LENGTH: 848
<212> TYPE: DNA
<213> ORGANISM: Glycine max

<400> SEQUENCE: 2

```
ttaggttttt taaacgccta tacggtaacc aaaacagctc gtccagtcaa agcctctgaa      60
ggagcaattg gcacagctca agaagcccat cataccgatt ttgattttt cagatcaaaa      120 gcttctcaat agcatcctgc aaaccaacca aatgctcaga atacacggtt caataatatg     180
tgaaaataaa taatacagtt ggcatttggt agctccaggc aaatcatgaa agaaaaataa     240
agtgcatgya tacctttagt tgctggattt gagatttcaa ttgactccct tcattagttg     300
tcacagaaca agcaatcact ggcctggtga ccccacatgc acgcccaagt gcttgttttg     360
aagggacaaa cacgtagggc acattctaaa aaattcaaat gaataattca tatgattaat     420
aggccaatac aaaaagaaa aaaaaatct gggtaacatc gagttaaaac agatcagcag      480
gaatggttaa gattttcatt acawtagttt ttkgtttgtt tgtgggtaac aaatttacaa     540
tagatatcgt gagaattgag acctagtgag agatcacggg gaaaataagt tatgtgtgag     600
cacgagcact gaatctcact tgagagacca wacgtggcat taggtgtgac tacactagga     660
tataaatatg caagtgggta gaatattata ttatattctg ttattgttas gaagaaactt     720
ggcaaagcta caacacaaat aacataacat tatgtataca ataatggca aatgagagca     780 aataaccaga aatgaaacaa catctcataa gaatgcacgt gatgaggtaa ttcagataaa     840
atatcctc                                                              848

<210> SEQ ID NO 3
<211> LENGTH: 848
<212> TYPE: DNA
<213> ORGANISM: Glycine max

<400> SEQUENCE: 3
ttaggttttt taaacgccta tacggtaacc aaaacagctc gtccagtcaa agcctctgaa      60
ggagcaattg gcacagctca agaagcccat cataccgatt ttgattttt cagatcaaaa      120 gcttctcaat agcatcctgc aaaccaacca aatgctcaga atacacggtt caataatatg     180
tgaaaataaa taatacagtt ggcatttggt agctccaggc aaatcatgaa agaaaaataa     240
agtgcatgya tacctttagt tgctggattt gagatttcaa ttgactccct tcattagttg     300
tcacagaaca agcaatcact ggcctggtga ccccacatgc acgcccaagt gcttgttttg     360
aagggacaaa cacgtagggc acattctaaa aaattcaaat gaataattca tatgattaat     420
aggccaatac aaaaagaaa aaaaaatct gggtaacatc gagttaaaac agatcagcag      480
gaatggttaa gattttcatt acawtagttt ttkgtttgtt tgtgggtaac aaatttacaa     540
tagatatcgt gagaattgag acctagtgag agatcacggg gaaaataagt tatgtgtgag     600
cacgagcact gaatctcact tgagagacca wacgtggcat taggtgtgac tacactagga     660
tataaatatg caagtgggta gaatattata ttatattctg ttattgttas gaagaaactt     720
ggcaaagcta caacacaaat aacataacat tatgtataca ataatggca aatgagagca     780 aataaccaga aatgaaacaa catctcataa gaatgcacgt gatgaggtaa ttcagataaa     840
atatcctc                                                              848

<210> SEQ ID NO 4
<211> LENGTH: 848
<212> TYPE: DNA
<213> ORGANISM: Glycine max
<220> FEATURE:
<221> NAME/KEY: misc_feature
<222> LOCATION: (731)..(732)
<223> OTHER INFORMATION: n is a, c, g, or t

<400> SEQUENCE: 4
```

```
ttaggttttt taaacgccta tacggtaacc aaaacagctc gtccagtcaa agcctctgaa      60
ggagcaattg gcacagctca agaagcccat cataccgatt ttgattttt cagatcaaaa      120 gcttctcaat agcatcctgc aaaccaacca aatgctcaga atacacggtt caataatatg     180
tgaaaataaa taatacagtt ggcatttggt agctccaggc aaatcatgaa agaaaaataa     240
agtgcatgya tacctttagt tgctggattt gagatttcaa ttgactccct tcattagttg     300
tcacagaaca agcaatcact ggcctggtga ccccacatgc acgcccaagt gcttgttttg     360
aagggacaaa cacgtagggc acattctaaa aaattcaaat gaataattca tatgattaat     420
aggccaatac aaaaaagaaa aaaaaatct gggtaacatc gagttaaaac agatcagcag      480
gaatggttaa gattttcatt acawtagttt ttkgtttgtt tgtgggtaac aaatttacaa     540
tagatatcgt gagaattgag acctagtgag agatcacggg gaaaataagt tatgtgtgag     600
cacgagcact gaatctcact tgagagacca wacgtggcat taggtgtgac tacactagga    660
tataaatatg caagtgggta gaatattata ttatattctg ttattgttas gaagaaactt    720
ggcaaagcta nnacacaaat aacataacat tatgtataca ataatggca aatgagagca     780 aataaccaga aatgaaacaa catctcataa gaatgcacgt gatgaggtaa ttcagataaa    840
atatcctc                                                              848

<210> SEQ ID NO 5
<211> LENGTH: 501
<212> TYPE: DNA
<213> ORGANISM: Glycine max
<220> FEATURE:
<221> NAME/KEY: misc_feature
<222> LOCATION: (119)..(119)
<223> OTHER INFORMATION: n is a, c, g, or t
<220> FEATURE:
<221> NAME/KEY: misc_feature
<222> LOCATION: (343)..(343)
<223> OTHER INFORMATION: n is a, c, g, or t

<400> SEQUENCE: 5
tccctcactg atttctctgc accccttcca tttcccacgt tctcaaaaca actttctcaa      60
atatcatgct acgtacccca ccaagcatag taaaccaaac tgccacgttt ccaaagtgnc     120
atgccatagt aatcaaaaca actcaacaca aaacctagaa gaaggaaaac tatcacacaa    180
cttaggagga aaaaatagga gggattttct cattggcttt ggagaacttt acggtgcttc    240
tactcttagc racaataaca acaaccttt agccatcgct gctccaattc tccctcctga     300
cctagaaact tatggttcac cagagttacc aactgatgta aanccggcca ccatttgttg    360
ccctccagta tcttctatcg tcatagactt caagcttcct tgtaacattc cgattttct    420 tttctaatta tataaatata ttaattatta ttaaacattt taattttct tgttttaatt    480 aaaataaata atttggcaat t                                               501

<210> SEQ ID NO 6
<211> LENGTH: 501
<212> TYPE: DNA
<213> ORGANISM: Glycine max
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
```

```
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (106)..(106)
<223> OTHER INFORMATION: n is a, c, g, or t
<220> FEATURE:
<221> NAME/KEY: misc_feature
<222> LOCATION: (152)..(152)
<223> OTHER INFORMATION: n is a, c, g, or t
<220> FEATURE:
<221> NAME/KEY: misc_feature
<222> LOCATION: (187)..(187)
<223> OTHER INFORMATION: n is a, c, g, or t
<220> FEATURE:
<221> NAME/KEY: misc_feature
<222> LOCATION: (214)..(214)
<223> OTHER INFORMATION: n is a, c, g, or t
<220> FEATURE:
<221> NAME/KEY: misc_feature
<222> LOCATION: (256)..(256)
<223> OTHER INFORMATION: n is a, c, g, or t
<220> FEATURE:
<221> NAME/KEY: misc_feature
<222> LOCATION: (267)..(267)
<223> OTHER INFORMATION: n is a, c, g, or t
<220> FEATURE:
<221> NAME/KEY: misc_feature
<222> LOCATION: (292)..(292)
<223> OTHER INFORMATION: n is a, c, g, or t
<220> FEATURE:
<221> NAME/KEY: misc_feature
<222> LOCATION: (311)..(311)
<223> OTHER INFORMATION: n is a, c, g, or t
<220> FEATURE:
<221> NAME/KEY: misc_feature
<222> LOCATION: (316)..(316)
<223> OTHER INFORMATION: n is a, c, g, or t

<400> SEQUENCE: 6
aaactcgcga ctctttcctc acactgatga tcttttttt caagaaacan catctgagct    60
cgtagaacat tgatcgggtg cggncatagg tggacactca naactncacc cgccagtcag   120
gggaatagtc atcactgccc atcacgcgac gnaagtgctt gtcggggcgg agggcttagg   180
ccatgcnttg cgctgttgac tataaatact gtantcgggt gtcgtggtgt acgtcgtcgt   240
gtcctagttt ycctgntctc catgttncat taatattctt ttctctaaaa anacaccaac   300
tatattttct nttttnttg cattcatttt cttccatcct cacaatttta attttttca    360 tctaaacaca aaattttgaa aataaaagaa tttcaaatga aatatttgaa attttagaa    420 tttaaaattt ctcataattt caaatgaaag attttaatta attatattta atcattcatg   480
tacactagat ataatttcta a                                             501

<210> SEQ ID NO 7
<211> LENGTH: 501
<212> TYPE: DNA
<213> ORGANISM: Glycine max
<220> FEATURE:
<221> NAME/KEY: misc_feature
<222> LOCATION: (239)..(239)
<223> OTHER INFORMATION: n is a, c, g, or t

<400> SEQUENCE: 7
aatgcgtcta taacaacact taatgaggta atcaaatgaa tttgatgttt tttttattac    60
cttggtgaaa taacgctcaa tcttttccag ttgctgaccc aatggaggca ctattttcca   120
attttgaagc tcggtaagta tagagtctaa cttgttgtac agtgctgctg ccattcttaa   180
agcttccaac ttctttgtgg ggaaaccttc aaaccgtgat agcacctata tgcagcaana   240
```

-continued

```
gaattgctta ycatggtaaa tgaaagaacc aagagcagta ataaatggaa ttgaaatgaa      300
aatcatatgg aaatgaattt tctaaagtca cctgtgattc atcagttagg ttctcaagaa      360
cggattcaac atctctgtgg aacctgctca attctgtcat gtcctttgtc ttgaaattag      420
taatggtaga tctcagctcc aagatttgct ttgtgtactt tgaacatct tcttctattt       480 gttggaagta agaggatcta a                                                501
```

<210> SEQ ID NO 8
<211> LENGTH: 501
<212> TYPE: DNA
<213> ORGANISM: Glycine max
<220> FEATURE:
<221> NAME/KEY: misc_feature
<222> LOCATION: (192)..(192)
<223> OTHER INFORMATION: n is a, c, g, or t
<220> FEATURE:
<221> NAME/KEY: misc_feature
<222> LOCATION: (297)..(297)
<223> OTHER INFORMATION: n is a, c, g, or t

<400> SEQUENCE: 8

```
tcctggacct tccaatcaac ccctatcttc ctcgcccaaa actccttctc atgcttcgcc      60
ctagacctcc agggccacgg ccactcccag ggcctcaaag cctacgtccc taacgtacac     120
ctcgccgcac acgattgcct ctccttcttc aattccatca gaacccaaaa ccctaacctc     180
ccttccttcc tntacggcga gtccatgggc gccgcaatct ccctcctcat ccacctcgtc     240
aactccgaaa yggaacccaa atctcaaccc ttccaaggtg ccgttttggt ggccccnatg     300
tgcaaaatct ccgacaacgt gcgacccaaa tggccaatcc cgcaaatcct cactttccta     360
tcaagattct tccccactct ccccattgtt cccactcccg atcttctcta caagtccgtc     420
aaagttgacc acaaaaaagt catcgccgac atgaaccctt gcgttaccg cgggaagccc      480 aggttgggga ctgtggtgga g                                                501
```

<210> SEQ ID NO 9
<211> LENGTH: 501
<212> TYPE: DNA
<213> ORGANISM: Glycine max
<220> FEATURE:
<221> NAME/KEY: misc_feature
<222> LOCATION: (166)..(166)
<223> OTHER INFORMATION: n is a, c, g, or t

<400> SEQUENCE: 9

```
ttcctcgtca tctttgtcag ctggaggctg cttaggaacc tccatgctga caatggaata      60
agttgttagg acaacatcat gcctagccac ctcataagga tcttttgtcc gattgcttcc     120
atggtatact agcacagaga gacttgcctg accatttacc ttgctncgca gctcctcagc     180
ccattggcgc aggacactag tggggcaaac aataagggtc ccagcagatg gccttcccct     240
gtcttgcttc racaaactca tgctcttggt tggatatcta cttggattat cctcacacat     300
attagattct tcctttactc taccagtctt aggaagcacg tcatcatcca catccagatt     360
cagagtttcc aattcacttt ttcgggcatt ggtgcaccca ttaagtaatg gaggtctttc     420
ctttaatatt aatgcaatag ttgatactgt ttttccaagt ccctacaaga gaaaattttt     480
taactcacca aggcacaaga a                                                501
```

<210> SEQ ID NO 10
<211> LENGTH: 501
<212> TYPE: DNA

<213> ORGANISM: Glycine max
<220> FEATURE:
<221> NAME/KEY: misc_feature
<222> LOCATION: (106)..(106)
<223> OTHER INFORMATION: n is a, c, g, or t
<220> FEATURE:
<221> NAME/KEY: misc_feature
<222> LOCATION: (499)..(499)
<223> OTHER INFORMATION: n is a, c, g, or t

<400> SEQUENCE: 10

```
taaataaata aataggaaaa aaattaaatt aacgttgcca ctgcactaaa gcttcaattc      60
ttctatcaca agacacttca ttcggcatgg ttcaataact gattcngttt tcagagaaac     120
cttacacaat cacagcattc ggaatttcac tctgttttg gcaaagaaga aaccctacct     180
cctgaaagta acaatcgtcg tcttcatcaa gaaccttctg gaccgtctgc atatctatat    240
aaaacatgtc rtcgtcttcg tcggcattac cggtgaacaa tcccgaaagg tccacatcag    300
catccgccat cacaacagca ccaccacaac aacaaccaaa aaaaaaaccc taaaagcgct    360
ttcttaagct gttacacttc cgcagaaaca aaaactcttg ctccgaattc agaatcactt    420
catcgaatcg catagcggag aaaaaaagag agagtgtgtg tggaatcgac gaaaattgcg    480
gagtcagcga tggtttctna g                                              501
```

<210> SEQ ID NO 11
<211> LENGTH: 501
<212> TYPE: DNA
<213> ORGANISM: Glycine max
<220> FEATURE:
<221> NAME/KEY: misc_feature
<222> LOCATION: (255)..(255)
<223> OTHER INFORMATION: n is a, c, g, or t
<220> FEATURE:
<221> NAME/KEY: misc_feature
<222> LOCATION: (257)..(257)
<223> OTHER INFORMATION: n is a, c, g, or t
<220> FEATURE:
<221> NAME/KEY: misc_feature
<222> LOCATION: (305)..(404)
<223> OTHER INFORMATION: n is a, c, g, or t

<400> SEQUENCE: 11

```
aaattaaaaa ataatcttat aaaaaaagac aaataaattg ttataaataa tcttataatt     60
cgaatctgag gaagtattag atataaaaga aaaaaaaaag ctgatgcgtt aagaagcatg    120
tagaagtttg acgataattc ttaaacatca acatcattac ctaataacga cacgcgttta    180
atgtgagcaa tctttggcca gtcttcgcct tcgggttccc ggcaacgttg tttgagcaac    240
ggacaattga kaatncncaa agttgaaatg gatttgggca gaccctcctc tggtaagcat    300
tcgannnnnn nnnnnnnnnn nnnnnnnnnn nnnnnnnnnn nnnnnnnnnn nnnnnnnnnn    360
nnnnnnnnnn nnnnnnnnnn nnnnnnnnnn nnnnnnnnnn nnnnggcaat gattctaatt    420
gggggcactc tttgatatac agactctgga gatgattatg agcctgcccc tgtgaaatcc    480
tctttagatt aggacacttc c                                              501
```

<210> SEQ ID NO 12
<211> LENGTH: 501
<212> TYPE: DNA
<213> ORGANISM: Glycine max
<220> FEATURE:
<221> NAME/KEY: misc_feature
<222> LOCATION: (149)..(149)
<223> OTHER INFORMATION: n is a, c, g, or t
<220> FEATURE:
<221> NAME/KEY: misc_feature

```
<222> LOCATION: (174)..(174)
<223> OTHER INFORMATION: n is a, c, g, or t
<220> FEATURE:
<221> NAME/KEY: misc_feature
<222> LOCATION: (188)..(188)
<223> OTHER INFORMATION: n is a, c, g, or t
<220> FEATURE:
<221> NAME/KEY: misc_feature
<222> LOCATION: (194)..(194)
<223> OTHER INFORMATION: n is a, c, g, or t

<400> SEQUENCE: 12
ataaaaatct tcctgagtat tgggaagata tctagcggaa aggtcgttag agagtcacag      60
ccaccatcaa tgtgcaacct tagaaggaaa tcatagcaac tgtgcatggg aatattgtta     120
tttgaacaag agtaattgcg cccaatctnt tccagtaaag ctgcctccac gttntgacct     180
ctaatggnaa gctnttcaa agttgtcgga tgatcaattt gcagctttcc acagtctcct     240
agggttaatt satgaatatc tggggcactg agagcagaag gtacaagttg ttcgcaccca     300
gaaatcttta gataatttaa atgacatagt tgctctggca agtgcccttt cagcttggga     360
caacgctcca tagaaagacg ttgaagacgt ggaaaagcac ctgtcacacc tttacattcc     420
cattcttccc attccttcat atcggagaac tccaaagatt ccaaggatgt aaatgaacaa     480
gagctactcc cgaaaaaatc a                                               501

<210> SEQ ID NO 13
<211> LENGTH: 501
<212> TYPE: DNA
<213> ORGANISM: Glycine max
<220> FEATURE:
<221> NAME/KEY: misc_feature
<222> LOCATION: (247)..(247)
<223> OTHER INFORMATION: n is a, c, g, or t

<400> SEQUENCE: 13
gaagaaattg gaggcaaaga atgaggaatt agagaagtat ttgagtgagt tgaagggaga      60
gaattggtta tcaaaggaag agttttgagaa gtttgttgag gaagtaagga gtgtgaaggg    120
gagtgggtat gagggtggtg ggttggatga gataagagag tttgcaagag gggtgattga    180
gaaggagatt gagaagcatg ctgctgatgg gcttgggaga gtggattatg ctcttgccag    240
cggcggnggt rcggtggtga agcattcgga ggtgtttgat ctggggaggg gcaattggtt    300
cttgaagtct gctagaaatg gtgtcaaccc caacgccgag aagatgttga aaccgagctt    360
tggcgagcct gggcagtgtt tccccttgaa ggatactaga gggtttgtgc agatcaggct    420
ccgcactgcc atcattcccg aggctgtcac cttggaacat gtagcaaagg tgatgcattt    480
tcattctaaa tctaaatatt g                                               501

<210> SEQ ID NO 14
<211> LENGTH: 501
<212> TYPE: DNA
<213> ORGANISM: Glycine max

<400> SEQUENCE: 14
aaaagctcca cgtgtgaata tcaaccttga tttgccatga aaccatataa tatcaatatc      60
aattatgttg atccagacgc atactataac aatcttgatc aaggggataa atgtgtgaat    120
tagcatctca gtaatcaata tacagtggtt tttgacaaga ccaagaagcc tagttatagt    180
tatcacttca catatggaac cacagcaacg agtttgtctc ttttgcagtc tgtactaaaa    240
ttgatgatat mttgtcgcac atagctccca ctaagctcta tggggacaag tttgagtgat    300
```

```
acctaacaga cttctatgat ctagtagtta cgtttgcaaa ttacaacatc atcacaatta      360
cataccaaac cagtaaaaac tggacaacaa acagttaagc aagttgttca ttagttacat      420
acccttctct cctcaagggc aagcctcttg tgtagccgct cttggtgatt aaaaaattcc      480
aaaaacaaat ccctcatgtc a                                                501

<210> SEQ ID NO 15
<211> LENGTH: 501
<212> TYPE: DNA
<213> ORGANISM: Glycine max

<400> SEQUENCE: 15
atagacgatg ctgaaaatgg aagtagtggg gctggcaatg aaaagacaat tcaaaagaat       60
gaaaacctcc tcctgaattg gcccttaatg tcctctatca tcgcttattg tgttttctca      120
cttcatgata ttacttatac agaggtatga tacttaatga ggttaaaaat gtactattat      180
tctcctttta tatatgctgt ttggattttt cctgcttttt atccatgtgt tttctttagg      240
ttttctcgtt rtggtctgtt agtcctcaaa ggatgggggg tttgaacttt acaagtgatg      300
atgttggtaa tattctttca atatcaggtg catctctaga accaacaata gattcttatt      360
actgttgggc atacatgttt ttccttacta gctttccttc catacataac gattgcacat      420
aaattttatg catttacatg agaccatatg gtaacttctt gcaaggtttt ttctctttat      480
actggtcttg ttgaatgaat t                                                501

<210> SEQ ID NO 16
<211> LENGTH: 501
<212> TYPE: DNA
<213> ORGANISM: Glycine max
<220> FEATURE:
<221> NAME/KEY: misc_feature
<222> LOCATION: (248)..(248)
<223> OTHER INFORMATION: n is a, c, g, or t

<400> SEQUENCE: 16
tatcgaattt gagctgtaga ggatccaatt ctgatgtgga cagatagagc atttgtcatg       60
tgtcttcata taacgcgtga gagactagag tcatgatctt gtgtttcaag gtttctcctt      120
aatttggttg tgtgtacgtt tgttaactta ccctttgtta ttttttccatt tgtgcttca     180 aaacaaagtg gcatgacatc ttttctgatc tttttttgtg tttgaatgat gcatataaaa      240
tggtgtanga ragaaagacc tgagtgaaac aaacatggca gaggagaata tcaggcaacc      300
attgttggag aaaaagtact atgaggactg ccccggttgt aaagtggatc aagccaaaga      360
gttgagtaag ggacagggtg tttccattag aaatctttg ataatatgga tggtggtgtt      420
gtgttctggt aagcatttaa ctctatttt tttagtattt tcacttcttg ataagttggt      480
tattcacttg ttctagttgc a                                                501

<210> SEQ ID NO 17
<211> LENGTH: 501
<212> TYPE: DNA
<213> ORGANISM: Glycine max
<220> FEATURE:
<221> NAME/KEY: misc_feature
<222> LOCATION: (200)..(200)
<223> OTHER INFORMATION: n is a, c, g, or t
<220> FEATURE:
<221> NAME/KEY: misc_feature
<222> LOCATION: (360)..(360)
<223> OTHER INFORMATION: n is a, c, g, or t
<220> FEATURE:
<221> NAME/KEY: misc_feature
```

<222> LOCATION: (362)..(362)
<223> OTHER INFORMATION: n is a, c, g, or t

<400> SEQUENCE: 17

```
ttgtagacca taacatctca aaaatagctt aaacataact caatacatat tcccatcacc    60
gactctatgg gtttaacttt ccaaataaga caggagctta tagattaatt tgacctaaaa   120
tacccaattt aggacgtaga cgtttgaaaa tgacaaagcg aatatgaaat cagaattatt   180
aagttacctg tgtctataan accaataatg atatcagttg atgggtgttt gtgtaatgtg   240
ggagtgccat ractataata aggcttcatt cccaactctg attccaagaa atcccaagat   300
cgcgttgtgt gtaactcaag cactggatca gggaacacag acaccacacc atcgtgaccn   360
gnttacaaat caacactatc ataaattaac ttgtttaata attattattt ttataatttt   420
attgcagtta tttatattaa cataattggc ttttctgtag tactgaacta agggtaaaaa   480
ataaagaaaa aatgtatatg g                                             501
```

<210> SEQ ID NO 18
<211> LENGTH: 501
<212> TYPE: DNA
<213> ORGANISM: Glycine max
<220> FEATURE:
<221> NAME/KEY: misc_feature
<222> LOCATION: (113)..(113)
<223> OTHER INFORMATION: n is a, c, g, or t
<220> FEATURE:
<221> NAME/KEY: misc_feature
<222> LOCATION: (266)..(266)
<223> OTHER INFORMATION: n is a, c, g, or t
<220> FEATURE:
<221> NAME/KEY: misc_feature
<222> LOCATION: (333)..(333)
<223> OTHER INFORMATION: n is a, c, g, or t

<400> SEQUENCE: 18

```
gcctgaagga atgcatgtcc tccttccatc tcttgatgat ctgtggatag aggattgtcc    60
aaaagttgaa atgtttcccg aaggaggttt gccatcaaat ttaaaaagta tgngtctcta   120
tggtagttac aaactatgt ccttattgaa aactgccttg ggaggcaatc actctctaga   180
aagattatct attggaggag tggatgttga gtgtcttcct gaggaaggtg tactgccaca   240
ctctcttctt rctctagaga tcaggnactg tccagatcta aaaagactgg actacaaagg   300
tctctgccac ctctcctctc tcaaggaatt gantcttgtt ggctgcccca ggctcgaatg   360
cttaccagag gagggtctgc ccaaatccat ttcaactttg tggatttggg gggactgtca   420
gttgctcaaa caacgttgcc gggaacccga aggcgaagac tggccaaaga ttgctcacat   480
taaacgcgtg tcgttattag g                                             501
```

<210> SEQ ID NO 19
<211> LENGTH: 501
<212> TYPE: DNA
<213> ORGANISM: Glycine max
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (169)..(169)
<223> OTHER INFORMATION: n is a, c, g, or t
<220> FEATURE:
<221> NAME/KEY: misc_feature
<222> LOCATION: (184)..(184)
<223> OTHER INFORMATION: n is a, c, g, or t

<400> SEQUENCE: 19

```
ggaggtttgc catcaaattt aaaaagtatg ngtctctatg gtagttacaa acttatgtcc    60
ttattgaaaa ctgccttggg aggcaatcac tctctagaaa gattatctat tggaggagtg   120
gatgttgagt gtcttcctga ggaaggtgta ctgccacact ctcttcttnc tctagagatc   180
aggnactgtc cagatctaaa aagactggac tacaaaggtc tctgccacct ctcctctctc   240
aaggaattga ktcttgttgg ctgccccagg ctcgaatgct taccagagga gggtctgccc   300
aaatccattt caactttgtg gatttggggg gactgtcagt tgctcaaaca acgttgccgg   360
gaacccgaag gcgaagactg gccaaagatt gctcacatta acgcgtgtc gttattaggt    420
aatgatgttg atgtttaaga attatcgtca aacttctaca tgcttcttaa cgcatcagct   480
tttttttttc ttttatatct a                                             501
```

<210> SEQ ID NO 20
<211> LENGTH: 501
<212> TYPE: DNA
<213> ORGANISM: Glycine max

<400> SEQUENCE: 20

```
aagcaacaac tactctctca acctcttgct ttgaacaatt gtacttcacc tccaaggcag    60
atatctgagc aagctcatca cttatgtcaa ttttcatatc accctcactt acaaggctag   120
tagtatcctt gggttgtgaa tattcttcac tcccttcaaa tagccaggat accgattgct   180
ctaatttgcc atcatttaac attaaggcca acgtcgctcg ctcggaagag aaccccattg   240
ccactaactg ytgcgcaagt gattctagct ttctcgacat taggtacccg caacaacggt   300
catgcaactc ttgcgctctc ctttccctct gcctctggtg cttcctctca ttcttcaagc   360
ggatcttctc ccttctatca ttatcacaac caggtatact atctggccga gtagaagagc   420
ttgttgccgt taccttctct ttagactctt ctgattcacc agagcagcta ccactgttag   480
aaaccgagtc acactcagac a                                             501
```

<210> SEQ ID NO 21
<211> LENGTH: 501
<212> TYPE: DNA
<213> ORGANISM: Glycine max

<400> SEQUENCE: 21

```
cagtaaggga gggcaactag atgaaaaata atccaatagt taaaggtaaa gggagagcca    60
agaaaattat aggttaaacc aattaagagg gattacgggg taaattgtct atctttgcat   120
ttaaccaatc ccacctaatg ggaaggacag agttatttga gttgaaacaa ttgagaagtc   180
actgttattt gataaaattca gtaataatca tttcaaaata tcaaccacat aaataccgct   240
aaaacacgca ygactaacta actactaacc agcgatcttc tgtactcaaa tttatgagca   300
agacaaaagc aacttccaat gtacattata ggccgctaat agcataacgc tagacacagt   360
aaatagcata acactagaca cattatacga taaatattta acagaaggtt tctggtaagc   420
aactaaacaa gcatgaaggt aacataacca ggtcgaagaa aatgaacact aagatcctgc   480
tcaagatgaa tacaccaaaa a                                             501
```

<210> SEQ ID NO 22
<211> LENGTH: 501
<212> TYPE: DNA
<213> ORGANISM: Glycine max
<220> FEATURE:
<221> NAME/KEY: misc_feature

```
<222> LOCATION: (214)..(214)
<223> OTHER INFORMATION: n is a, c, g, or t

<400> SEQUENCE: 22
gctcttaatg tgtatatatg tgtgtgtgtg tgtgtgtatg gccataacat gacaattcac      60
gaatgatcaa acactagcat aagcaacctg gtctcgtgca ttcaaaacac gtagcaagtg     120
gcaatgaaaa aaagattaaa ataaaaacaa ttcttttatt attttgtga aaaaataaat     180 aaaggagag agagagtgat ggtttagcag caanctgctt cttgttgtgt tcgtctacgg     240
cgaatcgagc ragggcttcg gtttcgacgc tgttttgaga gccttgggag tcgtgtaagc     300
ctccgatcgt ggccatcggc gagtggtggt ggtggtattc ggagcagtcc ccggacgaag     360
atcgaagagc gaagaaaatg aagagaaaga agaagaaaaa gtaacgcttc gcaatggaaa     420
tcgaagaaga agagtttgat gctctcattc ggtatgtttc ttcctttctt gatgcagtga     480
aagtgtgccg gccgtattta t                                              501

<210> SEQ ID NO 23
<211> LENGTH: 187
<212> TYPE: DNA
<213> ORGANISM: Glycine max
<220> FEATURE:
<221> NAME/KEY: misc_feature
<222> LOCATION: (23)..(23)
<223> OTHER INFORMATION: n is a, c, g, or t

<400> SEQUENCE: 23
gcaatgccaa cgatwgtagt tanygaaaac tcatttcctc acttaatgac ataaatgtgc      60
gtaacctttc agcattgtat aaagttcsaa acccatcawa gcatktaacg tgatygcttg     120
caactgaaaa atgacgggtk gtcttyggta tatttkttgc ttgatcatct tccaacctga     180 arcagat                                                              187

<210> SEQ ID NO 24
<211> LENGTH: 501
<212> TYPE: DNA
<213> ORGANISM: Glycine max
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (148)..(148)
<223> OTHER INFORMATION: n is a, c, g, or t
<220> FEATURE:
<221> NAME/KEY: misc_feature
<222> LOCATION: (167)..(167)
<223> OTHER INFORMATION: n is a, c, g, or t
<220> FEATURE:
<221> NAME/KEY: misc_feature
<222> LOCATION: (314)..(314)
<223> OTHER INFORMATION: n is a, c, g, or t

<400> SEQUENCE: 24
cgccttattc cccaaagatt acaggtttga cnaggagggt ttaattcagc tgtggatggc      60
ggaaaacttt ttacaatgtc ctcaacagag taggagtcca gaagaagtcg gtgaacaata     120
cttcaacgat cttttgtcaa ggtccttntt tcaacaatca agcaccntag agagaacacc     180
ttttgtcatg catgaccttc tcaatgattg gcaaaatatg tttgtaggga catctgtttc     240
aggttggaag wtgatcaagc aaaaaatata ccgaagacaa cccgtcattt ttcagttgca     300
agcgatcacg ttanatgctt tgatgggttt cgaactttat acaatgctga aaggttacgc     360
```

```
acatttatgt cattaagtga ggaaatgagt tttcgtaact acaatcgttg gcattgcaag    420
atgtcaacac gtgaattatt ctccaagttt aagttcttac gtgtcttatc tctgtctggt    480
tattctaacc taacagagtt g                                              501
```

<210> SEQ ID NO 25
<211> LENGTH: 201
<212> TYPE: DNA
<213> ORGANISM: Glycine max
<220> FEATURE:
<221> NAME/KEY: misc_feature
<222> LOCATION: (147)..(147)
<223> OTHER INFORMATION: n is a, c, g, or t
<400> SEQUENCE: 25

```
atgtcattta aatkmtctar agatttctgg gtgygaacaa cttgtacctt ytgctctcag     60
tgcccctgat attcatmaat tataccctagg agactgtgga ragctgcaaa ttgatcatss   120
gacaactttg aaagagctta ccattrnagg tcacaacgtg gaggcagcbt taytsgaaca   180
gattggrcgc aattactctt g                                              201
```

<210> SEQ ID NO 26
<211> LENGTH: 501
<212> TYPE: DNA
<213> ORGANISM: Glycine max
<220> FEATURE:
<221> NAME/KEY: misc_feature
<222> LOCATION: (89)..(89)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (107)..(107)
<223> OTHER INFORMATION: n is a, c, g, or t
<220> FEATURE:
<221> NAME/KEY: misc_feature
<222> LOCATION: (143)..(143)
<223> OTHER INFORMATION: n is a, c, g, or t
<220> FEATURE:
<221> NAME/KEY: misc_feature
<222> LOCATION: (255)..(255)
<223> OTHER INFORMATION: n is a, c, g, or t
<220> FEATURE:
<221> NAME/KEY: misc_feature
<222> LOCATION: (475)..(475)
<223> OTHER INFORMATION: n is a, c, g, or t
<400> SEQUENCE: 26

```
gcaactatgt catttaaatt ctctaaagat ttctgggtgt gaacaacttg taccttctgc     60
tctcagtgcc cctgatattc ataaattana cctaggagac ngtgganagc tgcaaattga   120
tcatgggaca actttgaaag agnttaccat tgaaggtcac aacgtggagg cagccttatt   180
cgaagagatt gggcgcaatt actcttgttc aaataacaat attcccatgc acagttgcta   240
tgatttcctt staancttgc gcatcaaagg tggctgcgac tctttaacga cctttccgct   300
agatatgttc acaatactca gggaactttg tatctggaag tgtcctaatc tacggaggat   360
ttcacaaggg caggctcata atcatctcca gactctggat atcaaagagt gcccccaatt   420
agaatcattg cctgaaggaa tgcatgtcct ccttccatct cttgattctc tgtgnataga   480
tgattgtcca aaagttgaaa t                                              501
```

<210> SEQ ID NO 27
<211> LENGTH: 201

```
<212> TYPE: DNA
<213> ORGANISM: Glycine max

<400> SEQUENCE: 27
gtcacaacgt ggaggcagcb ttaytsgaac agattggrcg caattactct tgttcaaata      60
acaatattcc catgcacagt tgctatgatt tccttstaag sttggacatc aatggtggct     120
gcgactctct aacgaccwtt cmgytagata tsttcccaat actcaggsrg cttgatatcw     180
ggaagtgtcc taatctacrg a                                               201

<210> SEQ ID NO 28
<211> LENGTH: 501
<212> TYPE: DNA
<213> ORGANISM: Glycine max
<220> FEATURE:
<221> NAME/KEY: misc_feature
<222> LOCATION: (169)..(170)
<223> OTHER INFORMATION: n is a, c, g, or t
<220> FEATURE:
<221> NAME/KEY: misc_feature
<222> LOCATION: (178)..(178)
<223> OTHER INFORMATION: n is a, c, g, or t
<220> FEATURE:
<221> NAME/KEY: misc_feature
<222> LOCATION: (235)..(235)
<223> OTHER INFORMATION: n is a, c, g, or t
<220> FEATURE:
<221> NAME/KEY: misc_feature
<222> LOCATION: (244)..(245)
<223> OTHER INFORMATION: n is a, c, g, or t
<220> FEATURE:
<221> NAME/KEY: misc_feature
<222> LOCATION: (319)..(320)
<223> OTHER INFORMATION: n is a, c, g, or t

<400> SEQUENCE: 28
ggtgtgccat caaatttaaa aagaatgggt ctttatggta gttccaaact tatctcattg      60
aaaagtgcct tgggaggcaa tcactctcta gaaagcttag agattggaaa agtggatctt    120
gagtctcttc ttgacgaagg tgtactgcca cactctcttg ttactctann gatcaggnag    180
tgtggagatc taaaaagact ggactacaaa ggtctctgcc acctctcctc tctcnagaca    240
ttgnntcttt wtgactgccc caggctcgaa tgcttaccag aggagggtct gcccaaatcc    300
atttcaactt tgcacattnn caattgtccg ttgctccaac aacgttgccg ggaacccgaa    360
ggggaagact ggccaaagat tgctcacatt gaacatgtgt attgtaaata aggtagtgag    420
gttgattata aagaattatg gtgaaacttg tacatgcttc tctattgcct ccaatttact    480
aaataattgt tttctaaact t                                              501

<210> SEQ ID NO 29
<211> LENGTH: 153
<212> TYPE: DNA
<213> ORGANISM: Glycine max

<400> SEQUENCE: 29
tagtctccta acwcttttgt cattatagaa acactttgca gcaccaaart ccwtcagttt      60
gaacattgct ggagtatacc cttgtgcaac gctttcttga ttcattttc ctgtgtcata     120 acatgaaaca atacataaaa gaattaaagt ttg                                 153

<210> SEQ ID NO 30
<211> LENGTH: 161
<212> TYPE: DNA
<213> ORGANISM: Glycine max
```

<400> SEQUENCE: 30

```
tcccttgccc tactagtctc ctaacwctttt tgtcattata gaaacactttt gcagcaccaa     60
artccwtcag tttgaacatt gctggagtat acccttgtgc aacgctttct tgattcattt    120
ttcctgtgtc ataacatgaa acaatacata aagaattaa a                         161
```

<210> SEQ ID NO 31
<211> LENGTH: 165
<212> TYPE: DNA
<213> ORGANISM: Glycine max

<400> SEQUENCE: 31

```
tcccttgccc tactagtctc ctaacwctttt tgtcattata gaaacactttt gcagcaccaa     60
artccwtcag tttgaacatt gctggagtat acccttgtgc aacgctttct tgattcattt    120
ttcctgtgtc ataacatgaa acaatacata aagaattaa agtttt                    165
```

<210> SEQ ID NO 32
<211> LENGTH: 312
<212> TYPE: DNA
<213> ORGANISM: Glycine max

<400> SEQUENCE: 32

```
atgggtgaaa agttatcgca aattatggaa gaaaagttaa gtgggtcagg cttgtcattt     60
taagtgtctc cttattttg ttgatcgatc actagctagt gatcatcatc yacatcaagt    120
gtctaaataa gaatcgtgca tatatgcagg tcatgatgtg gcctacaagt gcatgttcgt    180
tgtgattttc ccttttccct tttcccgttt ggatgatttt tcctactwgt gcattgaagg    240
tctcagtaaa gttatttcta tcatgcgtgt tttgtgttta attaattaag tgactcattt    300
gcttgttttg tg                                                        312
```

<210> SEQ ID NO 33
<211> LENGTH: 179
<212> TYPE: DNA
<213> ORGANISM: Glycine max

<400> SEQUENCE: 33

```
agatgtcata aattactcca aacttctttt attaacactt tcgcccccaa mctttcccaa     60
ttccagatct gccttcccgt ttaaaaaaat cacggtcggg tcataactcc aaaatcagag    120
gggcgtaaag gagaagcaga agattctaga ttaaggaaga gaacgaagaa aggaacgcc     179
```

<210> SEQ ID NO 34
<211> LENGTH: 103
<212> TYPE: DNA
<213> ORGANISM: Glycine max

<400> SEQUENCE: 34

```
aagcacactc aacctcgaga tggagcatcg gctcctcgtt ttccatctga tcctaaagat     60
raaataagga taaatcttct catttcatca aacaacacac aaa                      103
```

<210> SEQ ID NO 35
<211> LENGTH: 501
<212> TYPE: DNA
<213> ORGANISM: Glycine max
<220> FEATURE:
<221> NAME/KEY: misc_feature
<222> LOCATION: (163)..(163)
<223> OTHER INFORMATION: n is a, c, g, or t

<400> SEQUENCE: 35

```
agtcaaccaa ctatacctg tatacactca ctaatccaaa aatcttatgt actgatacat    60
ttcagcgatg atgatcaatg acctcaactt gtagaacctc catataaaaa cggaagtaat   120
aaaaagctca aggagctgtg gttggcagat acaagatgtt ganagcaatg ttactccatt   180
gacagaaaga attacatacc acaaactaac ttaaaagtct gcagacaccg cctgaatttc   240
tgatttcatt mctcctatac atagttgcct tttgccatct tcagtgcgtt tacaagccca   300
tataaatata acaatgccga attcagccga tgcatgaact catcaatata gcagtttcct   360
aattataaat ctttactggc ttctcaaatg tgtggcgatt ctgaaaacaa aagccatatt   420
attttgaatg gtgcaaacaa aagcaagcat tttaccccaa agcaaaagaa agcttactcg   480
acagaaaatt cactaacctg g                                             501
```

<210> SEQ ID NO 36
<211> LENGTH: 48
<212> TYPE: DNA
<213> ORGANISM: Artificial Sequence
<220> FEATURE:
<223> OTHER INFORMATION: Primer

<400> SEQUENCE: 36

```
gaaggtgacc aagttcatgc tatctcaaat ccagcaacta aaggtatg              48
```

<210> SEQ ID NO 37
<211> LENGTH: 50
<212> TYPE: DNA
<213> ORGANISM: Artificial Sequence
<220> FEATURE:
<223> OTHER INFORMATION: Primer

<400> SEQUENCE: 37

```
gaaggtcgga gtcaacggat taaatctcaa atccagcaac taaaggtata            50
```

<210> SEQ ID NO 38
<211> LENGTH: 28
<212> TYPE: DNA
<213> ORGANISM: Artificial Sequence
<220> FEATURE:
<223> OTHER INFORMATION: Primer

<400> SEQUENCE: 38

```
gtagctccag gcaaatcatg aaagaaaa                                    28
```

<210> SEQ ID NO 39
<211> LENGTH: 44
<212> TYPE: DNA
<213> ORGANISM: Artificial Sequence
<220> FEATURE:
<223> OTHER INFORMATION: Primer

<400> SEQUENCE: 39

```
gaaggtgacc aagttcatgc tgtagtcaca cctaatgcca cgtt                  44
```

<210> SEQ ID NO 40
<211> LENGTH: 44
<212> TYPE: DNA
<213> ORGANISM: Artificial Sequence
<220> FEATURE:
<223> OTHER INFORMATION: Primer

<400> SEQUENCE: 40

```
gaaggtcgga gtcaacggat tgtagtcaca cctaatgcca cgta                  44
```

<210> SEQ ID NO 41
<211> LENGTH: 25
<212> TYPE: DNA
<213> ORGANISM: Artificial Sequence
<220> FEATURE:
<223> OTHER INFORMATION: Primer

<400> SEQUENCE: 41
tgagcacgag cactgaatct cactt                                        25

<210> SEQ ID NO 42
<211> LENGTH: 46
<212> TYPE: DNA
<213> ORGANISM: Artificial Sequence
<220> FEATURE:
<223> OTHER INFORMATION: Primer

<400> SEQUENCE: 42
gaaggtgacc aagttcatgc tgttgtagct ttgccaagtt tcttcg                 46

<210> SEQ ID NO 43
<211> LENGTH: 46
<212> TYPE: DNA
<213> ORGANISM: Artificial Sequence
<220> FEATURE:
<223> OTHER INFORMATION: Primer

<400> SEQUENCE: 43
gaaggtcgga gtcaacggat tgttgtagct ttgccaagtt tcttcc                 46

<210> SEQ ID NO 44
<211> LENGTH: 30
<212> TYPE: DNA
<213> ORGANISM: Artificial Sequence
<220> FEATURE:
<223> OTHER INFORMATION: Primer

<400> SEQUENCE: 44
ctaggatata aatatgcaag tgggtagaat                                   30

<210> SEQ ID NO 45
<211> LENGTH: 57
<212> TYPE: DNA
<213> ORGANISM: Artificial Sequence
<220> FEATURE:
<223> OTHER INFORMATION: Primer

<400> SEQUENCE: 45
gaaggtgacc aagttcatgc tattatttgt atacataatg ttatgttatt tgtgttg     57

<210> SEQ ID NO 46
<211> LENGTH: 58
<212> TYPE: DNA
<213> ORGANISM: Artificial Sequence
<220> FEATURE:
<223> OTHER INFORMATION: Primer

<400> SEQUENCE: 46
gaaggtcgga gtcaacggat tcattatttg tatacataat gttatgttat ttgtgtta    58

<210> SEQ ID NO 47
<211> LENGTH: 30
<212> TYPE: DNA
<213> ORGANISM: Artificial Sequence
<220> FEATURE:
<223> OTHER INFORMATION: Primer

```
<400> SEQUENCE: 47
ctgttattgt tasgaagaaa cttggcaaag                                    30

<210> SEQ ID NO 48
<211> LENGTH: 44
<212> TYPE: DNA
<213> ORGANISM: Artificial Sequence
<220> FEATURE:
<223> OTHER INFORMATION: Primer

<400> SEQUENCE: 48
gaaggtgacc aagttcatgc tttacggtgc ttctactctt agca                    44

<210> SEQ ID NO 49
<211> LENGTH: 43
<212> TYPE: DNA
<213> ORGANISM: Artificial Sequence
<220> FEATURE:
<223> OTHER INFORMATION: Primer

<400> SEQUENCE: 49
gaaggtcgga gtcaacggat ttacggtgct tctactctta gcg                     43

<210> SEQ ID NO 50
<211> LENGTH: 26
<212> TYPE: DNA
<213> ORGANISM: Artificial Sequence
<220> FEATURE:
<223> OTHER INFORMATION: Primer

<400> SEQUENCE: 50
gcagcgatgg ctaaaaggtt gttgtt                                        26

<210> SEQ ID NO 51
<211> LENGTH: 44
<212> TYPE: DNA
<213> ORGANISM: Artificial Sequence
<220> FEATURE:
<223> OTHER INFORMATION: Primer

<400> SEQUENCE: 51
gaaggtgacc aagttcatgc tgtacgtcgt cgtgtcctag tttc                    44

<210> SEQ ID NO 52
<211> LENGTH: 44
<212> TYPE: DNA
<213> ORGANISM: Artificial Sequence
<220> FEATURE:
<223> OTHER INFORMATION: Primer

<400> SEQUENCE: 52
gaaggtcgga gtcaacggat tgtacgtcgt cgtgtcctag tttt                    44

<210> SEQ ID NO 53
<211> LENGTH: 30
<212> TYPE: DNA
<213> ORGANISM: Artificial Sequence
<220> FEATURE:
<223> OTHER INFORMATION: Primer

<400> SEQUENCE: 53
attgtgagga tggaagaaaa tgaatgcaaa                                    30

<210> SEQ ID NO 54
```

<210> SEQ ID NO 54
<211> LENGTH: 44
<212> TYPE: DNA
<213> ORGANISM: Artificial Sequence
<220> FEATURE:
<223> OTHER INFORMATION: Primer

<400> SEQUENCE: 54
gaaggtgacc aagttcatgc tcttggttct tcatttacc atga            44

<210> SEQ ID NO 55
<211> LENGTH: 47
<212> TYPE: DNA
<213> ORGANISM: Artificial Sequence
<220> FEATURE:
<223> OTHER INFORMATION: Primer

<400> SEQUENCE: 55
gaaggtcgga gtcaacggat tgctcttggt tctttcattt accatgg         47

<210> SEQ ID NO 56
<211> LENGTH: 25
<212> TYPE: DNA
<213> ORGANISM: Artificial Sequence
<220> FEATURE:
<223> OTHER INFORMATION: Primer

<400> SEQUENCE: 56
ccgtgatagc acctatatgc agcaa                                 25

<210> SEQ ID NO 57
<211> LENGTH: 42
<212> TYPE: DNA
<213> ORGANISM: Artificial Sequence
<220> FEATURE:
<223> OTHER INFORMATION: Primer

<400> SEQUENCE: 57
gaaggtgacc aagttcatgc tccacctcgt caactccgaa ac              42

<210> SEQ ID NO 58
<211> LENGTH: 44
<212> TYPE: DNA
<213> ORGANISM: Artificial Sequence
<220> FEATURE:
<223> OTHER INFORMATION: Primer

<400> SEQUENCE: 58
gaaggtcgga gtcaacggat tatccacctc gtcaactccg aaat            44

<210> SEQ ID NO 59
<211> LENGTH: 25
<212> TYPE: DNA
<213> ORGANISM: Artificial Sequence
<220> FEATURE:
<223> OTHER INFORMATION: Primer

<400> SEQUENCE: 59
ccttggaagg gttgagattt gggtt                                 25

<210> SEQ ID NO 60
<211> LENGTH: 43
<212> TYPE: DNA
<213> ORGANISM: Artificial Sequence
<220> FEATURE:
<223> OTHER INFORMATION: Primer

<400> SEQUENCE: 60

```
gaaggtgacc aagttcatgc tggccttccc ttgtcttgct tca          43
```

<210> SEQ ID NO 61
<211> LENGTH: 42
<212> TYPE: DNA
<213> ORGANISM: Artificial Sequence
<220> FEATURE:
<223> OTHER INFORMATION: Primer

<400> SEQUENCE: 61

```
gaaggtcgga gtcaacggat tgccttccct tgtcttgctt cg           42
```

<210> SEQ ID NO 62
<211> LENGTH: 29
<212> TYPE: DNA
<213> ORGANISM: Artificial Sequence
<220> FEATURE:
<223> OTHER INFORMATION: Primer

<400> SEQUENCE: 62

```
agtagatatc caaccaagag catgagttt                          29
```

<210> SEQ ID NO 63
<211> LENGTH: 49
<212> TYPE: DNA
<213> ORGANISM: Artificial Sequence
<220> FEATURE:
<223> OTHER INFORMATION: Primer

<400> SEQUENCE: 63

```
gaaggtgacc aagttcatgc tcgtctgcat atctatataa aacatgtcg    49
```

<210> SEQ ID NO 64
<211> LENGTH: 50
<212> TYPE: DNA
<213> ORGANISM: Artificial Sequence
<220> FEATURE:
<223> OTHER INFORMATION: Primer

<400> SEQUENCE: 64

```
gaaggtcgga gtcaacggat tccgtctgca tatctatata aaacatgtca   50
```

<210> SEQ ID NO 65
<211> LENGTH: 25
<212> TYPE: DNA
<213> ORGANISM: Artificial Sequence
<220> FEATURE:
<223> OTHER INFORMATION: Primer

<400> SEQUENCE: 65

```
attgttcacc ggtaatgccg acgaa                              25
```

<210> SEQ ID NO 66
<211> LENGTH: 47
<212> TYPE: DNA
<213> ORGANISM: Artificial Sequence
<220> FEATURE:
<223> OTHER INFORMATION: Primer

<400> SEQUENCE: 66

```
gaaggtgacc aagttcatgc tcgttgtttg agcaacggac aattgat      47
```

<210> SEQ ID NO 67
<211> LENGTH: 46
<212> TYPE: DNA

```
<213> ORGANISM: Artificial Sequence
<220> FEATURE:
<223> OTHER INFORMATION: Primer

<400> SEQUENCE: 67
gaaggtcgga gtcaacggat tgttgtttga gcaacggaca attgag                    46

<210> SEQ ID NO 68
<211> LENGTH: 26
<212> TYPE: DNA
<213> ORGANISM: Artificial Sequence
<220> FEATURE:
<223> OTHER INFORMATION: Primer

<400> SEQUENCE: 68
gggtctgccc aaatccattt caactt                                          26

<210> SEQ ID NO 69
<211> LENGTH: 45
<212> TYPE: DNA
<213> ORGANISM: Artificial Sequence
<220> FEATURE:
<223> OTHER INFORMATION: Primer

<400> SEQUENCE: 69
gaaggtgacc aagttcatgc ttccacagtc tcctagggtt aattg                     45

<210> SEQ ID NO 70
<211> LENGTH: 44
<212> TYPE: DNA
<213> ORGANISM: Artificial Sequence
<220> FEATURE:
<223> OTHER INFORMATION: Primer

<400> SEQUENCE: 70
gaaggtcgga gtcaacggat tccacagtct cctagggtta attc                      44

<210> SEQ ID NO 71
<211> LENGTH: 25
<212> TYPE: DNA
<213> ORGANISM: Artificial Sequence
<220> FEATURE:
<223> OTHER INFORMATION: Primer

<400> SEQUENCE: 71
tgctctcagt gccccagata ttcat                                           25

<210> SEQ ID NO 72
<211> LENGTH: 40
<212> TYPE: DNA
<213> ORGANISM: Artificial Sequence
<220> FEATURE:
<223> OTHER INFORMATION: Primer

<400> SEQUENCE: 72
gaaggtgacc aagttcatgc tccgaatgct tcaccaccgt                           40

<210> SEQ ID NO 73
<211> LENGTH: 42
<212> TYPE: DNA
<213> ORGANISM: Artificial Sequence
<220> FEATURE:
<223> OTHER INFORMATION: Primer

<400> SEQUENCE: 73
gaaggtcgga gtcaacggat tctccgaatg cttcaccacc gc                        42
```

<210> SEQ ID NO 74
<211> LENGTH: 25
<212> TYPE: DNA
<213> ORGANISM: Artificial Sequence
<220> FEATURE:
<223> OTHER INFORMATION: Primer

<400> SEQUENCE: 74
gcttgggaga gtggattatg ctctt                                           25

<210> SEQ ID NO 75
<211> LENGTH: 51
<212> TYPE: DNA
<213> ORGANISM: Artificial Sequence
<220> FEATURE:
<223> OTHER INFORMATION: Primer

<400> SEQUENCE: 75
gaaggtgacc aagttcatgc ttttgcagtc tgtactaaaa ttgatgatat a              51

<210> SEQ ID NO 76
<211> LENGTH: 49
<212> TYPE: DNA
<213> ORGANISM: Artificial Sequence
<220> FEATURE:
<223> OTHER INFORMATION: Primer

<400> SEQUENCE: 76
gaaggtcgga gtcaacggat tgcagtctg tactaaaatt gatgatatc                  49

<210> SEQ ID NO 77
<211> LENGTH: 24
<212> TYPE: DNA
<213> ORGANISM: Artificial Sequence
<220> FEATURE:
<223> OTHER INFORMATION: Primer

<400> SEQUENCE: 77
cttagtggga gctatgtgcg acaa                                            24

<210> SEQ ID NO 78
<211> LENGTH: 49
<212> TYPE: DNA
<213> ORGANISM: Artificial Sequence
<220> FEATURE:
<223> OTHER INFORMATION: Primer

<400> SEQUENCE: 78
gaaggtgacc aagttcatgc tcatgtgttt tctttaggtt ttctcgttg                 49

<210> SEQ ID NO 79
<211> LENGTH: 50
<212> TYPE: DNA
<213> ORGANISM: Artificial Sequence
<220> FEATURE:
<223> OTHER INFORMATION: Primer

<400> SEQUENCE: 79
gaaggtcgga gtcaacggat tccatgtgtt tctttaggt tttctcgtta                 50

<210> SEQ ID NO 80
<211> LENGTH: 25
<212> TYPE: DNA
<213> ORGANISM: Artificial Sequence
<220> FEATURE:

```
<223> OTHER INFORMATION: Primer

<400> SEQUENCE: 80
aaacccccca tcctttgagg actaa                                           25

<210> SEQ ID NO 81
<211> LENGTH: 47
<212> TYPE: DNA
<213> ORGANISM: Artificial Sequence
<220> FEATURE:
<223> OTHER INFORMATION: Primer

<400> SEQUENCE: 81
gaaggtgacc aagttcatgc tatgtttgtt tcactcaggt ctttctc                   47

<210> SEQ ID NO 82
<211> LENGTH: 48
<212> TYPE: DNA
<213> ORGANISM: Artificial Sequence
<220> FEATURE:
<223> OTHER INFORMATION: Primer

<400> SEQUENCE: 82
gaaggtcgga gtcaacggat tcatgtttgt ttcactcagg tctttctt                  48

<210> SEQ ID NO 83
<211> LENGTH: 30
<212> TYPE: DNA
<213> ORGANISM: Artificial Sequence
<220> FEATURE:
<223> OTHER INFORMATION: Primer

<400> SEQUENCE: 83
gtgtttgaat gatgcatata aaatggtgta                                      30

<210> SEQ ID NO 84
<211> LENGTH: 44
<212> TYPE: DNA
<213> ORGANISM: Artificial Sequence
<220> FEATURE:
<223> OTHER INFORMATION: Primer

<400> SEQUENCE: 84
gaaggtgacc aagttcatgc tttgtgtaat gtgggagtgc catg                      44

<210> SEQ ID NO 85
<211> LENGTH: 46
<212> TYPE: DNA
<213> ORGANISM: Artificial Sequence
<220> FEATURE:
<223> OTHER INFORMATION: Primer

<400> SEQUENCE: 85
gaaggtcgga gtcaacggat tgtttgtgta atgtgggagt gccata                    46

<210> SEQ ID NO 86
<211> LENGTH: 29
<212> TYPE: DNA
<213> ORGANISM: Artificial Sequence
<220> FEATURE:
<223> OTHER INFORMATION: Primer

<400> SEQUENCE: 86
gaatcagagt tgggaatgaa gccttatta                                       29
```

<210> SEQ ID NO 87
<211> LENGTH: 45
<212> TYPE: DNA
<213> ORGANISM: Artificial Sequence
<220> FEATURE:
<223> OTHER INFORMATION: Primer

<400> SEQUENCE: 87
gaaggtgacc aagttcatgc tgtgtactgc cacactctct tctta          45

<210> SEQ ID NO 88
<211> LENGTH: 43
<212> TYPE: DNA
<213> ORGANISM: Artificial Sequence
<220> FEATURE:
<223> OTHER INFORMATION: Primer

<400> SEQUENCE: 88
gaaggtcgga gtcaacggat tgtactgcca cactctcttc ttg            43

<210> SEQ ID NO 89
<211> LENGTH: 25
<212> TYPE: DNA
<213> ORGANISM: Artificial Sequence
<220> FEATURE:
<223> OTHER INFORMATION: Primer

<400> SEQUENCE: 89
gcagagacct ttgtagtcca gtctt                                25

<210> SEQ ID NO 90
<211> LENGTH: 42
<212> TYPE: DNA
<213> ORGANISM: Artificial Sequence
<220> FEATURE:
<223> OTHER INFORMATION: Primer

<400> SEQUENCE: 90
gaaggtgacc aagttcatgc tctcctctct caaggaattg ag             42

<210> SEQ ID NO 91
<211> LENGTH: 46
<212> TYPE: DNA
<213> ORGANISM: Artificial Sequence
<220> FEATURE:
<223> OTHER INFORMATION: Primer

<400> SEQUENCE: 91
gaaggtcgga gtcaacggat tacctctcct ctctcaagga attgat         46

<210> SEQ ID NO 92
<211> LENGTH: 23
<212> TYPE: DNA
<213> ORGANISM: Artificial Sequence
<220> FEATURE:
<223> OTHER INFORMATION: Primer

<400> SEQUENCE: 92
gcagaccctc ctctggtaag cat                                  23

<210> SEQ ID NO 93
<211> LENGTH: 43
<212> TYPE: DNA
<213> ORGANISM: Artificial Sequence
<220> FEATURE:
<223> OTHER INFORMATION: Primer

<400> SEQUENCE: 93
gaaggtgacc aagttcatgc tgaacccat tgccactaac tgc                43

<210> SEQ ID NO 94
<211> LENGTH: 44
<212> TYPE: DNA
<213> ORGANISM: Artificial Sequence
<220> FEATURE:
<223> OTHER INFORMATION: Primer

<400> SEQUENCE: 94
gaaggtcgga gtcaacggat tagaaccca ttgccactaa ctgt                44

<210> SEQ ID NO 95
<211> LENGTH: 29
<212> TYPE: DNA
<213> ORGANISM: Artificial Sequence
<220> FEATURE:
<223> OTHER INFORMATION: Primer

<400> SEQUENCE: 95
acctaatgtc gagaaagcta gaatcactt                29

<210> SEQ ID NO 96
<211> LENGTH: 47
<212> TYPE: DNA
<213> ORGANISM: Artificial Sequence
<220> FEATURE:
<223> OTHER INFORMATION: Primer

<400> SEQUENCE: 96
gaaggtgacc aagttcatgc tcacataaat accgctaaaa cacgcac                47

<210> SEQ ID NO 97
<211> LENGTH: 47
<212> TYPE: DNA
<213> ORGANISM: Artificial Sequence
<220> FEATURE:
<223> OTHER INFORMATION: Primer

<400> SEQUENCE: 97
gaaggtcgga gtcaacggat tcacataaat accgctaaaa cacgcat                47

<210> SEQ ID NO 98
<211> LENGTH: 29
<212> TYPE: DNA
<213> ORGANISM: Artificial Sequence
<220> FEATURE:
<223> OTHER INFORMATION: Primer

<400> SEQUENCE: 98
acagaagatc gctggttagt agttagtta                29

<210> SEQ ID NO 99
<211> LENGTH: 41
<212> TYPE: DNA
<213> ORGANISM: Artificial Sequence
<220> FEATURE:
<223> OTHER INFORMATION: Primer

<400> SEQUENCE: 99
gaaggtgacc aagttcatgc tcgtctacgg cgaatcgagc g                41

<210> SEQ ID NO 100
<211> LENGTH: 41

```
<212> TYPE: DNA
<213> ORGANISM: Artificial Sequence
<220> FEATURE:
<223> OTHER INFORMATION: Primer

<400> SEQUENCE: 100
gaaggtcgga gtcaacggat tcgtctacgg cgaatcgagc a                    41

<210> SEQ ID NO 101
<211> LENGTH: 25
<212> TYPE: DNA
<213> ORGANISM: Artificial Sequence
<220> FEATURE:
<223> OTHER INFORMATION: Primer

<400> SEQUENCE: 101
ctctcaaaac agcgtcgaaa ccgaa                                      25

<210> SEQ ID NO 102
<211> LENGTH: 49
<212> TYPE: DNA
<213> ORGANISM: Artificial Sequence
<220> FEATURE:
<223> OTHER INFORMATION: Primer

<400> SEQUENCE: 102
gaaggtgacc aagttcatgc tgtaaccttt cagcattgta taaagttcg            49

<210> SEQ ID NO 103
<211> LENGTH: 49
<212> TYPE: DNA
<213> ORGANISM: Artificial Sequence
<220> FEATURE:
<223> OTHER INFORMATION: Primer

<400> SEQUENCE: 103
gaaggtcgga gtcaacggat tgtaaccttt cagcattgta taaagttcc            49

<210> SEQ ID NO 104
<211> LENGTH: 25
<212> TYPE: DNA
<213> ORGANISM: Artificial Sequence
<220> FEATURE:
<223> OTHER INFORMATION: Primer

<400> SEQUENCE: 104
ttcaggttgg aagatgatca agcaa                                      25

<210> SEQ ID NO 105
<211> LENGTH: 45
<212> TYPE: DNA
<213> ORGANISM: Artificial Sequence
<220> FEATURE:
<223> OTHER INFORMATION: Primer

<400> SEQUENCE: 105
gaaggtgacc aagttcatgc tggacatctg tttcaggttg gaaga                45

<210> SEQ ID NO 106
<211> LENGTH: 45
<212> TYPE: DNA
<213> ORGANISM: Artificial Sequence
<220> FEATURE:
<223> OTHER INFORMATION: Primer

<400> SEQUENCE: 106
```

```
gaaggtcgga gtcaacggat tggacatctg tttcaggttg gaagt          45
```

<210> SEQ ID NO 107
<211> LENGTH: 29
<212> TYPE: DNA
<213> ORGANISM: Artificial Sequence
<220> FEATURE:
<223> OTHER INFORMATION: Primer

<400> SEQUENCE: 107

```
acgggttgtc ttcggtatat tttttgctt                             29
```

<210> SEQ ID NO 108
<211> LENGTH: 45
<212> TYPE: DNA
<213> ORGANISM: Artificial Sequence
<220> FEATURE:
<223> OTHER INFORMATION: Primer

<400> SEQUENCE: 108

```
gaaggtgacc aagttcatgc taattatacc taggagactg tggag          45
```

<210> SEQ ID NO 109
<211> LENGTH: 45
<212> TYPE: DNA
<213> ORGANISM: Artificial Sequence
<220> FEATURE:
<223> OTHER INFORMATION: Primer

<400> SEQUENCE: 109

```
gaaggtcgga gtcaacggat taattatacc taggagactg tggaa          45
```

<210> SEQ ID NO 110
<211> LENGTH: 21
<212> TYPE: DNA
<213> ORGANISM: Artificial Sequence
<220> FEATURE:
<223> OTHER INFORMATION: Primer

<400> SEQUENCE: 110

```
gctgcctcca cgttgtgacc t                                    21
```

<210> SEQ ID NO 111
<211> LENGTH: 47
<212> TYPE: DNA
<213> ORGANISM: Artificial Sequence
<220> FEATURE:
<223> OTHER INFORMATION: Primer

<400> SEQUENCE: 111

```
gaaggtgacc aagttcatgc tcatgcacag ttgctatgat ttccttg        47
```

<210> SEQ ID NO 112
<211> LENGTH: 47
<212> TYPE: DNA
<213> ORGANISM: Artificial Sequence
<220> FEATURE:
<223> OTHER INFORMATION: Primer

<400> SEQUENCE: 112

```
gaaggtcgga gtcaacggat tcatgcacag ttgctatgat ttccttc        47
```

<210> SEQ ID NO 113
<211> LENGTH: 22
<212> TYPE: DNA
<213> ORGANISM: Artificial Sequence
<220> FEATURE:
<223> OTHER INFORMATION: Primer

<400> SEQUENCE: 113
cgcagccacc tttgatgcgc aa                                              22

<210> SEQ ID NO 114
<211> LENGTH: 43
<212> TYPE: DNA
<213> ORGANISM: Artificial Sequence
<220> FEATURE:
<223> OTHER INFORMATION: Primer

<400> SEQUENCE: 114
gaaggtgacc aagttcatgc tgcagccacc attgatgtcc aag                       43

<210> SEQ ID NO 115
<211> LENGTH: 43
<212> TYPE: DNA
<213> ORGANISM: Artificial Sequence
<220> FEATURE:
<223> OTHER INFORMATION: Primer

<400> SEQUENCE: 115
gaaggtcgga gtcaacggat tgcagccacc attgatgtcc aac                       43

<210> SEQ ID NO 116
<211> LENGTH: 27
<212> TYPE: DNA
<213> ORGANISM: Artificial Sequence
<220> FEATURE:
<223> OTHER INFORMATION: Primer

<400> SEQUENCE: 116
cccatgcaca gttgctatga tttcctt                                         27

<210> SEQ ID NO 117
<211> LENGTH: 42
<212> TYPE: DNA
<213> ORGANISM: Artificial Sequence
<220> FEATURE:
<223> OTHER INFORMATION: Primer

<400> SEQUENCE: 117
gaaggtgacc aagttcatgc tattcgagcc tggggcagtc at                        42

<210> SEQ ID NO 118
<211> LENGTH: 39
<212> TYPE: DNA
<213> ORGANISM: Artificial Sequence
<220> FEATURE:
<223> OTHER INFORMATION: Primer

<400> SEQUENCE: 118
gaaggtcgga gtcaacggat tcgagcctgg ggcagtcaa                            39

<210> SEQ ID NO 119
<211> LENGTH: 22
<212> TYPE: DNA
<213> ORGANISM: Artificial Sequence
<220> FEATURE:
<223> OTHER INFORMATION: Primer

<400> SEQUENCE: 119
aggtctctgc cacctctcct ct                                              22

<210> SEQ ID NO 120
<211> LENGTH: 48
<212> TYPE: DNA
<213> ORGANISM: Artificial Sequence
<220> FEATURE:
<223> OTHER INFORMATION: Primer

<400> SEQUENCE: 120
gaaggtgacc aagttcatgc tgtatactcc agcaatgttc aaactgaa        48

<210> SEQ ID NO 121
<211> LENGTH: 48
<212> TYPE: DNA
<213> ORGANISM: Artificial Sequence
<220> FEATURE:
<223> OTHER INFORMATION: Primer

<400> SEQUENCE: 121
gaaggtcgga gtcaacggat tgtatactcc agcaatgttc aaactgat        48

<210> SEQ ID NO 122
<211> LENGTH: 29
<212> TYPE: DNA
<213> ORGANISM: Artificial Sequence
<220> FEATURE:
<223> OTHER INFORMATION: Primer

<400> SEQUENCE: 122
gtcattatag aaacactttg cagcaccaa                             29

<210> SEQ ID NO 123
<211> LENGTH: 47
<212> TYPE: DNA
<213> ORGANISM: Artificial Sequence
<220> FEATURE:
<223> OTHER INFORMATION: Primer

<400> SEQUENCE: 123
gaaggtgacc aagttcatgc ttatagaaac actttgcagc accaaag         47

<210> SEQ ID NO 124
<211> LENGTH: 50
<212> TYPE: DNA
<213> ORGANISM: Artificial Sequence
<220> FEATURE:
<223> OTHER INFORMATION: Primer

<400> SEQUENCE: 124
gaaggtcgga gtcaacggat tcattataga aacactttgc agcaccaaaa      50

<210> SEQ ID NO 125
<211> LENGTH: 28
<212> TYPE: DNA
<213> ORGANISM: Artificial Sequence
<220> FEATURE:
<223> OTHER INFORMATION: Primer

<400> SEQUENCE: 125
acaagggtat actccagcaa tgttcaaa                              28

<210> SEQ ID NO 126
<211> LENGTH: 48
<212> TYPE: DNA
<213> ORGANISM: Artificial Sequence
<220> FEATURE:
<223> OTHER INFORMATION: Primer

<400> SEQUENCE: 126
gaaggtgacc aagttcatgc tgtatactcc agcaatgttc aaactgat            48

<210> SEQ ID NO 127
<211> LENGTH: 48
<212> TYPE: DNA
<213> ORGANISM: Artificial Sequence
<220> FEATURE:
<223> OTHER INFORMATION: Primer

<400> SEQUENCE: 127
gaaggtcgga gtcaacggat tgtatactcc agcaatgttc aaactgaa            48

<210> SEQ ID NO 128
<211> LENGTH: 29
<212> TYPE: DNA
<213> ORGANISM: Artificial Sequence
<220> FEATURE:
<223> OTHER INFORMATION: Primer

<400> SEQUENCE: 128
gtcattatag aaacactttg cagcaccaa                                 29

<210> SEQ ID NO 129
<211> LENGTH: 25
<212> TYPE: DNA
<213> ORGANISM: Artificial Sequence
<220> FEATURE:
<223> OTHER INFORMATION: Primer

<400> SEQUENCE: 129
gctccaggca aatcatgaaa gaaaa                                     25

<210> SEQ ID NO 130
<211> LENGTH: 25
<212> TYPE: DNA
<213> ORGANISM: Artificial Sequence
<220> FEATURE:
<223> OTHER INFORMATION: Primer

<400> SEQUENCE: 130
ctgtgacaac taatgaaggg agtca                                     25

<210> SEQ ID NO 131
<211> LENGTH: 22
<212> TYPE: DNA
<213> ORGANISM: Artificial Sequence
<220> FEATURE:
<223> OTHER INFORMATION: Primer

<400> SEQUENCE: 131
cacgagcact gaatctcact tg                                        22

<210> SEQ ID NO 132
<211> LENGTH: 33
<212> TYPE: DNA
<213> ORGANISM: Artificial Sequence
<220> FEATURE:
<223> OTHER INFORMATION: Primer

<400> SEQUENCE: 132
tgcatattta tatcctagtg tagtcacacc taa                            33

<210> SEQ ID NO 133

```
<211> LENGTH: 32
<212> TYPE: DNA
<213> ORGANISM: Artificial Sequence
<220> FEATURE:
<223> OTHER INFORMATION: Primer

<400> SEQUENCE: 133
gtgtgactac actaggatat aaatatgcaa gt                                    32

<210> SEQ ID NO 134
<211> LENGTH: 33
<212> TYPE: DNA
<213> ORGANISM: Artificial Sequence
<220> FEATURE:
<223> OTHER INFORMATION: Primer

<400> SEQUENCE: 134
cataatgtta tgttatttgt gttgtagctt tgc                                   33

<210> SEQ ID NO 135
<211> LENGTH: 31
<212> TYPE: DNA
<213> ORGANISM: Artificial Sequence
<220> FEATURE:
<223> OTHER INFORMATION: Primer

<400> SEQUENCE: 135
acactaggat ataaatatgc aagtgggtag a                                     31

<210> SEQ ID NO 136
<211> LENGTH: 26
<212> TYPE: DNA
<213> ORGANISM: Artificial Sequence
<220> FEATURE:
<223> OTHER INFORMATION: Primer

<400> SEQUENCE: 136
ctggttattt gctctcattt gccatt                                           26

<210> SEQ ID NO 137
<211> LENGTH: 22
<212> TYPE: DNA
<213> ORGANISM: Artificial Sequence
<220> FEATURE:
<223> OTHER INFORMATION: Primer

<400> SEQUENCE: 137
tggctttgga gaactttacg gt                                               22

<210> SEQ ID NO 138
<211> LENGTH: 20
<212> TYPE: DNA
<213> ORGANISM: Artificial Sequence
<220> FEATURE:
<223> OTHER INFORMATION: Primer

<400> SEQUENCE: 138
ggtcaggagg gagaattgga                                                  20

<210> SEQ ID NO 139
<211> LENGTH: 20
<212> TYPE: DNA
<213> ORGANISM: Artificial Sequence
<220> FEATURE:
<223> OTHER INFORMATION: Primer

<400> SEQUENCE: 139
```
gccgcaatct ccctcctcat                                                        20

<210> SEQ ID NO 140
<211> LENGTH: 20
<212> TYPE: DNA
<213> ORGANISM: Artificial Sequence
<220> FEATURE:
<223> OTHER INFORMATION: Primer

<400> SEQUENCE: 140
acggcacctt ggaagggttg                                                        20

<210> SEQ ID NO 141
<211> LENGTH: 22
<212> TYPE: DNA
<213> ORGANISM: Artificial Sequence
<220> FEATURE:
<223> OTHER INFORMATION: Primer

<400> SEQUENCE: 141
ctcaaacttg tccccataga gc                                                     22

<210> SEQ ID NO 142
<211> LENGTH: 24
<212> TYPE: DNA
<213> ORGANISM: Artificial Sequence
<220> FEATURE:
<223> OTHER INFORMATION: Primer

<400> SEQUENCE: 142
cttcacatat ggaaccacag caac                                                   24

<210> SEQ ID NO 143
<211> LENGTH: 22
<212> TYPE: DNA
<213> ORGANISM: Artificial Sequence
<220> FEATURE:
<223> OTHER INFORMATION: Primer

<400> SEQUENCE: 143
caggttggaa gatgatcaag ca                                                     22

<210> SEQ ID NO 144
<211> LENGTH: 22
<212> TYPE: DNA
<213> ORGANISM: Artificial Sequence
<220> FEATURE:
<223> OTHER INFORMATION: Primer

<400> SEQUENCE: 144
tgtgcgtaac ctttcagcat tg                                                     22

<210> SEQ ID NO 145
<211> LENGTH: 18
<212> TYPE: DNA
<213> ORGANISM: Artificial Sequence
<220> FEATURE:
<223> OTHER INFORMATION: Primer

<400> SEQUENCE: 145
gcctccacgt tgtgacct                                                          18

<210> SEQ ID NO 146
<211> LENGTH: 21
<212> TYPE: DNA

```
<213> ORGANISM: Artificial Sequence
<220> FEATURE:
<223> OTHER INFORMATION: Primer

<400> SEQUENCE: 146
gcacttgcca gagcaactat g                                             21

<210> SEQ ID NO 147
<211> LENGTH: 30
<212> TYPE: DNA
<213> ORGANISM: Artificial Sequence
<220> FEATURE:
<223> OTHER INFORMATION: Primer

<400> SEQUENCE: 147
cacaaaacac gcatgataga ataaacttta                                    30

<210> SEQ ID NO 148
<211> LENGTH: 23
<212> TYPE: DNA
<213> ORGANISM: Artificial Sequence
<220> FEATURE:
<223> OTHER INFORMATION: Primer

<400> SEQUENCE: 148
caggtcatga tgtggcctac aag                                           23

<210> SEQ ID NO 149
<211> LENGTH: 22
<212> TYPE: DNA
<213> ORGANISM: Artificial Sequence
<220> FEATURE:
<223> OTHER INFORMATION: Primer

<400> SEQUENCE: 149
gtcataaatt actccaaact tc                                            22

<210> SEQ ID NO 150
<211> LENGTH: 20
<212> TYPE: DNA
<213> ORGANISM: Artificial Sequence
<220> FEATURE:
<223> OTHER INFORMATION: Primer

<400> SEQUENCE: 150
ggcgttcctt tcttcgttct                                               20

<210> SEQ ID NO 151
<211> LENGTH: 18
<212> TYPE: DNA
<213> ORGANISM: Artificial Sequence
<220> FEATURE:
<223> OTHER INFORMATION: Primer

<400> SEQUENCE: 151
aacctcgaga tggagcat                                                 18

<210> SEQ ID NO 152
<211> LENGTH: 20
<212> TYPE: DNA
<213> ORGANISM: Artificial Sequence
<220> FEATURE:
<223> OTHER INFORMATION: Primer

<400> SEQUENCE: 152
gtgttgtttg atgaaatgag                                               20
```

```
<210> SEQ ID NO 153
<211> LENGTH: 18
<212> TYPE: DNA
<213> ORGANISM: Artificial Sequence
<220> FEATURE:
<223> OTHER INFORMATION: Primer

<400> SEQUENCE: 153
tgcagacacc gcctgaat                                                 18

<210> SEQ ID NO 154
<211> LENGTH: 21
<212> TYPE: DNA
<213> ORGANISM: Artificial Sequence
<220> FEATURE:
<223> OTHER INFORMATION: Primer

<400> SEQUENCE: 154
gggcttgtaa acgcactgaa g                                             21

<210> SEQ ID NO 155
<211> LENGTH: 20
<212> TYPE: DNA
<213> ORGANISM: Artificial Sequence
<220> FEATURE:
<223> OTHER INFORMATION: Minimum Identifier

<400> SEQUENCE: 155
aaagtgcatg aatacccttta                                              20

<210> SEQ ID NO 156
<211> LENGTH: 20
<212> TYPE: DNA
<213> ORGANISM: Artificial Sequence
<220> FEATURE:
<223> OTHER INFORMATION: Minimum Identifier

<400> SEQUENCE: 156
aaagtgcatg gatacccttta                                              20

<210> SEQ ID NO 157
<211> LENGTH: 20
<212> TYPE: DNA
<213> ORGANISM: Artificial Sequence
<220> FEATURE:
<223> OTHER INFORMATION: Minimum Identifier

<400> SEQUENCE: 157
tgagagacca aacgtggcat                                               20

<210> SEQ ID NO 158
<211> LENGTH: 20
<212> TYPE: DNA
<213> ORGANISM: Artificial Sequence
<220> FEATURE:
<223> OTHER INFORMATION: Minimum Identifier

<400> SEQUENCE: 158
tgagagacca tacgtggcat                                               20

<210> SEQ ID NO 159
<211> LENGTH: 20
<212> TYPE: DNA
<213> ORGANISM: Artificial Sequence
<220> FEATURE:
```

<223> OTHER INFORMATION: Minimum Identifier

<400> SEQUENCE: 159
gttattgtta cgaagaaact                                               20

<210> SEQ ID NO 160
<211> LENGTH: 20
<212> TYPE: DNA
<213> ORGANISM: Artificial Sequence
<220> FEATURE:
<223> OTHER INFORMATION: Minimum Identifier

<400> SEQUENCE: 160
gttattgtta ggaagaaact                                               20

<210> SEQ ID NO 161
<211> LENGTH: 18
<212> TYPE: DNA
<213> ORGANISM: Artificial Sequence
<220> FEATURE:
<223> OTHER INFORMATION: Minimum Identifier

<400> SEQUENCE: 161
gcaaagctaa cacaaata                                                 18

<210> SEQ ID NO 162
<211> LENGTH: 20
<212> TYPE: DNA
<213> ORGANISM: Artificial Sequence
<220> FEATURE:
<223> OTHER INFORMATION: Minimum Identifier

<400> SEQUENCE: 162
gcaaagctac aacacaaata                                               20

<210> SEQ ID NO 163
<211> LENGTH: 20
<212> TYPE: DNA
<213> ORGANISM: Artificial Sequence
<220> FEATURE:
<223> OTHER INFORMATION: Minimum Identifier

<400> SEQUENCE: 163
tactcttagc gacaataaca                                               20

<210> SEQ ID NO 164
<211> LENGTH: 20
<212> TYPE: DNA
<213> ORGANISM: Artificial Sequence
<220> FEATURE:
<223> OTHER INFORMATION: Minimum Identifier

<400> SEQUENCE: 164
tactcttagc aacaataaca                                               20

<210> SEQ ID NO 165
<211> LENGTH: 20
<212> TYPE: DNA
<213> ORGANISM: Artificial Sequence
<220> FEATURE:
<223> OTHER INFORMATION: Minimum Identifier
<220> FEATURE:
<221> NAME/KEY: misc_feature
<222> LOCATION: (16)..(16)
<223> OTHER INFORMATION: n is a, c, g, or t

<400> SEQUENCE: 165
gtcctagttt tcctgntctc                                           20

<210> SEQ ID NO 166
<211> LENGTH: 20
<212> TYPE: DNA
<213> ORGANISM: Artificial Sequence
<220> FEATURE:
<223> OTHER INFORMATION: Minimum Identifier
<220> FEATURE:
<221> NAME/KEY: misc_feature
<222> LOCATION: (16)..(16)
<223> OTHER INFORMATION: n is a, c, g, or t

<400> SEQUENCE: 166
gtcctagttt ccctgntctc                                           20

<210> SEQ ID NO 167
<211> LENGTH: 20
<212> TYPE: DNA
<213> ORGANISM: Artificial Sequence
<220> FEATURE:
<223> OTHER INFORMATION: Minimum Identifier

<400> SEQUENCE: 167
gaattgctta ccatggtaaa                                           20

<210> SEQ ID NO 168
<211> LENGTH: 20
<212> TYPE: DNA
<213> ORGANISM: Artificial Sequence
<220> FEATURE:
<223> OTHER INFORMATION: Minimum Identifier

<400> SEQUENCE: 168
gaattgctta tcatggtaaa                                           20

<210> SEQ ID NO 169
<211> LENGTH: 20
<212> TYPE: DNA
<213> ORGANISM: Artificial Sequence
<220> FEATURE:
<223> OTHER INFORMATION: Minimum Identifier

<400> SEQUENCE: 169
aactccgaaa tggaacccaa                                           20

<210> SEQ ID NO 170
<211> LENGTH: 20
<212> TYPE: DNA
<213> ORGANISM: Artificial Sequence
<220> FEATURE:
<223> OTHER INFORMATION: Minimum Identifier

<400> SEQUENCE: 170
aactccgaaa cggaacccaa                                           20

<210> SEQ ID NO 171
<211> LENGTH: 20
<212> TYPE: DNA
<213> ORGANISM: Artificial Sequence
<220> FEATURE:
<223> OTHER INFORMATION: Minimum Identifier

<400> SEQUENCE: 171
gtcttgcttc gacaaactca                                           20

```
<210> SEQ ID NO 172
<211> LENGTH: 20
<212> TYPE: DNA
<213> ORGANISM: Artificial Sequence
<220> FEATURE:
<223> OTHER INFORMATION: Minimum Identifier

<400> SEQUENCE: 172
gtcttgcttc aacaaactca                                               20

<210> SEQ ID NO 173
<211> LENGTH: 20
<212> TYPE: DNA
<213> ORGANISM: Artificial Sequence
<220> FEATURE:
<223> OTHER INFORMATION: Minimum Identifier

<400> SEQUENCE: 173
aaaacatgtc atcgtcttcg                                               20

<210> SEQ ID NO 174
<211> LENGTH: 20
<212> TYPE: DNA
<213> ORGANISM: Artificial Sequence
<220> FEATURE:
<223> OTHER INFORMATION: Minimum Identifier

<400> SEQUENCE: 174
aaaacatgtc gtcgtcttcg                                               20

<210> SEQ ID NO 175
<211> LENGTH: 20
<212> TYPE: DNA
<213> ORGANISM: Artificial Sequence
<220> FEATURE:
<223> OTHER INFORMATION: Minimum Identifier
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t

<400> SEQUENCE: 175
ggacaattga gaatncncaa                                               20

<210> SEQ ID NO 176
<211> LENGTH: 20
<212> TYPE: DNA
<213> ORGANISM: Artificial Sequence
<220> FEATURE:
<223> OTHER INFORMATION: Minimum Identifier
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t

<400> SEQUENCE: 176
ggacaattga taatncncaa                                               20

<210> SEQ ID NO 177
<211> LENGTH: 20
```

```
<212> TYPE: DNA
<213> ORGANISM: Artificial Sequence
<220> FEATURE:
<223> OTHER INFORMATION: Minimum Identifier

<400> SEQUENCE: 177
agggttaatt catgaatatc                                              20

<210> SEQ ID NO 178
<211> LENGTH: 20
<212> TYPE: DNA
<213> ORGANISM: Artificial Sequence
<220> FEATURE:
<223> OTHER INFORMATION: Minimum Identifier

<400> SEQUENCE: 178
agggttaatt gatgaatatc                                              20

<210> SEQ ID NO 179
<211> LENGTH: 20
<212> TYPE: DNA
<213> ORGANISM: Artificial Sequence
<220> FEATURE:
<223> OTHER INFORMATION: Minimum Identifier
<220> FEATURE:
<221> NAME/KEY: misc_feature
<222> LOCATION: (7)..(7)
<223> OTHER INFORMATION: n is a, c, g, or t

<400> SEQUENCE: 179
cggcggnggt gcggtggtga                                              20

<210> SEQ ID NO 180
<211> LENGTH: 20
<212> TYPE: DNA
<213> ORGANISM: Artificial Sequence
<220> FEATURE:
<223> OTHER INFORMATION: Minimum Identifier
<220> FEATURE:
<221> NAME/KEY: misc_feature
<222> LOCATION: (7)..(7)
<223> OTHER INFORMATION: n is a, c, g, or t

<400> SEQUENCE: 180
cggcggnggt acggtggtga                                              20

<210> SEQ ID NO 181
<211> LENGTH: 20
<212> TYPE: DNA
<213> ORGANISM: Artificial Sequence
<220> FEATURE:
<223> OTHER INFORMATION: Minimum Identifier

<400> SEQUENCE: 181
ttgatgatat cttgtcgcac                                              20

<210> SEQ ID NO 182
<211> LENGTH: 20
<212> TYPE: DNA
<213> ORGANISM: Artificial Sequence
<220> FEATURE:
<223> OTHER INFORMATION: Minimum Identifier

<400> SEQUENCE: 182
ttgatgatat attgtcgcac                                              20

<210> SEQ ID NO 183
```

```
<211> LENGTH: 20
<212> TYPE: DNA
<213> ORGANISM: Artificial Sequence
<220> FEATURE:
<223> OTHER INFORMATION: Minimum Identifier

<400> SEQUENCE: 183
ttttctcgtt atggtctgtt                                               20

<210> SEQ ID NO 184
<211> LENGTH: 20
<212> TYPE: DNA
<213> ORGANISM: Artificial Sequence
<220> FEATURE:
<223> OTHER INFORMATION: Minimum Identifier

<400> SEQUENCE: 184
ttttctcgtt gtggtctgtt                                               20

<210> SEQ ID NO 185
<211> LENGTH: 20
<212> TYPE: DNA
<213> ORGANISM: Artificial Sequence
<220> FEATURE:
<223> OTHER INFORMATION: Minimum Identifier
<220> FEATURE:
<221> NAME/KEY: misc_feature
<222> LOCATION: (8)..(8)
<223> OTHER INFORMATION: n is a, c, g, or t

<400> SEQUENCE: 185
tggtgtanga aagaaagacc                                               20

<210> SEQ ID NO 186
<211> LENGTH: 20
<212> TYPE: DNA
<213> ORGANISM: Artificial Sequence
<220> FEATURE:
<223> OTHER INFORMATION: Minimum Identifier
<220> FEATURE:
<221> NAME/KEY: misc_feature
<222> LOCATION: (8)..(8)
<223> OTHER INFORMATION: n is a, c, g, or t

<400> SEQUENCE: 186
tggtgtanga gagaaagacc                                               20

<210> SEQ ID NO 187
<211> LENGTH: 20
<212> TYPE: DNA
<213> ORGANISM: Artificial Sequence
<220> FEATURE:
<223> OTHER INFORMATION: Minimum Identifier

<400> SEQUENCE: 187
ggagtgccat aactataata                                               20

<210> SEQ ID NO 188
<211> LENGTH: 20
<212> TYPE: DNA
<213> ORGANISM: Artificial Sequence
<220> FEATURE:
<223> OTHER INFORMATION: Minimum Identifier

<400> SEQUENCE: 188
ggagtgccat gactataata                                               20
```

```
<210> SEQ ID NO 189
<211> LENGTH: 20
<212> TYPE: DNA
<213> ORGANISM: Artificial Sequence
<220> FEATURE:
<223> OTHER INFORMATION: Minimum Identifier

<400> SEQUENCE: 189
ctctcttctt gctctagaga                                               20

<210> SEQ ID NO 190
<211> LENGTH: 20
<212> TYPE: DNA
<213> ORGANISM: Artificial Sequence
<220> FEATURE:
<223> OTHER INFORMATION: Minimum Identifier

<400> SEQUENCE: 190
ctctcttctt actctagaga                                               20

<210> SEQ ID NO 191
<211> LENGTH: 20
<212> TYPE: DNA
<213> ORGANISM: Artificial Sequence
<220> FEATURE:
<223> OTHER INFORMATION: Minimum Identifier

<400> SEQUENCE: 191
aaggaattga gtcttgttgg                                               20

<210> SEQ ID NO 192
<211> LENGTH: 20
<212> TYPE: DNA
<213> ORGANISM: Artificial Sequence
<220> FEATURE:
<223> OTHER INFORMATION: Minimum Identifier

<400> SEQUENCE: 192
aaggaattga ttcttgttgg                                               20

<210> SEQ ID NO 193
<211> LENGTH: 20
<212> TYPE: DNA
<213> ORGANISM: Artificial Sequence
<220> FEATURE:
<223> OTHER INFORMATION: Minimum Identifier

<400> SEQUENCE: 193
ccactaactg ttgcgcaagt                                               20

<210> SEQ ID NO 194
<211> LENGTH: 20
<212> TYPE: DNA
<213> ORGANISM: Artificial Sequence
<220> FEATURE:
<223> OTHER INFORMATION: Minimum Identifier

<400> SEQUENCE: 194
ccactaactg ctgcgcaagt                                               20

<210> SEQ ID NO 195
<211> LENGTH: 20
<212> TYPE: DNA
<213> ORGANISM: Artificial Sequence
<220> FEATURE:
<223> OTHER INFORMATION: Minimum Identifier
```

```
<400> SEQUENCE: 195
aaaacacgca tgactaacta                                              20

<210> SEQ ID NO 196
<211> LENGTH: 20
<212> TYPE: DNA
<213> ORGANISM: Artificial Sequence
<220> FEATURE:
<223> OTHER INFORMATION: Minimum Identifier

<400> SEQUENCE: 196
aaaacacgca cgactaacta                                              20

<210> SEQ ID NO 197
<211> LENGTH: 20
<212> TYPE: DNA
<213> ORGANISM: Artificial Sequence
<220> FEATURE:
<223> OTHER INFORMATION: Minimum Identifier

<400> SEQUENCE: 197
cgaatcgagc aagggcttcg                                              20

<210> SEQ ID NO 198
<211> LENGTH: 20
<212> TYPE: DNA
<213> ORGANISM: Artificial Sequence
<220> FEATURE:
<223> OTHER INFORMATION: Minimum Identifier

<400> SEQUENCE: 198
cgaatcgagc gagggcttcg                                              20

<210> SEQ ID NO 199
<211> LENGTH: 20
<212> TYPE: DNA
<213> ORGANISM: Artificial Sequence
<220> FEATURE:
<223> OTHER INFORMATION: Minimum Identifier

<400> SEQUENCE: 199
tataaagttc gaaacccatc                                              20

<210> SEQ ID NO 200
<211> LENGTH: 20
<212> TYPE: DNA
<213> ORGANISM: Artificial Sequence
<220> FEATURE:
<223> OTHER INFORMATION: Minimum Identifier

<400> SEQUENCE: 200
tataaagttc caaacccatc                                              20

<210> SEQ ID NO 201
<211> LENGTH: 21
<212> TYPE: DNA
<213> ORGANISM: Artificial Sequence
<220> FEATURE:
<223> OTHER INFORMATION: Minimum Identifier

<400> SEQUENCE: 201
aggttggaag ttgatcaagc a                                            21

<210> SEQ ID NO 202
<211> LENGTH: 21
```

<212> TYPE: DNA
<213> ORGANISM: Artificial Sequence
<220> FEATURE:
<223> OTHER INFORMATION: Minimum Identifier

<400> SEQUENCE: 202
aggttggaag atgatcaagc a                                              21

<210> SEQ ID NO 203
<211> LENGTH: 21
<212> TYPE: DNA
<213> ORGANISM: Artificial Sequence
<220> FEATURE:
<223> OTHER INFORMATION: Minimum Identifier

<400> SEQUENCE: 203
agactgtgga aagctgcaaa t                                              21

<210> SEQ ID NO 204
<211> LENGTH: 21
<212> TYPE: DNA
<213> ORGANISM: Artificial Sequence
<220> FEATURE:
<223> OTHER INFORMATION: Minimum Identifier

<400> SEQUENCE: 204
agactgtgga gagctgcaaa t                                              21

<210> SEQ ID NO 205
<211> LENGTH: 20
<212> TYPE: DNA
<213> ORGANISM: Artificial Sequence
<220> FEATURE:
<223> OTHER INFORMATION: Minimum Identifier
<220> FEATURE:
<221> NAME/KEY: misc_feature
<222> LOCATION: (15)..(15)
<223> OTHER INFORMATION: n is a, c, g, or t

<400> SEQUENCE: 205
tgatttcctt ctaancttgc                                                20

<210> SEQ ID NO 206
<211> LENGTH: 20
<212> TYPE: DNA
<213> ORGANISM: Artificial Sequence
<220> FEATURE:
<223> OTHER INFORMATION: Minimum Identifier
<220> FEATURE:
<221> NAME/KEY: misc_feature
<222> LOCATION: (15)..(15)
<223> OTHER INFORMATION: n is a, c, g, or t

<400> SEQUENCE: 206
tgatttcctt gtaancttgc                                                20

<210> SEQ ID NO 207
<211> LENGTH: 20
<212> TYPE: DNA
<213> ORGANISM: Artificial Sequence
<220> FEATURE:
<223> OTHER INFORMATION: Minimum Identifier

<400> SEQUENCE: 207 tcctttstaag gttggacatc                                               20

<210> SEQ ID NO 208

```
<211> LENGTH: 20
<212> TYPE: DNA
<213> ORGANISM: Artificial Sequence
<220> FEATURE:
<223> OTHER INFORMATION: Minimum Identifier

<400> SEQUENCE: 208 tcctttstaag cttggacatc                                              20

<210> SEQ ID NO 209
<211> LENGTH: 20
<212> TYPE: DNA
<213> ORGANISM: Artificial Sequence
<220> FEATURE:
<223> OTHER INFORMATION: Minimum Identifier
<220> FEATURE:
<221> NAME/KEY: misc_feature
<222> LOCATION: (4)..(5)
<223> OTHER INFORMATION: n is a, c, g, or t

<400> SEQUENCE: 209
ttgnntcttt atgactgccc                                               20

<210> SEQ ID NO 210
<211> LENGTH: 20
<212> TYPE: DNA
<213> ORGANISM: Artificial Sequence
<220> FEATURE:
<223> OTHER INFORMATION: Minimum Identifier
<220> FEATURE:
<221> NAME/KEY: misc_feature
<222> LOCATION: (4)..(5)
<223> OTHER INFORMATION: n is a, c, g, or t

<400> SEQUENCE: 210
ttgnntcttt ttgactgccc                                               20

<210> SEQ ID NO 211
<211> LENGTH: 20
<212> TYPE: DNA
<213> ORGANISM: Artificial Sequence
<220> FEATURE:
<223> OTHER INFORMATION: Minimum Identifier

<400> SEQUENCE: 211
accaaartcc atcagtttga                                               20

<210> SEQ ID NO 212
<211> LENGTH: 20
<212> TYPE: DNA
<213> ORGANISM: Artificial Sequence
<220> FEATURE:
<223> OTHER INFORMATION: Minimum Identifier

<400> SEQUENCE: 212
accaaartcc ttcagtttga                                               20

<210> SEQ ID NO 213
<211> LENGTH: 20
<212> TYPE: DNA
<213> ORGANISM: Artificial Sequence
<220> FEATURE:
<223> OTHER INFORMATION: Minimum Identifier

<400> SEQUENCE: 213
cagcaccaaa atccwtcagt                                               20
```

```
<210> SEQ ID NO 214
<211> LENGTH: 20
<212> TYPE: DNA
<213> ORGANISM: Artificial Sequence
<220> FEATURE:
<223> OTHER INFORMATION: Minimum Identifier

<400> SEQUENCE: 214
cagcaccaaa gtccwtcagt                                               20

<210> SEQ ID NO 215
<211> LENGTH: 20
<212> TYPE: DNA
<213> ORGANISM: Artificial Sequence
<220> FEATURE:
<223> OTHER INFORMATION: Minimum Identifier

<400> SEQUENCE: 215
accaaartcc atcagtttga                                               20

<210> SEQ ID NO 216
<211> LENGTH: 20
<212> TYPE: DNA
<213> ORGANISM: Artificial Sequence
<220> FEATURE:
<223> OTHER INFORMATION: Minimum Identifier

<400> SEQUENCE: 216
accaaartcc ttcagtttga                                               20

<210> SEQ ID NO 217
<211> LENGTH: 20
<212> TYPE: DNA
<213> ORGANISM: Artificial Sequence
<220> FEATURE:
<223> OTHER INFORMATION: Minimum Identifier

<400> SEQUENCE: 217
ttttcctact agtgcattga                                               20

<210> SEQ ID NO 218
<211> LENGTH: 20
<212> TYPE: DNA
<213> ORGANISM: Artificial Sequence
<220> FEATURE:
<223> OTHER INFORMATION: Minimum Identifier

<400> SEQUENCE: 218
ttttcctact tgtgcattga                                               20

<210> SEQ ID NO 219
<211> LENGTH: 20
<212> TYPE: DNA
<213> ORGANISM: Artificial Sequence
<220> FEATURE:
<223> OTHER INFORMATION: Minimum Identifier

<400> SEQUENCE: 219 tcgccccaa gctttcccaa                                                20

<210> SEQ ID NO 220
<211> LENGTH: 20
<212> TYPE: DNA
<213> ORGANISM: Artificial Sequence
<220> FEATURE:
<223> OTHER INFORMATION: Minimum Identifier
```

```
<400> SEQUENCE: 220
tcgcccccaa tctttcccaa                                               20

<210> SEQ ID NO 221
<211> LENGTH: 20
<212> TYPE: DNA
<213> ORGANISM: Artificial Sequence
<220> FEATURE:
<223> OTHER INFORMATION: Minimum Identifier

<400> SEQUENCE: 221
tcctaaagat aaataagga                                                20

<210> SEQ ID NO 222
<211> LENGTH: 20
<212> TYPE: DNA
<213> ORGANISM: Artificial Sequence
<220> FEATURE:
<223> OTHER INFORMATION: Minimum Identifier

<400> SEQUENCE: 222
tcctaaagat gaaataagga                                               20

<210> SEQ ID NO 223
<211> LENGTH: 20
<212> TYPE: DNA
<213> ORGANISM: Artificial Sequence
<220> FEATURE:
<223> OTHER INFORMATION: Minimum Identifier

<400> SEQUENCE: 223
tgatttcatt actcctatac                                               20

<210> SEQ ID NO 224
<211> LENGTH: 20
<212> TYPE: DNA
<213> ORGANISM: Artificial Sequence
<220> FEATURE:
<223> OTHER INFORMATION: Minimum Identifier

<400> SEQUENCE: 224
tgatttcatt cctcctatac                                               20

<210> SEQ ID NO 225
<211> LENGTH: 21
<212> TYPE: DNA
<213> ORGANISM: Artificial Sequence
<220> FEATURE:
<223> OTHER INFORMATION: Probe

<400> SEQUENCE: 225
caactaaagg tatacatgca c                                             21

<210> SEQ ID NO 226
<211> LENGTH: 19
<212> TYPE: DNA
<213> ORGANISM: Artificial Sequence
<220> FEATURE:
<223> OTHER INFORMATION: Probe

<400> SEQUENCE: 226
actaaaggta tgcatgcac                                                19

<210> SEQ ID NO 227
<211> LENGTH: 15
```

```
<212> TYPE: DNA
<213> ORGANISM: Artificial Sequence
<220> FEATURE:
<223> OTHER INFORMATION: Probe

<400> SEQUENCE: 227
ccacgtatgg tctct                                                          15

<210> SEQ ID NO 228
<211> LENGTH: 15
<212> TYPE: DNA
<213> ORGANISM: Artificial Sequence
<220> FEATURE:
<223> OTHER INFORMATION: Probe

<400> SEQUENCE: 228
ccacgtttgg tctct                                                          15

<210> SEQ ID NO 229
<211> LENGTH: 19
<212> TYPE: DNA
<213> ORGANISM: Artificial Sequence
<220> FEATURE:
<223> OTHER INFORMATION: Probe

<400> SEQUENCE: 229
caagtttctt cctaacaat                                                      19

<210> SEQ ID NO 230
<211> LENGTH: 19
<212> TYPE: DNA
<213> ORGANISM: Artificial Sequence
<220> FEATURE:
<223> OTHER INFORMATION: Probe

<400> SEQUENCE: 230
caagtttctt cgtaacaat                                                      19

<210> SEQ ID NO 231
<211> LENGTH: 17
<212> TYPE: DNA
<213> ORGANISM: Artificial Sequence
<220> FEATURE:
<223> OTHER INFORMATION: Probe

<400> SEQUENCE: 231
caaagctaac acaaata                                                        17

<210> SEQ ID NO 232
<211> LENGTH: 18
<212> TYPE: DNA
<213> ORGANISM: Artificial Sequence
<220> FEATURE:
<223> OTHER INFORMATION: Probe

<400> SEQUENCE: 232
aaagctacaa cacaaata                                                       18

<210> SEQ ID NO 233
<211> LENGTH: 17
<212> TYPE: DNA
<213> ORGANISM: Artificial Sequence
<220> FEATURE:
<223> OTHER INFORMATION: Probe

<400> SEQUENCE: 233
```
ttctactctt agcaaca                                                17

<210> SEQ ID NO 234
<211> LENGTH: 16
<212> TYPE: DNA
<213> ORGANISM: Artificial Sequence
<220> FEATURE:
<223> OTHER INFORMATION: Probe

<400> SEQUENCE: 234
tctactctta gcgaca                                                 16

<210> SEQ ID NO 235
<211> LENGTH: 15
<212> TYPE: DNA
<213> ORGANISM: Artificial Sequence
<220> FEATURE:
<223> OTHER INFORMATION: Probe

<400> SEQUENCE: 235
tcaactccga aacgg                                                  15

<210> SEQ ID NO 236
<211> LENGTH: 17
<212> TYPE: DNA
<213> ORGANISM: Artificial Sequence
<220> FEATURE:
<223> OTHER INFORMATION: Probe

<400> SEQUENCE: 236
caactccgaa atggaac                                                17

<210> SEQ ID NO 237
<211> LENGTH: 18
<212> TYPE: DNA
<213> ORGANISM: Artificial Sequence
<220> FEATURE:
<223> OTHER INFORMATION: Probe

<400> SEQUENCE: 237
tatgtgcgac aagatatc                                               18

<210> SEQ ID NO 238
<211> LENGTH: 19
<212> TYPE: DNA
<213> ORGANISM: Artificial Sequence
<220> FEATURE:
<223> OTHER INFORMATION: Probe

<400> SEQUENCE: 238
ctatgtgcga caatatatc                                              19

<210> SEQ ID NO 239
<211> LENGTH: 14
<212> TYPE: DNA
<213> ORGANISM: Artificial Sequence
<220> FEATURE:
<223> OTHER INFORMATION: Probe

<400> SEQUENCE: 239
tgatgggttt cgaa                                                   14

<210> SEQ ID NO 240
<211> LENGTH: 15
<212> TYPE: DNA
<213> ORGANISM: Artificial Sequence

```
<220> FEATURE:
<223> OTHER INFORMATION: Probe

<400> SEQUENCE: 240
tgatgggttt ggaac                                                    15

<210> SEQ ID NO 241
<211> LENGTH: 17
<212> TYPE: DNA
<213> ORGANISM: Artificial Sequence
<220> FEATURE:
<223> OTHER INFORMATION: Probe

<400> SEQUENCE: 241
atcaatttgc agctctc                                                  17

<210> SEQ ID NO 242
<211> LENGTH: 16
<212> TYPE: DNA
<213> ORGANISM: Artificial Sequence
<220> FEATURE:
<223> OTHER INFORMATION: Probe

<400> SEQUENCE: 242
caatttgcag ctttcc                                                   16

<210> SEQ ID NO 243
<211> LENGTH: 16
<212> TYPE: DNA
<213> ORGANISM: Artificial Sequence
<220> FEATURE:
<223> OTHER INFORMATION: Probe

<400> SEQUENCE: 243
accttcaatg cacaag                                                   16

<210> SEQ ID NO 244
<211> LENGTH: 17
<212> TYPE: DNA
<213> ORGANISM: Artificial Sequence
<220> FEATURE:
<223> OTHER INFORMATION: Probe

<400> SEQUENCE: 244
accttcaatg cactagt                                                  17

<210> SEQ ID NO 245
<211> LENGTH: 15
<212> TYPE: DNA
<213> ORGANISM: Artificial Sequence
<220> FEATURE:
<223> OTHER INFORMATION: Probe

<400> SEQUENCE: 245
ttgggaaagg ttggg                                                    15

<210> SEQ ID NO 246
<211> LENGTH: 15
<212> TYPE: DNA
<213> ORGANISM: Artificial Sequence
<220> FEATURE:
<223> OTHER INFORMATION: Probe

<400> SEQUENCE: 246
ttgggaaagt ttggg                                                    15
```

```
<210> SEQ ID NO 247
<211> LENGTH: 20
<212> TYPE: DNA
<213> ORGANISM: Artificial Sequence
<220> FEATURE:
<223> OTHER INFORMATION: Probe

<400> SEQUENCE: 247
catctgatcc taaagataaa                                               20

<210> SEQ ID NO 248
<211> LENGTH: 18
<212> TYPE: DNA
<213> ORGANISM: Artificial Sequence
<220> FEATURE:
<223> OTHER INFORMATION: Probe

<400> SEQUENCE: 248
tctgatccta aagatgaa                                                 18

<210> SEQ ID NO 249
<211> LENGTH: 19
<212> TYPE: DNA
<213> ORGANISM: Artificial Sequence
<220> FEATURE:
<223> OTHER INFORMATION: Probe

<400> SEQUENCE: 249
tctgatttca ttactccta                                                19

<210> SEQ ID NO 250
<211> LENGTH: 19
<212> TYPE: DNA
<213> ORGANISM: Artificial Sequence
<220> FEATURE:
<223> OTHER INFORMATION: Probe

<400> SEQUENCE: 250
tgatttcatt cctcctata                                                19
```